United States Patent
Schuh

(10) Patent No.: US 12,138,003 B2
(45) Date of Patent: Nov. 12, 2024

(54) MEDICAL INSTRUMENTS INCLUDING WRISTS WITH HYBRID REDIRECT SURFACES

(71) Applicant: Auris Health, Inc., Redwood City, CA (US)

(72) Inventor: Travis Michael Schuh, Los Altos, CA (US)

(73) Assignee: Auris Health, Inc., Redwood City, CA (US)

( * ) Notice: Subject to any disclaimer, the term of this patent is extended or adjusted under 35 U.S.C. 154(b) by 1011 days.

(21) Appl. No.: 16/909,172

(22) Filed: Jun. 23, 2020

(65) Prior Publication Data

US 2020/0405423 A1 Dec. 31, 2020

Related U.S. Application Data

(60) Provisional application No. 62/866,205, filed on Jun. 25, 2019.

(51) Int. Cl.
*A61B 34/00* (2016.01)
*A61B 17/00* (2006.01)
(Continued)

(52) U.S. Cl.
CPC .............. *A61B 34/71* (2016.02); *A61B 17/29* (2013.01); *A61B 18/1442* (2013.01);
(Continued)

(58) Field of Classification Search
CPC ..... A61B 34/71; A61B 17/29; A61B 18/1442; A61B 34/30; A61B 2017/00327
See application file for complete search history.

(56) References Cited

U.S. PATENT DOCUMENTS 3,763,860 A 10/1973 Clarke
4,040,413 A 8/1977 Ohshiro
(Continued)

FOREIGN PATENT DOCUMENTS

CN 101443069 5/2009
CN 100515347 7/2009
(Continued)

OTHER PUBLICATIONS

Hernansanz et al, 2015, A multi-robot cooperation strategy for dexterous task oriented teleoperation, 2015, Elsevier, Robotics and Autonomous Systems, 68(205):156-172.
(Continued)

*Primary Examiner* — Shaun L David
*Assistant Examiner* — Rachael L Geiger
(74) *Attorney, Agent, or Firm* — Frost Brown Todd LLP

(57) ABSTRACT

Certain aspects relate to medical instruments including wrists with hybrid redirect surfaces. Such medical instruments can include, for example, a shaft with a wrist positioned at a distal end. The wrist can include a proximal clevis connected to the shaft and a distal clevis pivotally connected to the proximal clevis. The wrist can also include a static redirect surface, such as a face of a clevis, and a dynamic redirect surface, such as a pulley. The instrument can include an end effector connected to the distal clevis. A plurality of pull wires can extend through the shaft and the wrist and engage with and actuate the wrist and the end effector. A first pull wire segment of the plurality of pull wires can engage the static redirect surface, and a second pull wire segment of the plurality of pull wires can engage the dynamic redirect surface.

19 Claims, 29 Drawing Sheets

(51) Int. Cl.
  *A61B 17/29*  (2006.01)
  *A61B 18/00*  (2006.01)
  *A61B 18/12*  (2006.01)
  *A61B 18/14*  (2006.01)
  *A61B 34/30*  (2016.01)

(52) U.S. Cl.
  CPC .... *A61B 34/30* (2016.02); *A61B 2017/00327* (2013.01); *A61B 2018/00595* (2013.01); *A61B 2018/126* (2013.01); *A61B 2034/301* (2016.02); *A61B 2034/302* (2016.02); *A61B 2034/303* (2016.02); *A61B 2034/305* (2016.02); *A61B 2218/002* (2013.01); *A61B 2218/007* (2013.01)

(56) References Cited

U.S. PATENT DOCUMENTS

| | | | |
|---|---|---|---|
| 4,198,960 A | 4/1980 | Utsugi |
| 4,470,407 A | 9/1984 | Hussein |
| 4,532,935 A | 8/1985 | Wang et al. |
| 4,685,458 A | 8/1987 | Leckrone |
| 4,747,405 A | 5/1988 | Leckrone |
| 4,854,301 A | 8/1989 | Nakajima |
| 4,898,574 A | 2/1990 | Uchiyama et al. |
| 4,983,165 A | 1/1991 | Loiterman |
| 5,029,574 A | 7/1991 | Shimamura et al. |
| 5,085,659 A | 2/1992 | Rydell |
| 5,150,452 A | 9/1992 | Pollack et al. |
| 5,196,023 A | 3/1993 | Martin |
| 5,217,465 A | 6/1993 | Steppe |
| 5,308,323 A | 5/1994 | Sogawa et al. |
| 5,318,589 A | 6/1994 | Lichtman |
| 5,325,848 A | 7/1994 | Adams et al. |
| 5,342,381 A | 8/1994 | Tidemand |
| 5,344,395 A | 9/1994 | Whalen et al. |
| 5,353,783 A | 10/1994 | Nakao et al. |
| 5,370,609 A | 12/1994 | Drasler et al. |
| 5,372,124 A | 12/1994 | Takayama et al. |
| 5,411,016 A | 5/1995 | Kume |
| 5,431,649 A | 7/1995 | Mulier et al. |
| 5,441,485 A | 8/1995 | Peters |
| 5,449,356 A | 9/1995 | Walbrink |
| 5,450,843 A | 9/1995 | Moll et al. |
| 5,472,426 A | 12/1995 | Bonati et al. |
| 5,496,267 A | 3/1996 | Drasler |
| 5,501,667 A | 3/1996 | Verduin, Jr. |
| 5,520,684 A | 5/1996 | Imran |
| 5,545,170 A | 8/1996 | Hart |
| 5,562,239 A | 10/1996 | Boiarski et al. |
| 5,562,648 A | 10/1996 | Peterson |
| 5,562,678 A | 10/1996 | Booker |
| 5,572,999 A | 11/1996 | Funda et al. |
| 5,573,535 A | 11/1996 | Viklund |
| 5,613,973 A | 3/1997 | Jackson et al. |
| 5,645,083 A | 7/1997 | Essig et al. |
| 5,653,374 A | 8/1997 | Young et al. |
| 5,658,311 A | 8/1997 | Baden |
| 5,695,500 A | 12/1997 | Taylor et al. |
| 5,697,949 A | 12/1997 | Giurtino et al. |
| 5,710,870 A | 1/1998 | Ohm |
| 5,716,325 A | 2/1998 | Bonutti |
| 5,737,500 A | 4/1998 | Seraji et al. |
| 5,788,667 A | 8/1998 | Stoller |
| 5,792,165 A | 8/1998 | Klieman |
| 5,797,900 A | 8/1998 | Madhani |
| 5,798,627 A | 8/1998 | Gilliland |
| 5,810,770 A | 9/1998 | Chin et al. |
| 5,893,869 A | 4/1999 | Barnhart |
| 5,897,491 A | 4/1999 | Kastenbauer et al. |
| 5,924,175 A | 7/1999 | Lippitt |
| 5,943,056 A | 8/1999 | Sato |
| 5,989,230 A | 11/1999 | Frassica |
| 6,071,281 A | 6/2000 | Burnside et al. |
| 6,093,157 A | 7/2000 | Chandrasekaran |
| 6,110,171 A | 8/2000 | Rydell |
| 6,120,476 A | 9/2000 | Fung et al. |
| 6,120,498 A | 9/2000 | Jani et al. |
| 6,156,030 A | 12/2000 | Neev |
| 6,174,318 B1 | 1/2001 | Bates et al. |
| 6,206,903 B1 | 3/2001 | Ramans |
| 6,236,906 B1 | 5/2001 | Muller |
| 6,183,435 B1 | 6/2001 | Bumbalough et al. |
| 6,322,557 B1 | 11/2001 | Nikolaevich |
| 6,375,635 B1 | 4/2002 | Moutafis |
| 6,394,998 B1 | 5/2002 | Wallace et al. |
| 6,405,078 B1 | 6/2002 | Moaddeb et al. |
| 6,440,061 B1 | 8/2002 | Wenner et al. |
| 6,508,823 B1 | 1/2003 | Gonon |
| 6,522,906 B1 | 2/2003 | Salisbury et al. |
| 6,577,891 B1 | 6/2003 | Jaross et al. |
| 6,676,668 B2 | 1/2004 | Mercereau et al. |
| 6,685,698 B2 | 2/2004 | Morley et al. |
| 6,706,050 B1 | 3/2004 | Giannadakis |
| 7,282,055 B2 | 10/2007 | Tsuruta |
| 7,559,934 B2 | 7/2009 | Teague et al. |
| 7,736,356 B2 | 6/2010 | Cooper et al. |
| 7,963,911 B2 | 6/2011 | Turliuc |
| 7,987,046 B1 | 7/2011 | Peterman |
| 8,002,713 B2 | 8/2011 | Heske |
| 8,004,229 B2 | 8/2011 | Nowlin et al. |
| 8,038,598 B2 | 10/2011 | Khachi |
| 8,092,397 B2 | 1/2012 | Wallace et al. |
| 8,187,173 B2 | 5/2012 | Miyoshi |
| 8,257,303 B2 | 9/2012 | Moll et al. |
| 8,480,595 B2 | 7/2013 | Speeg |
| 8,523,762 B2 | 9/2013 | Miyamoto et al. |
| 8,540,748 B2 | 9/2013 | Murphy et al. |
| 8,541,970 B2 | 9/2013 | Nowlin |
| 8,749,190 B2 | 6/2014 | Nowlin et al. |
| 8,786,241 B2 | 7/2014 | Nowlin et al. |
| 8,820,603 B2 | 9/2014 | Shelton et al. |
| 8,821,480 B2 | 9/2014 | Burbank |
| 8,882,660 B2 | 11/2014 | Phee et al. |
| 8,945,163 B2 | 2/2015 | Voegele et al. |
| 8,956,280 B2 | 2/2015 | Eversull et al. |
| 9,179,979 B2 | 11/2015 | Jinno |
| 9,259,282 B2 | 2/2016 | Azizian |
| 9,296,104 B2 | 3/2016 | Swarup et al. |
| 9,345,456 B2 | 5/2016 | Tsonton et al. |
| 9,345,544 B2 | 5/2016 | Hourtash et al. |
| 9,375,284 B2 | 6/2016 | Hourtash |
| 9,415,510 B2 | 8/2016 | Hourtash et al. |
| 9,460,536 B2 | 10/2016 | Hasegawa et al. |
| 9,480,534 B2 | 11/2016 | Bowling |
| 9,504,604 B2 | 11/2016 | Alvarez |
| 9,510,911 B2 | 12/2016 | Hourtash |
| 9,517,106 B2 | 12/2016 | Hourtash et al. |
| 9,561,083 B2 | 2/2017 | Yu et al. |
| 9,566,125 B2 | 2/2017 | Bowling |
| 9,592,042 B2 | 3/2017 | Titus |
| 9,597,152 B2 | 3/2017 | Schaeffer |
| 9,622,827 B2 | 4/2017 | Yu et al. |
| 9,636,184 B2 | 5/2017 | Lee et al. |
| 9,675,422 B2 | 6/2017 | Hourtash et al. |
| 9,687,310 B2 | 6/2017 | Nowlin et al. |
| 9,713,509 B2 | 7/2017 | Schuh et al. |
| 9,727,963 B2 | 8/2017 | Mintz et al. |
| 9,730,757 B2 | 8/2017 | Brudniok |
| 9,737,371 B2 | 8/2017 | Romo et al. |
| 9,737,373 B2 | 8/2017 | Schuh |
| 9,744,335 B2 | 8/2017 | Jiang |
| 9,763,741 B2 | 9/2017 | Alvarez et al. |
| 9,788,910 B2 | 10/2017 | Schuh |
| 9,844,412 B2 | 12/2017 | Bogusky et al. |
| 9,867,635 B2 | 1/2018 | Alvarez et al. |
| 9,918,681 B2 | 3/2018 | Wallace et al. |
| 9,931,025 B1 | 4/2018 | Graetzel et al. |
| 9,943,962 B2 | 4/2018 | Sattler et al. |
| 9,949,749 B2 | 4/2018 | Noonan et al. |
| 9,955,986 B2 | 5/2018 | Shah |
| 9,962,228 B2 | 5/2018 | Schuh et al. |
| 9,980,785 B2 | 5/2018 | Schuh |
| 9,993,313 B2 | 6/2018 | Schuh et al. |

(56) References Cited

U.S. PATENT DOCUMENTS

| | | |
|---|---|---|
| 10,016,900 B1 | 7/2018 | Meyer et al. |
| 10,022,192 B1 | 7/2018 | Ummalaneni |
| 10,029,367 B2 | 7/2018 | Hourtash |
| 10,071,479 B2 | 9/2018 | Swarup et al. |
| 10,080,576 B2 | 9/2018 | Romo et al. |
| 10,117,713 B2 | 11/2018 | Moctezuma de la Barrera |
| 10,130,429 B1 | 11/2018 | Weir |
| 10,136,949 B2 | 11/2018 | Felder et al. |
| 10,136,959 B2 | 11/2018 | Mintz et al. |
| 10,145,747 B1 | 12/2018 | Lin et al. |
| 10,149,720 B2 | 12/2018 | Romo |
| 10,154,822 B2 | 12/2018 | Henderson |
| 10,159,532 B1 | 12/2018 | Ummalaneni et al. |
| 10,159,533 B2 | 12/2018 | Moll et al. |
| 10,169,875 B2 | 1/2019 | Mintz et al. |
| 10,219,868 B2 | 3/2019 | Weir |
| 10,219,874 B2 | 3/2019 | Yu et al. |
| 10,231,793 B2 | 3/2019 | Romo |
| 10,231,867 B2 | 3/2019 | Alvarez et al. |
| 10,244,926 B2 | 4/2019 | Noonan et al. |
| 10,285,574 B2 | 5/2019 | Landey et al. |
| 10,299,870 B2 | 5/2019 | Connolly et al. |
| 10,314,463 B2 | 6/2019 | Agrawal et al. |
| 10,314,661 B2 | 6/2019 | Bowling |
| 10,327,855 B2 | 6/2019 | Hourtash et al. |
| 10,350,017 B2 | 7/2019 | Bowling |
| 10,350,390 B2 | 7/2019 | Moll et al. |
| 10,383,765 B2 | 8/2019 | Alvarez et al. |
| 10,398,518 B2 | 9/2019 | Yu et al. |
| 10,405,939 B2 | 9/2019 | Romo et al. |
| 10,405,940 B2 | 9/2019 | Romo |
| 10,426,559 B2 | 10/2019 | Graetzel et al. |
| 10,426,661 B2 | 10/2019 | Kintz |
| 10,434,660 B2 | 10/2019 | Meyer |
| 10,463,440 B2 | 11/2019 | Bowling |
| 10,464,209 B2 | 11/2019 | Ho et al. |
| 10,470,830 B2 | 11/2019 | Hill |
| 10,482,599 B2 | 11/2019 | Mintz et al. |
| 10,493,241 B2 | 12/2019 | Jiang |
| 10,500,001 B2 | 12/2019 | Yu et al. |
| 10,517,692 B2 | 12/2019 | Eyre et al. |
| 10,524,866 B2 | 1/2020 | Srinivasan |
| 10,539,478 B2 | 1/2020 | Lin |
| 10,543,048 B2 | 1/2020 | Noonan et al. |
| 10,555,778 B2 | 2/2020 | Ummalaneni et al. |
| 10,631,949 B2 | 4/2020 | Schuh et al. |
| 10,639,108 B2 | 5/2020 | Romo et al. |
| 10,639,109 B2 | 5/2020 | Bovay et al. |
| 10,639,114 B2 | 5/2020 | Schuh |
| 10,667,871 B2 | 6/2020 | Romo et al. |
| 10,667,875 B2 | 6/2020 | DeFonzo |
| 10,682,189 B2 | 6/2020 | Schuh et al. |
| 10,702,348 B2 | 7/2020 | Moll et al. |
| 10,716,461 B2 | 7/2020 | Jenkins |
| 10,743,751 B2 | 8/2020 | Landey et al. |
| 10,744,035 B2 | 8/2020 | Alvarez et al. |
| 10,751,140 B2 | 8/2020 | Wallace et al. |
| 10,765,303 B2 | 9/2020 | Graetzel et al. |
| 10,765,487 B2 | 9/2020 | Ho |
| 10,779,898 B2 | 9/2020 | Hill |
| 10,786,329 B2 | 9/2020 | Schuh et al. |
| 10,786,432 B2 | 10/2020 | Mintz et al. |
| 10,792,464 B2 | 10/2020 | Romo et al. |
| 10,792,466 B2 | 10/2020 | Landey et al. |
| 10,813,539 B2 | 10/2020 | Graetzel et al. |
| 10,814,101 B2 | 10/2020 | Jiang |
| 10,820,947 B2 | 11/2020 | Julian |
| 10,820,954 B2 | 11/2020 | Marsot et al. |
| 10,827,913 B2 | 11/2020 | Ummalaneni et al. |
| 10,828,118 B2 | 11/2020 | Schuh et al. |
| 10,835,153 B2 | 11/2020 | Rafii-Tari et al. |
| 10,850,013 B2 | 12/2020 | Hsu |
| 11,399,905 B2 * | 8/2022 | Schuh .................. A61B 34/20 |
| 2002/0019644 A1 | 2/2002 | Hastings |
| 2002/0111608 A1 | 8/2002 | Baerveldt |
| 2002/0111621 A1 | 8/2002 | Wallace et al. |
| 2003/0004455 A1 | 1/2003 | Kadziauskas |
| 2003/0040681 A1 | 2/2003 | Ng et al. |
| 2003/0065358 A1 | 4/2003 | Frecker |
| 2003/0100892 A1 | 5/2003 | Morley et al. |
| 2003/0109780 A1 | 6/2003 | Coste-Maniere et al. |
| 2003/0109877 A1 | 6/2003 | Morley |
| 2003/0109889 A1 | 6/2003 | Mercereau |
| 2003/0158545 A1 | 8/2003 | Hovda et al. |
| 2003/0208189 A1 | 11/2003 | Payman |
| 2004/0143253 A1 | 7/2004 | Vanney |
| 2004/0153093 A1 | 8/2004 | Donovan |
| 2004/0158261 A1 | 8/2004 | Vu |
| 2004/0186349 A1 | 9/2004 | Ewers |
| 2004/0193146 A1 | 9/2004 | Lee et al. |
| 2004/0210116 A1 | 10/2004 | Nakao |
| 2004/0253079 A1 | 12/2004 | Sanchez |
| 2005/0033270 A1 | 2/2005 | Ramans et al. |
| 2005/0054900 A1 | 3/2005 | Mawn |
| 2005/0159645 A1 | 7/2005 | Bertolero |
| 2005/0240178 A1 | 10/2005 | Morley et al. |
| 2005/0261705 A1 | 11/2005 | Gist |
| 2006/0015133 A1 | 1/2006 | Grayzel |
| 2006/0058813 A1 | 3/2006 | Teague |
| 2006/0116693 A1 | 6/2006 | Weisenburgh |
| 2006/0135963 A1 | 6/2006 | Kick |
| 2006/0156875 A1 | 7/2006 | McRury et al. |
| 2006/0161137 A1 | 7/2006 | Orban et al. |
| 2006/0189891 A1 | 8/2006 | Waxman et al. |
| 2007/0016164 A1 | 1/2007 | Dudney et al. |
| 2007/0027443 A1 | 2/2007 | Rose |
| 2007/0027534 A1 | 2/2007 | Bergheim |
| 2007/0032906 A1 | 2/2007 | Sutherland et al. |
| 2007/0106304 A1 | 5/2007 | Hammack |
| 2007/0123855 A1 | 5/2007 | Morley et al. |
| 2007/0135803 A1 | 6/2007 | Belson |
| 2007/0208375 A1 | 9/2007 | Nishizawa |
| 2007/0213668 A1 | 9/2007 | Spitz |
| 2007/0239178 A1 | 10/2007 | Weitzner et al. |
| 2007/0250111 A1 | 10/2007 | Lu |
| 2007/0299427 A1 | 12/2007 | Yeung et al. |
| 2008/0015566 A1 | 1/2008 | Livneh |
| 2008/0021440 A1 | 1/2008 | Solomon |
| 2008/0033467 A1 | 2/2008 | Miyamoto et al. |
| 2008/0045981 A1 | 2/2008 | Margolin et al. |
| 2008/0046122 A1 | 2/2008 | Manzo et al. |
| 2008/0065111 A1 | 3/2008 | Blumenkranz |
| 2008/0065112 A1 | 3/2008 | Tovey et al. |
| 2008/0125698 A1 | 5/2008 | Greg et al. |
| 2008/0187101 A1 | 8/2008 | Gertner |
| 2008/0196533 A1 | 8/2008 | Bergamasco |
| 2008/0228104 A1 | 9/2008 | Uber et al. |
| 2009/0012507 A1 | 1/2009 | Culbertson et al. |
| 2009/0030446 A1 | 1/2009 | Measamer |
| 2009/0036900 A1 | 2/2009 | Moll |
| 2009/0043305 A1 | 2/2009 | Brodbeck |
| 2009/0082634 A1 | 3/2009 | Kathrani et al. |
| 2009/0088774 A1 | 4/2009 | Swarup et al. |
| 2009/0105723 A1 | 4/2009 | Dillinger |
| 2009/0131885 A1 | 5/2009 | Akahoshi |
| 2009/0161827 A1 | 6/2009 | Gertner et al. |
| 2009/0192524 A1 | 7/2009 | Ltkowitz |
| 2009/0227998 A1 | 9/2009 | Aljuri |
| 2009/0248041 A1 | 10/2009 | Williams et al. |
| 2009/0248043 A1 | 10/2009 | Tierney et al. |
| 2009/0264878 A1 | 10/2009 | Carmel et al. |
| 2009/0270760 A1 | 10/2009 | Leimbach et al. |
| 2009/0287188 A1 | 11/2009 | Golden et al. |
| 2009/0299352 A1 | 12/2009 | Zerfas |
| 2009/0312773 A1 | 12/2009 | Cabrera et al. |
| 2010/0004642 A1 | 1/2010 | Lumpkin |
| 2010/0010504 A1 | 1/2010 | Simaan et al. |
| 2010/0011900 A1 | 1/2010 | Burbank |
| 2010/0011901 A1 | 1/2010 | Burbank |
| 2010/0016852 A1 | 1/2010 | Manzo et al. |
| 2010/0016853 A1 | 1/2010 | Burbank |
| 2010/0081965 A1 | 4/2010 | Mugan et al. |
| 2010/0082017 A1 | 4/2010 | Zickler |
| 2010/0179632 A1 | 7/2010 | Bruszewski et al. |

(56) References Cited

U.S. PATENT DOCUMENTS

| | | |
|---|---|---|
| 2010/0204605 A1 | 8/2010 | Blakley |
| 2010/0204646 A1 | 8/2010 | Plicchi et al. |
| 2010/0217235 A1 | 8/2010 | Thorstenson |
| 2010/0225209 A1 | 9/2010 | Goldberg |
| 2010/0228249 A1 | 9/2010 | Mohr |
| 2010/0268211 A1 | 10/2010 | Manwaring et al. |
| 2010/0312141 A1 | 12/2010 | Keast et al. |
| 2010/0331858 A1 | 12/2010 | Simaan et al. |
| 2011/0015483 A1 | 1/2011 | Barbagli |
| 2011/0028790 A1 | 2/2011 | Farr et al. |
| 2011/0071541 A1 | 3/2011 | Prisco et al. |
| 2011/0071543 A1 | 3/2011 | Prisco et al. |
| 2011/0106146 A1 | 5/2011 | Jeong |
| 2011/0125165 A1 | 5/2011 | Simaan et al. |
| 2011/0152880 A1 | 6/2011 | Alvarez et al. |
| 2011/0160713 A1 | 6/2011 | Neuberger |
| 2011/0160745 A1 | 6/2011 | Fielding |
| 2011/0167611 A1 | 7/2011 | Williams |
| 2011/0208211 A1 | 8/2011 | Whitfield et al. |
| 2011/0213362 A1 | 9/2011 | Cunningham |
| 2011/0224660 A1 | 9/2011 | Neuberger et al. |
| 2011/0238064 A1 | 9/2011 | Williams et al. |
| 2011/0257641 A1 | 10/2011 | Hastings et al. |
| 2011/0276085 A1 | 11/2011 | Krzyzanowski |
| 2011/0313343 A1 | 12/2011 | Milutinovic et al. |
| 2012/0048759 A1 | 3/2012 | Disch et al. |
| 2012/0069167 A1 | 3/2012 | Liu et al. |
| 2012/0253277 A1 | 4/2012 | Tah et al. |
| 2012/0138586 A1 | 6/2012 | Webster et al. |
| 2012/0138660 A1 | 6/2012 | Shelton, IV et al. |
| 2012/0209315 A1 | 8/2012 | Amat |
| 2012/0232342 A1 | 9/2012 | Reydel |
| 2012/0253332 A1 | 10/2012 | Moll |
| 2012/0259320 A1 | 10/2012 | Loesel et al. |
| 2012/0296318 A1 | 11/2012 | Wellhofer et al. |
| 2013/0006144 A1 | 1/2013 | Clancy |
| 2013/0035537 A1 | 2/2013 | Wallace et al. |
| 2013/0053877 A1 | 2/2013 | BenMaamer |
| 2013/0066136 A1 | 3/2013 | Palese et al. |
| 2013/0085442 A1 | 4/2013 | Shtul et al. |
| 2013/0085486 A1 | 4/2013 | Boutoussov et al. |
| 2013/0096422 A1 | 4/2013 | Boctor |
| 2013/0096574 A1 | 4/2013 | Kang et al. |
| 2013/0110042 A1 | 5/2013 | Humphreys |
| 2013/0110107 A1 | 5/2013 | Smith et al. |
| 2013/0116716 A1 | 5/2013 | Bahls et al. |
| 2013/0144274 A1 | 6/2013 | Stefanchik et al. |
| 2013/0144395 A1 | 6/2013 | Stefanchik |
| 2013/0190796 A1 | 7/2013 | Tilson et al. |
| 2013/0225997 A1 | 8/2013 | Dillard et al. |
| 2013/0226161 A1 | 8/2013 | Hickenbotham |
| 2013/0233908 A1 | 9/2013 | Knodel |
| 2013/0253267 A1 | 9/2013 | Collins |
| 2013/0303876 A1 | 11/2013 | Gelfand et al. |
| 2013/0310819 A1 | 11/2013 | Neuberger et al. |
| 2013/0317519 A1 | 11/2013 | Romo et al. |
| 2013/0334281 A1 | 12/2013 | Williams |
| 2013/0345686 A1 | 12/2013 | Brown |
| 2014/0005681 A1 | 1/2014 | Gee et al. |
| 2014/0039517 A1 | 2/2014 | Bowling |
| 2014/0039681 A1 | 2/2014 | Bowling |
| 2014/0046308 A1 | 2/2014 | Bischoff |
| 2014/0051985 A1 | 2/2014 | Fan et al. |
| 2014/0058365 A1 | 2/2014 | Bille |
| 2014/0058404 A1 | 2/2014 | Hammack |
| 2014/0058428 A1 | 2/2014 | Christopher |
| 2014/0100445 A1 | 4/2014 | Stenzel |
| 2014/0142591 A1 | 5/2014 | Alvarez et al. |
| 2014/0163318 A1 | 6/2014 | Swanstrom |
| 2014/0163736 A1 | 6/2014 | Azizian |
| 2014/0194859 A1 | 7/2014 | Ianchulev |
| 2014/0194905 A1 | 7/2014 | Kappel |
| 2014/0222207 A1 | 8/2014 | Bowling et al. |
| 2014/0243849 A1 | 8/2014 | Saglam et al. |
| 2014/0246473 A1 | 9/2014 | Auld |
| 2014/0257331 A1* | 9/2014 | Kim .................. A61B 34/30 606/130 |
| 2014/0257333 A1 | 9/2014 | Blumenkranz |
| 2014/0275956 A1 | 9/2014 | Fan |
| 2014/0276723 A1 | 9/2014 | Parihar |
| 2014/0276956 A1 | 9/2014 | Crainich |
| 2014/0309655 A1 | 10/2014 | Gal et al. |
| 2014/0316203 A1 | 10/2014 | Carroux et al. |
| 2014/0357984 A1 | 12/2014 | Wallace et al. |
| 2015/0073439 A1 | 3/2015 | Dannaher |
| 2015/0080879 A1 | 3/2015 | Trees |
| 2015/0127045 A1* | 5/2015 | Prestel .................. A61B 34/30 606/208 |
| 2015/0133960 A1 | 5/2015 | Lohmeier |
| 2015/0150635 A1 | 6/2015 | Kilroy |
| 2015/0164522 A1 | 6/2015 | Budiman |
| 2015/0190204 A1 | 7/2015 | Popovi |
| 2015/0201917 A1 | 7/2015 | Snow |
| 2015/0202085 A1 | 7/2015 | Lemonis |
| 2015/0314110 A1 | 11/2015 | Park |
| 2015/0366629 A1 | 12/2015 | Bowling |
| 2015/0374446 A1 | 12/2015 | Malackowski |
| 2016/0022289 A1 | 1/2016 | Wan |
| 2016/0022466 A1 | 1/2016 | Pedtke |
| 2016/0030073 A1 | 2/2016 | Lsakov |
| 2016/0045208 A1 | 2/2016 | Ciulla |
| 2016/0051318 A1 | 2/2016 | Manzo et al. |
| 2016/0066935 A1 | 3/2016 | Nguyen et al. |
| 2016/0158490 A1 | 6/2016 | Leeflang |
| 2016/0183841 A1 | 6/2016 | Duindam et al. |
| 2016/0199984 A1 | 7/2016 | Lohmeier et al. |
| 2016/0235495 A1 | 8/2016 | Wallace et al. |
| 2016/0242858 A1 | 8/2016 | Moctezuma de la Barrera et al. |
| 2016/0249932 A1 | 9/2016 | Rogers et al. |
| 2016/0270865 A1 | 9/2016 | Landey et al. |
| 2016/0287279 A1 | 10/2016 | Bovay et al. |
| 2016/0302871 A1 | 10/2016 | Gregerson et al. |
| 2016/0303743 A1 | 10/2016 | Rockrohr |
| 2016/0310146 A1 | 10/2016 | Levy et al. |
| 2016/0331358 A1 | 11/2016 | Gordon |
| 2016/0367324 A1 | 12/2016 | Sato et al. |
| 2017/0000577 A1 | 1/2017 | Bowling |
| 2017/0007337 A1 | 1/2017 | Dan |
| 2017/0049471 A1 | 2/2017 | Gaffney et al. |
| 2017/0055995 A1 | 3/2017 | Weier |
| 2017/0065227 A1 | 3/2017 | Marrs |
| 2017/0071584 A1 | 3/2017 | Suigetsu et al. |
| 2017/0086934 A1 | 3/2017 | Devengenzo et al. |
| 2017/0095234 A1 | 4/2017 | Prisco et al. |
| 2017/0095295 A1 | 4/2017 | Overmyer |
| 2017/0135706 A1 | 5/2017 | Frey |
| 2017/0151416 A1 | 6/2017 | Kutikov |
| 2017/0165009 A1 | 6/2017 | Chaplin et al. |
| 2017/0172553 A1* | 6/2017 | Chaplin .................. A61B 34/71 |
| 2017/0172680 A1 | 6/2017 | Bowling |
| 2017/0202627 A1 | 7/2017 | Sramek et al. |
| 2017/0209073 A1 | 7/2017 | Sramek et al. |
| 2017/0252096 A1 | 9/2017 | Felder |
| 2017/0258534 A1 | 9/2017 | Hourtash et al. |
| 2017/0265923 A1 | 9/2017 | Privitera |
| 2017/0265954 A1 | 9/2017 | Burbank |
| 2017/0290631 A1 | 10/2017 | Lee et al. |
| 2017/0319289 A1 | 11/2017 | Neff et al. |
| 2017/0333147 A1 | 11/2017 | Bernstein |
| 2018/0000563 A1 | 1/2018 | Shanjani et al. |
| 2018/0025666 A1 | 1/2018 | Ho et al. |
| 2018/0049824 A1 | 2/2018 | Harris |
| 2018/0079090 A1 | 3/2018 | Koenig et al. |
| 2018/0080841 A1 | 3/2018 | Cordoba |
| 2018/0140371 A1 | 5/2018 | Hares et al. |
| 2018/0193049 A1 | 7/2018 | Heck et al. |
| 2018/0206931 A1 | 7/2018 | Scheib |
| 2018/0221038 A1 | 8/2018 | Noonan et al. |
| 2018/0221039 A1 | 8/2018 | Shar |
| 2018/0250085 A1 | 9/2018 | Simi |
| 2018/0279852 A1 | 10/2018 | Rafii-Tari et al. |
| 2018/0289431 A1 | 10/2018 | Draper et al. |
| 2018/0296285 A1 | 10/2018 | Simi et al. |
| 2018/0325499 A1 | 11/2018 | Landey et al. |

(56) References Cited

U.S. PATENT DOCUMENTS

| | | |
|---|---|---|
| 2018/0360435 A1 | 12/2018 | Romo |
| 2019/0000559 A1 | 1/2019 | Berman et al. |
| 2019/0000560 A1 | 1/2019 | Berman et al. |
| 2019/0000576 A1 | 1/2019 | Mintz et al. |
| 2019/0015166 A1 | 1/2019 | Mahoney |
| 2019/0069962 A1 | 3/2019 | Tabandeh et al. |
| 2019/0099231 A1 | 4/2019 | Bruehwiler |
| 2019/0099232 A1 | 4/2019 | Soto et al. |
| 2019/0110839 A1 | 4/2019 | Rafii-Tari et al. |
| 2019/0117320 A1 | 4/2019 | Shoham et al. |
| 2019/0117324 A1 | 4/2019 | Hibner |
| 2019/0151148 A1 | 4/2019 | Alvarez et al. |
| 2019/0142531 A1 | 5/2019 | Wentworth et al. |
| 2019/0167366 A1 | 6/2019 | Ummalaneni |
| 2019/0175009 A1 | 6/2019 | Mintz |
| 2019/0183585 A1 | 6/2019 | Rafii-Tari et al. |
| 2019/0183587 A1 | 6/2019 | Rafii-Tari et al. |
| 2019/0192249 A1 | 6/2019 | Bowling |
| 2019/0216548 A1 | 7/2019 | Ummalaneni |
| 2019/0216576 A1 | 7/2019 | Eyre |
| 2019/0223974 A1 | 7/2019 | Romo |
| 2019/0231460 A1 | 8/2019 | DiMaio |
| 2019/0239890 A1 | 8/2019 | Stokes |
| 2019/0262086 A1 | 8/2019 | Connolly et al. |
| 2019/0269468 A1 | 9/2019 | Hsu et al. |
| 2019/0274764 A1 | 9/2019 | Romo |
| 2019/0290109 A1 | 9/2019 | Agrawal et al. |
| 2019/0298460 A1 | 10/2019 | Al-Jadda |
| 2019/0298464 A1 | 10/2019 | Abbott |
| 2019/0298465 A1 | 10/2019 | Chin |
| 2019/0298469 A1 | 10/2019 | Ramstad et al. |
| 2019/0314616 A1 | 10/2019 | Moll et al. |
| 2019/0336238 A1 | 11/2019 | Yu |
| 2019/0365201 A1 | 12/2019 | Noonan et al. |
| 2019/0365209 A1 | 12/2019 | Ye et al. |
| 2019/0365479 A1 | 12/2019 | Rafii-Tari |
| 2019/0365486 A1 | 12/2019 | Srinivasan et al. |
| 2019/0375383 A1 | 12/2019 | Alvarez |
| 2019/0380787 A1 | 12/2019 | Ye |
| 2019/0380797 A1 | 12/2019 | Yu |
| 2020/0000533 A1 | 1/2020 | Schuh |
| 2020/0030046 A1 | 1/2020 | Bowling |
| 2020/0038123 A1 | 2/2020 | Graetzel |
| 2020/0039086 A1 | 2/2020 | Meyer |
| 2020/0046434 A1 | 2/2020 | Graetzel |
| 2020/0060516 A1 | 2/2020 | Baez |
| 2020/0085516 A1 | 3/2020 | DeFonzo |
| 2020/0093549 A1 | 3/2020 | Chin |
| 2020/0093554 A1 | 3/2020 | Schuh |
| 2020/0100855 A1 | 4/2020 | Leparmentier |
| 2020/0107894 A1 | 4/2020 | Wallace |
| 2020/0121502 A1 | 4/2020 | Kintz |
| 2020/0138531 A1 | 5/2020 | Chaplin |
| 2020/0146769 A1 | 5/2020 | Eyre |
| 2020/0163726 A1 | 5/2020 | Tanner |
| 2020/0170720 A1 | 6/2020 | Ummalaneni |
| 2020/0171660 A1 | 6/2020 | Ho |
| 2020/0188043 A1 | 6/2020 | Yu |
| 2020/0197109 A1 | 6/2020 | Chaplin |
| 2020/0197112 A1 | 6/2020 | Chin |
| 2020/0206472 A1 | 7/2020 | Ma |
| 2020/0217733 A1 | 7/2020 | Lin |
| 2020/0222134 A1 | 7/2020 | Schuh |
| 2020/0237458 A1 | 7/2020 | DeFonzo |
| 2020/0261172 A1 | 8/2020 | Romo |
| 2020/0268459 A1 | 8/2020 | Noonan et al. |
| 2020/0268460 A1 | 8/2020 | Tse |
| 2020/0281787 A1 | 9/2020 | Ruiz |
| 2020/0297437 A1 | 9/2020 | Schuh |
| 2020/0297444 A1 | 9/2020 | Camarillo |
| 2020/0305983 A1 | 10/2020 | Yampolsky |
| 2020/0305989 A1 | 10/2020 | Schuh |
| 2020/0305992 A1 | 10/2020 | Schuh |
| 2020/0315717 A1 | 10/2020 | Bovay |
| 2020/0315723 A1 | 10/2020 | Hassan |
| 2020/0323596 A1 | 10/2020 | Moll |
| 2020/0330167 A1 | 10/2020 | Romo |
| 2020/0345216 A1 | 11/2020 | Jenkins |
| 2020/0352420 A1 | 11/2020 | Graetzel |
| 2020/0360183 A1 | 11/2020 | Alvarez |
| 2020/0367726 A1 | 11/2020 | Landey et al. |
| 2020/0367981 A1 | 11/2020 | Ho et al. |
| 2020/0375678 A1 | 12/2020 | Wallace |

FOREIGN PATENT DOCUMENTS

| | | |
|---|---|---|
| CN | 103298414 | 9/2013 |
| CN | 104619281 | 5/2015 |
| CN | 205729413 | 11/2016 |
| EP | 1 321 106 | 6/2003 |
| EP | 1 849 423 | 10/2007 |
| JP | 2005-270464 | 10/2005 |
| WO | WO 11/161218 | 12/2011 |
| WO | WO 13/107468 | 7/2013 |
| WO | WO 15/153174 | 10/2015 |
| WO | WO 16/137612 | 9/2016 |
| WO | WO 17/114855 | 7/2017 |
| WO | WO 18/069679 | 4/2018 |
| WO | WO 18/189722 | 10/2018 |

OTHER PUBLICATIONS

Ramezanifard et al, 2007, A Novel Modeling Approach for Collision Avoidance in Robotic Surgery, 2007 Science Publications, American Journal of Applied Sciences 4(9):693-699.

International search report and written opinion dated Sep. 10, 2020 in application No. PCT/US2020/039138.

Supplementary European Search Reported dated Sep. 6, 2023, for Application No. 20831738.8, 15 pages.

* cited by examiner

# MEDICAL INSTRUMENTS INCLUDING WRISTS WITH HYBRID REDIRECT SURFACES

PRIORITY APPLICATION

This application claims priority to U.S. Provisional Application No. 62/866,205, filed Jun. 25, 2019, which is incorporated herein by reference in its entirety and for all purposes. Any and all applications for which a foreign or domestic priority claim is identified in the Application Data Sheet as filed with the present application are hereby incorporated by reference under 37 CFR 1.57.

TECHNICAL FIELD

The systems and methods disclosed herein are directed to medical instruments, and more particularly to medical instruments including wrists with hybrid redirect surfaces. The medical instruments including wrists with hybrid redirect surfaces can be implemented on robotic medical systems.

BACKGROUND

Medical procedures, such as laparoscopy, may involve accessing and visualizing an internal region of a patient. In a laparoscopic procedure, a medical instrument can be inserted into an internal region through a laparoscopic access port.

In certain procedures, a robotically-enabled medical system may be used to control the insertion and/or manipulation of the medical instrument and an end effector thereof. The end effector can be connected to an elongated shaft of the medical instrument by an articulable wrist. The robotically-enabled medical system may also include a robotic arm or other instrument positioning device. The robotically-enabled medical system may also include a controller used to control the positioning of the medical instrument during the procedure.

SUMMARY

The systems, methods and devices of this disclosure each have several innovative aspects, no single one of which is solely responsible for the desirable attributes disclosed herein.

This application is directed to medical instruments having a novel wrist architecture that utilizes hybrid redirect surfaces, in which at least one redirect surface is stationary and at least one other is non-stationary.

In a first aspect, a medical instrument is disclosed. The medical instrument includes a shaft extending between a proximal end and a distal end and a wrist positioned at the distal end of the shaft. The wrist includes a proximal clevis connected to the distal end of the shaft, a distal clevis pivotally connected to the proximal clevis, a static redirect surface, and a dynamic redirect surface. The medical instrument also includes an end effector connected to the distal clevis of the wrist and a plurality of pull wires extending through the shaft and the wrist and engaged with the end effector. The plurality of pull wires is configured to actuate the wrist and the end effector. A first pull wire segment of the plurality of pull wires is engaged with the static redirect surface. A second pull wire segment of the plurality of pull wires is engaged with the dynamic redirect surface.

The medical instrument can optionally include one or more of the following features, in any combination: (a) wherein the static redirect surface comprises a stationary surface configured to direct the first pull wire segment from a first direction to a second direction through engagement with the static redirect surface; (b) wherein the static redirect surface is positioned between a proximal pulley configured to rotate in a first plane and a distal pulley configured to rotate in a second plane that is orthogonal to the first plane, and wherein the first pull wire segment engages the proximal pulley, the static redirect surface, and the distal pulley; (c) wherein the proximal pulley is positioned at a proximal end of the distal clevis and the distal pulley is positioned at a distal end of the distal clevis; (d) wherein the dynamic redirect surface comprises a surface of a redirect pulley; (e) wherein the second pull wire segment engages a proximal pulley configured to rotate in a first plane on a first lateral side of the medical instrument, the second pull wire segment engages a distal pulley on a second lateral side of the medical instrument, the distal pulley configured to rotate in a second plane that is orthogonal to the first plane, and the redirect pulley is positioned between the proximal pulley and the distal pulley; (f) wherein the static redirect surface and the dynamic redirect surface are positioned on the distal clevis of the wrist; (g) wherein the end effector comprises at least one jaw, actuation of the first pull wire segment causes the at least one jaw to open, and actuation of the second pull wire segment causes the at least one jaw to close; (h) wherein the wrist comprises an axle pivotally connecting the proximal clevis to the distal clevis, a first open pitch pulley mounted on the axle, a first close pitch pulley mounted on the axle, and wherein the axle extends through a first support leg of the distal clevis, and wherein the first support leg of the distal clevis is positioned between the first open pitch pulley and the first closed pitch pulley; (i) wherein the wrist further comprises a second open pitch pulley mounted on the axle, a second close pitch pulley mounted on the axle, and wherein the axle extends through a second support leg of the distal clevis, wherein the second support leg of the distal clevis is positioned between the second open pitch pulley and the second closed pitch pulley, and wherein the first and second open pitch pulleys are positioned between the first and second support legs of the distal clevis; (j) wherein the proximal clevis comprises first and second support legs, the axle extends through the first and second support legs of the proximal clevis, and the first and second close pitch pulleys, the first and second support legs of the distal clevis, and the first and second open pitch pulleys are positioned between the first and second support legs of the proximal clevis; (k) a first redirect pulley positioned in the proximal clevis configured to rotate about a first axis, and a second redirect pulley positioned in the proximal clevis configured to rotate about a second axis, wherein the second axis is not coaxial with the first axis; (l) wherein the end effector comprises grips of a bipolar energy instrument; and/or (m) wherein the plurality of pull wires comprise n pull wires, and wherein actuation of one or more of the n pull wires facilitates control of n+1 degrees of freedom of the medical instrument.

In another aspect, a medical instrument is disclosed that includes a shaft extending between a proximal end and a distal end and a wrist positioned at the distal end of the shaft. The wrist includes a proximal clevis connected to the distal end of the shaft, a distal clevis pivotally connected to the proximal clevis by an axle, a first pulley rotatably mounted on the axle, and a second pulley rotatably mounted on the axle. The axle extends through a first support leg of the distal clevis that is positioned between the first pulley and the second pulley, and an end effector is connected to the distal clevis of the wrist, the end effector comprising at least one gripping member.

The medical instrument optionally includes one or more of the following features, in any combination: (a) wherein the wrist further comprises a third pulley rotatably mounted on the axle, and a fourth pulley rotatably mounted on the axle, wherein the axle extends through a second support leg of the distal clevis that is positioned between the third pulley and the fourth pulley; (b) wherein the second and third pulleys are positioned between the first and second support legs of the distal clevis; (c) wherein the proximal clevis comprises a third support leg and a fourth support leg, the axle extends through the third and fourth support legs of the proximal clevis, and the first, second, third, and fourth pulleys and the first and second support legs of the distal clevis are positioned between the third and fourth support legs of the proximal clevis; (d) first, second, third, and fourth pull wire segments contacting the first, second, third, and fourth pulleys, respectively, and wherein the first and fourth pull wire segments are associated with a close motion of the end effector and the second and third pull wire segments are associated with an open motion of the end effector; (e) wherein the wrist further comprises a first static redirect surface, a second static redirect surface, a first dynamic redirect surface, and a second dynamic redirect surface; (f) wherein the first static redirect surface comprises a stationary surface configured to redirect the second pull wire segment, the second static redirect surface comprises a stationary surface configured to redirect the third pull wire segment, the first dynamic redirect surface comprises a surface of a first redirect pulley configured to redirect the first pull wire segment, and the second dynamic redirect surface comprises a surface of a second redirect pulley configured to redirect the fourth pull wire segment; (g) wherein the first and second static redirect surfaces and the first and second dynamic redirect surface are positioned on the distal clevis of the wrist; (h) a first redirect pulley positioned in the proximal clevis configured to rotate about a first axis, and a second redirect pulley positioned in the proximal clevis configured to rotate about a second axis, wherein the second axis is not coaxial with the first axis; and/or (i) wherein the first, second, third, and fourth pull wire segments are configured to be actuated to control three degrees of freedom of the medical instrument.

In another aspect, a medical instrument is disclosed that includes a shaft extending between a proximal end and a distal end and a wrist positioned at the distal end of the shaft. The wrist includes a proximal clevis connected to the distal end of the shaft, a distal clevis pivotally connected to the proximal clevis, a first redirect pulley positioned in the proximal clevis and configured to rotate about a first axis, and a second redirect pulley positioned in the proximal clevis and configured to rotate about a second axis, wherein the second axis is not coaxial with the first axis. The instrument also includes an end effector connected to the distal clevis of the wrist.

The medical instrument can optionally include one or more of the following features, in any combination: (a) a third redirect pulley positioned in the proximal clevis and configured to rotate about a third axis, and a fourth redirect pulley positioned in the proximal clevis and configured to rotate about a fourth axis; (b) wherein a first support wall of the proximal clevis is positioned between the first redirect pulley and the second redirect pulley, and a second support wall of the proximal clevis is positioned between the third redirect pulley and the fourth redirect pulley; (d) wherein the proximal clevis does not comprise a support wall between the second redirect pulley and the third redirect pulley; and wherein the second axis and the third axis are coaxial; (e) wherein the first axis and the fourth axis are not coaxial; (f) a plurality of pull wires extending through the shaft and the wrist and engaged with the end effector, wherein the plurality of pull wires is configured to actuate the wrist and the end effector; (g) wherein the plurality of pull wires comprise n pull wires, and wherein actuation of one or more of the n pull wires facilitates control of n+1 degrees of freedom of the medical instrument; (h) wherein the distal clevis comprises a static redirect surface comprising a stationary surface configured to redirect a first pull wire segment extending through the wrist, and a dynamic redirect surface comprising a surface of a distal redirect pulley configured to redirect a second pull wire segment extending through the wrist; and/or (i) wherein actuation of the first pull wire segment causes an opening motion of the end effector, and actuation of the second pull wire segment causes a closing motion of the end effector.

BRIEF DESCRIPTION OF THE DRAWINGS

The disclosed aspects will hereinafter be described in conjunction with the appended drawings, provided to illustrate and not to limit the disclosed aspects, wherein like designations denote like elements.

FIG. 23A is a perspective view of the medical instrument.

FIG. 23B is a perspective view of the medical instrument with a distal clevis illustrated as transparent so as to show static redirect surfaces.

FIG. 23C is a is a first side view of the medical instrument.

FIG. 23D is a second side view of the medical instrument.

FIG. 23E is a top view of a proximal clevis of the medical instrument.

DETAILED DESCRIPTION

1. Overview

Aspects of the present disclosure may be integrated into a robotically-enabled medical system capable of performing a variety of medical procedures, including both minimally invasive, such as laparoscopy, and non-invasive, such as endoscopy, procedures. Among endoscopic procedures, the system may be capable of performing bronchoscopy, ureteroscopy, gastroscopy, etc.

In addition to performing the breadth of procedures, the system may provide additional benefits, such as enhanced imaging and guidance to assist the physician. Additionally, the system may provide the physician with the ability to perform the procedure from an ergonomic position without the need for awkward arm motions and positions. Still further, the system may provide the physician with the ability to perform the procedure with improved ease of use such that one or more of the instruments of the system can be controlled by a single user.

Various embodiments will be described below in conjunction with the drawings for purposes of illustration. It should be appreciated that many other implementations of the disclosed concepts are possible, and various advantages can be achieved with the disclosed implementations. Headings are included herein for reference and to aid in locating various sections. These headings are not intended to limit the scope of the concepts described with respect thereto. Such concepts may have applicability throughout the entire specification.

A. Robotic System—Cart.

Figure 1:
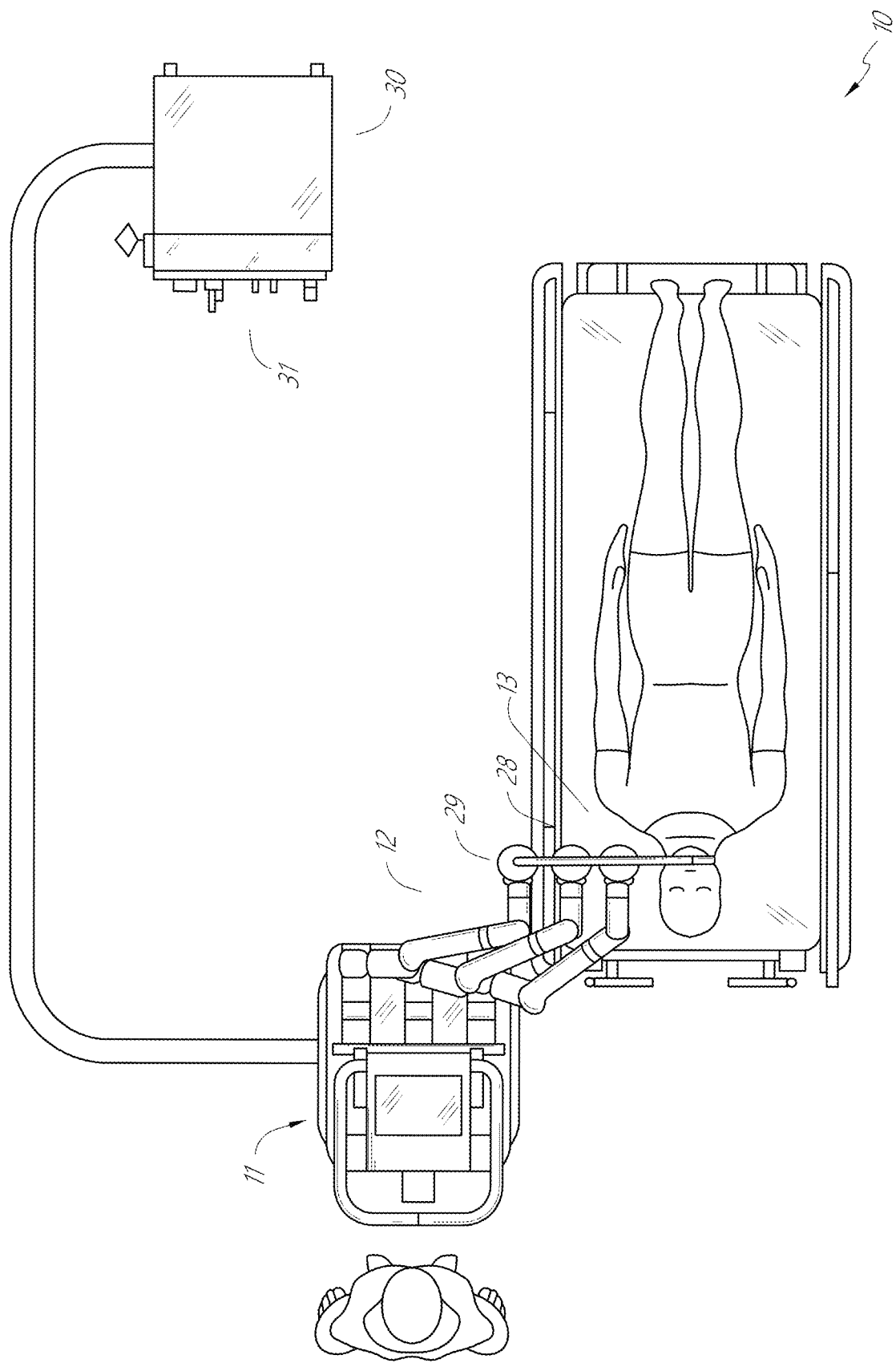
FIG. 1 illustrates an embodiment of a cart-based robotic system arranged for diagnostic and/or therapeutic bronchoscopy.
Figure 2:
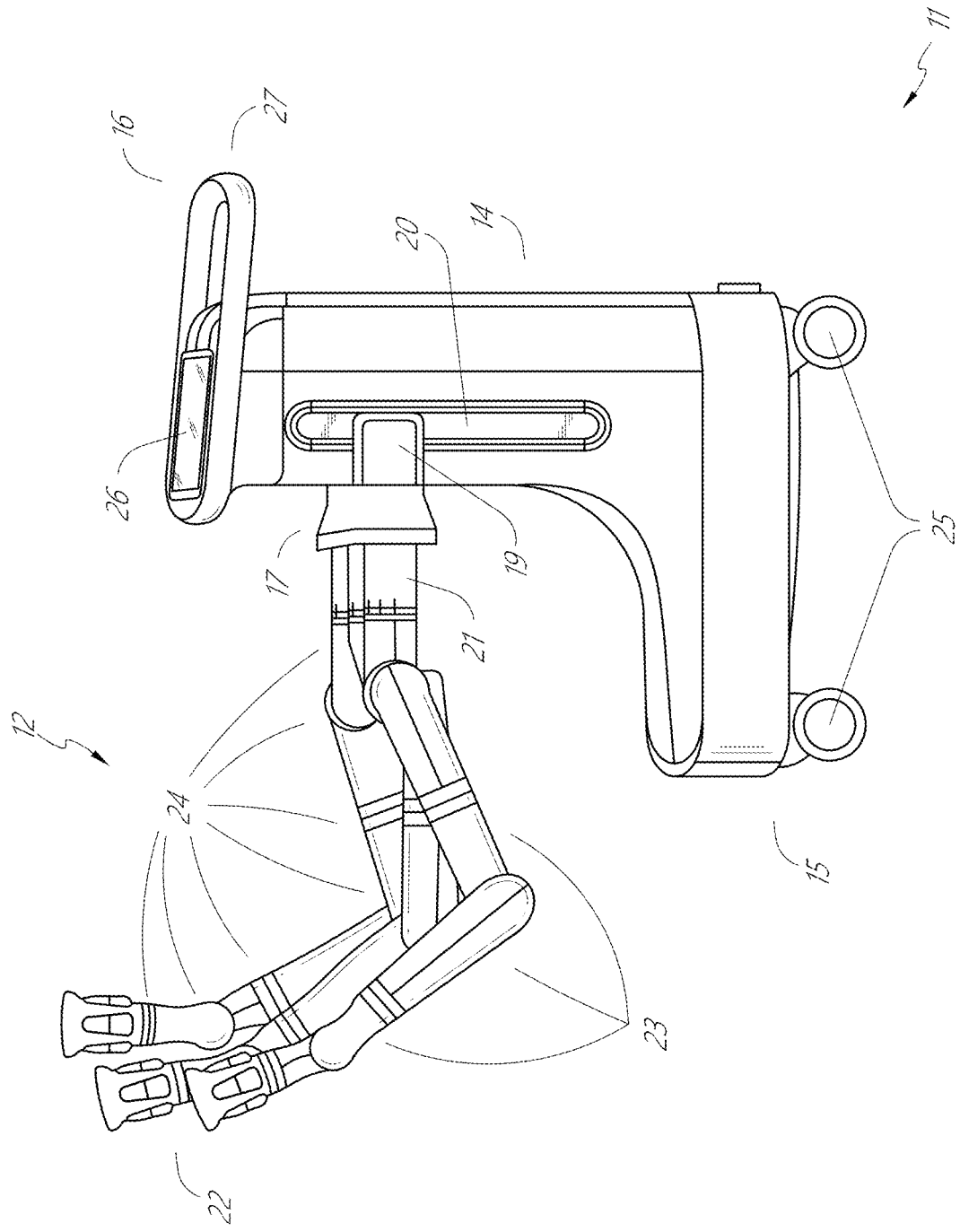
FIG. 2 depicts further aspects of the robotic system of FIG. 1.

The robotically-enabled medical system may be configured in a variety of ways depending on the particular procedure. FIG. 1 illustrates an embodiment of a cart-based robotically-enabled system 10 arranged for a diagnostic and/or therapeutic bronchoscopy. During a bronchoscopy, the system 10 may comprise a cart 11 having one or more robotic arms 12 to deliver a medical instrument, such as a steerable endoscope 13, which may be a procedure-specific bronchoscope for bronchoscopy, to a natural orifice access point (i.e., the mouth of the patient positioned on a table in the present example) to deliver diagnostic and/or therapeutic tools. As shown, the cart 11 may be positioned proximate to the patient's upper torso in order to provide access to the access point. Similarly, the robotic arms 12 may be actuated to position the bronchoscope relative to the access point. The arrangement in FIG. 1 may also be utilized when performing a gastro-intestinal (GI) procedure with a gastroscope, a specialized endoscope for GI procedures. FIG. 2 depicts an example embodiment of the cart in greater detail.

With continued reference to FIG. 1, once the cart 11 is properly positioned, the robotic arms 12 may insert the steerable endoscope 13 into the patient robotically, manually, or a combination thereof. As shown, the steerable endoscope 13 may comprise at least two telescoping parts, such as an inner leader portion and an outer sheath portion, each portion coupled to a separate instrument driver from the set of instrument drivers 28, each instrument driver coupled to the distal end of an individual robotic arm. This linear arrangement of the instrument drivers 28, which facilitates coaxially aligning the leader portion with the sheath portion, creates a "virtual rail" 29 that may be repositioned in space by manipulating the one or more robotic arms 12 into different angles and/or positions. The virtual rails described herein are depicted in the Figures using dashed lines, and accordingly the dashed lines do not depict any physical structure of the system. Translation of the instrument drivers 28 along the virtual rail 29 telescopes the inner leader portion relative to the outer sheath portion or advances or retracts the endoscope 13 from the patient. The angle of the virtual rail 29 may be adjusted, translated, and pivoted based on clinical application or physician preference. For example, in bronchoscopy, the angle and position of the virtual rail 29 as shown represents a compromise between providing physician access to the endoscope 13 while minimizing friction that results from bending the endoscope 13 into the patient's mouth.

The endoscope 13 may be directed down the patient's trachea and lungs after insertion using precise commands from the robotic system until reaching the target destination or operative site. In order to enhance navigation through the patient's lung network and/or reach the desired target, the endoscope 13 may be manipulated to telescopically extend the inner leader portion from the outer sheath portion to obtain enhanced articulation and greater bend radius. The use of separate instrument drivers 28 also allows the leader portion and sheath portion to be driven independently of each other.

For example, the endoscope 13 may be directed to deliver a biopsy needle to a target, such as, for example, a lesion or nodule within the lungs of a patient. The needle may be deployed down a working channel that runs the length of the endoscope to obtain a tissue sample to be analyzed by a pathologist. Depending on the pathology results, additional tools may be deployed down the working channel of the endoscope for additional biopsies. After identifying a nodule to be malignant, the endoscope 13 may endoscopically deliver tools to resect the potentially cancerous tissue. In some instances, diagnostic and therapeutic treatments can be delivered in separate procedures. In those circumstances, the endoscope 13 may also be used to deliver a fiducial to "mark" the location of the target nodule as well. In other instances, diagnostic and therapeutic treatments may be delivered during the same procedure.

The system 10 may also include a movable tower 30, which may be connected via support cables to the cart 11 to provide support for controls, electronics, fluidics, optics, sensors, and/or power to the cart 11. Placing such functionality in the tower 30 allows for a smaller form factor cart 11 that may be more easily adjusted and/or re-positioned by an operating physician and his/her staff. Additionally, the division of functionality between the cart/table and the support tower 30 reduces operating room clutter and facilitates improving clinical workflow. While the cart 11 may be positioned close to the patient, the tower 30 may be stowed in a remote location to stay out of the way during a procedure.

In support of the robotic systems described above, the tower 30 may include component(s) of a computer-based control system that stores computer program instructions, for example, within a non-transitory computer-readable storage medium such as a persistent magnetic storage drive, solid state drive, etc. The execution of those instructions, whether the execution occurs in the tower 30 or the cart 11, may control the entire system or sub-system(s) thereof. For example, when executed by a processor of the computer system, the instructions may cause the components of the robotics system to actuate the relevant carriages and arm mounts, actuate the robotics arms, and control the medical instruments. For example, in response to receiving the control signal, the motors in the joints of the robotics arms may position the arms into a certain posture.

The tower 30 may also include a pump, flow meter, valve control, and/or fluid access in order to provide controlled irrigation and aspiration capabilities to the system that may be deployed through the endoscope 13. These components may also be controlled using the computer system of the tower 30. In some embodiments, irrigation and aspiration capabilities may be delivered directly to the endoscope 13 through separate cable(s).

The tower 30 may include a voltage and surge protector designed to provide filtered and protected electrical power to the cart 11, thereby avoiding placement of a power transformer and other auxiliary power components in the cart 11, resulting in a smaller, more moveable cart 11.

The tower 30 may also include support equipment for the sensors deployed throughout the robotic system 10. For example, the tower 30 may include optoelectronics equipment for detecting, receiving, and processing data received from the optical sensors or cameras throughout the robotic system 10. In combination with the control system, such optoelectronics equipment may be used to generate real-time images for display in any number of consoles deployed throughout the system, including in the tower 30. Similarly, the tower 30 may also include an electronic subsystem for receiving and processing signals received from deployed electromagnetic (EM) sensors. The tower 30 may also be used to house and position an EM field generator for detection by EM sensors in or on the medical instrument.

The tower 30 may also include a console 31 in addition to other consoles available in the rest of the system, e.g., console mounted on top of the cart. The console 31 may include a user interface and a display screen, such as a touchscreen, for the physician operator. Consoles in the system 10 are generally designed to provide both robotic controls as well as preoperative and real-time information of the procedure, such as navigational and localization information of the endoscope 13. When the console 31 is not the only console available to the physician, it may be used by a second operator, such as a nurse, to monitor the health or vitals of the patient and the operation of the system 10, as well as to provide procedure-specific data, such as navigational and localization information. In other embodiments, the console 30 is housed in a body that is separate from the tower 30.

The tower 30 may be coupled to the cart 11 and endoscope 13 through one or more cables or connections (not shown). In some embodiments, the support functionality from the tower 30 may be provided through a single cable to the cart 11, simplifying and de-cluttering the operating room. In other embodiments, specific functionality may be coupled in separate cabling and connections. For example, while power may be provided through a single power cable to the cart 11, the support for controls, optics, fluidics, and/or navigation may be provided through a separate cable.

FIG. 2 provides a detailed illustration of an embodiment of the cart 11 from the cart-based robotically-enabled system shown in FIG. 1. The cart 11 generally includes an elongated support structure 14 (often referred to as a "column"), a cart base 15, and a console 16 at the top of the column 14. The column 14 may include one or more carriages, such as a carriage 17 (alternatively "arm support") for supporting the deployment of one or more robotic arms 12 (three shown in FIG. 2). The carriage 17 may include individually configurable arm mounts that rotate along a perpendicular axis to adjust the base of the robotic arms 12 for better positioning relative to the patient. The carriage 17 also includes a carriage interface 19 that allows the carriage 17 to vertically translate along the column 14.

The carriage interface 19 is connected to the column 14 through slots, such as slot 20, that are positioned on opposite sides of the column 14 to guide the vertical translation of the carriage 17. The slot 20 contains a vertical translation interface to position and hold the carriage 17 at various vertical heights relative to the cart base 15. Vertical translation of the carriage 17 allows the cart 11 to adjust the reach of the robotic arms 12 to meet a variety of table heights, patient sizes, and physician preferences. Similarly, the individually configurable arm mounts on the carriage 17 allow the robotic arm base 21 of the robotic arms 12 to be angled in a variety of configurations.

In some embodiments, the slot 20 may be supplemented with slot covers that are flush and parallel to the slot surface to prevent dirt and fluid ingress into the internal chambers of the column 14 and the vertical translation interface as the carriage 17 vertically translates. The slot covers may be deployed through pairs of spring spools positioned near the vertical top and bottom of the slot 20. The covers are coiled within the spools until deployed to extend and retract from their coiled state as the carriage 17 vertically translates up and down. The spring-loading of the spools provides force to retract the cover into a spool when the carriage 17 translates towards the spool, while also maintaining a tight seal when the carriage 17 translates away from the spool. The covers may be connected to the carriage 17 using, for example, brackets in the carriage interface 19 to ensure proper extension and retraction of the cover as the carriage 17 translates.

The column 14 may internally comprise mechanisms, such as gears and motors, that are designed to use a vertically aligned lead screw to translate the carriage 17 in a mechanized fashion in response to control signals generated in response to user inputs, e.g., inputs from the console 16.

The robotic arms 12 may generally comprise robotic arm bases 21 and end effectors 22, separated by a series of linkages 23 that are connected by a series of joints 24, each joint comprising an independent actuator, each actuator comprising an independently controllable motor. Each independently controllable joint represents an independent degree of freedom available to the robotic arm 12. Each of the robotic arms 12 may have seven joints, and thus provide seven degrees of freedom. A multitude of joints result in a multitude of degrees of freedom, allowing for "redundant" degrees of freedom. Having redundant degrees of freedom allows the robotic arms 12 to position their respective end effectors 22 at a specific position, orientation, and trajectory in space using different linkage positions and joint angles. This allows for the system to position and direct a medical instrument from a desired point in space while allowing the physician to move the arm joints into a clinically advantageous position away from the patient to create greater access, while avoiding arm collisions.

The cart base 15 balances the weight of the column 14, carriage 17, and robotic arms 12 over the floor. Accordingly, the cart base 15 houses heavier components, such as electronics, motors, power supply, as well as components that either enable movement and/or immobilize the cart 11. For example, the cart base 15 includes rollable wheel-shaped casters 25 that allow for the cart 11 to easily move around the room prior to a procedure. After reaching the appropriate position, the casters 25 may be immobilized using wheel locks to hold the cart 11 in place during the procedure.

Positioned at the vertical end of the column 14, the console 16 allows for both a user interface for receiving user input and a display screen (or a dual-purpose device such as, for example, a touchscreen 26) to provide the physician user with both preoperative and intraoperative data. Potential preoperative data on the touchscreen 26 may include preoperative plans, navigation and mapping data derived from preoperative computerized tomography (CT) scans, and/or notes from preoperative patient interviews. Intraoperative data on display may include optical information provided from the tool, sensor and coordinate information from sensors, as well as vital patient statistics, such as respiration, heart rate, and/or pulse. The console 16 may be positioned and tilted to allow a physician to access the console 16 from the side of the column 14 opposite the carriage 17. From this position, the physician may view the console 16, robotic arms 12, and patient while operating the console 16 from behind the cart 11. As shown, the console 16 also includes a handle 27 to assist with maneuvering and stabilizing the cart 11.

Figure 3:
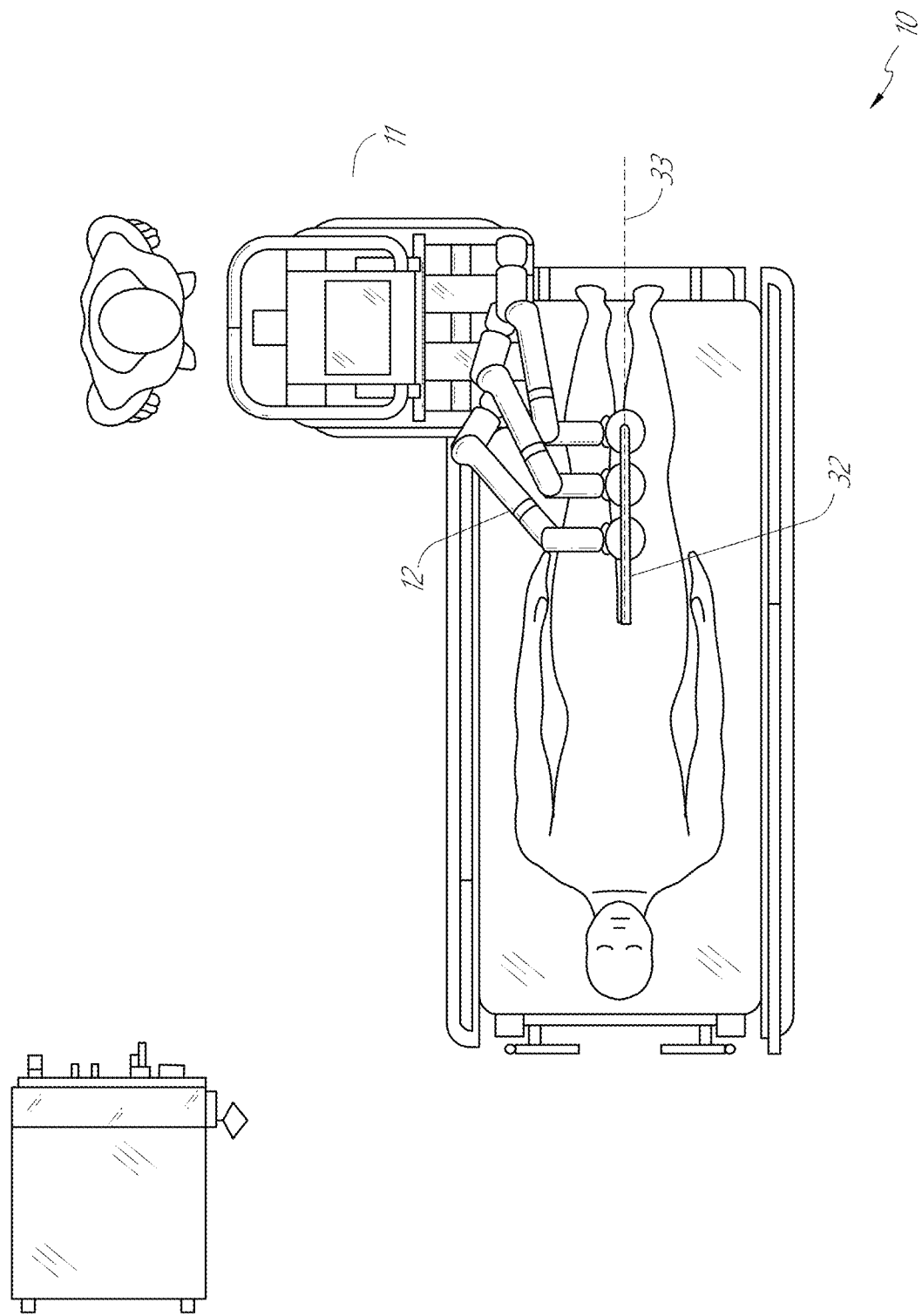
FIG. 3 illustrates an embodiment of the robotic system of FIG. 1 arranged for ureteroscopy.

FIG. 3 illustrates an embodiment of a robotically-enabled system 10 arranged for ureteroscopy. In a ureteroscopic procedure, the cart 11 may be positioned to deliver a ureteroscope 32, a procedure-specific endoscope designed to traverse a patient's urethra and ureter, to the lower abdominal area of the patient. In a ureteroscopy, it may be desirable for the ureteroscope 32 to be directly aligned with the patient's urethra to reduce friction and forces on the sensitive anatomy in the area. As shown, the cart 11 may be aligned at the foot of the table to allow the robotic arms 12 to position the ureteroscope 32 for direct linear access to the patient's urethra. From the foot of the table, the robotic arms 12 may insert the ureteroscope 32 along the virtual rail 33 directly into the patient's lower abdomen through the urethra.

After insertion into the urethra, using similar control techniques as in bronchoscopy, the ureteroscope 32 may be navigated into the bladder, ureters, and/or kidneys for diagnostic and/or therapeutic applications. For example, the ureteroscope 32 may be directed into the ureter and kidneys to break up kidney stone build up using a laser or ultrasonic lithotripsy device deployed down the working channel of the ureteroscope 32. After lithotripsy is complete, the resulting stone fragments may be removed using baskets deployed down the ureteroscope 32.

Figure 4:
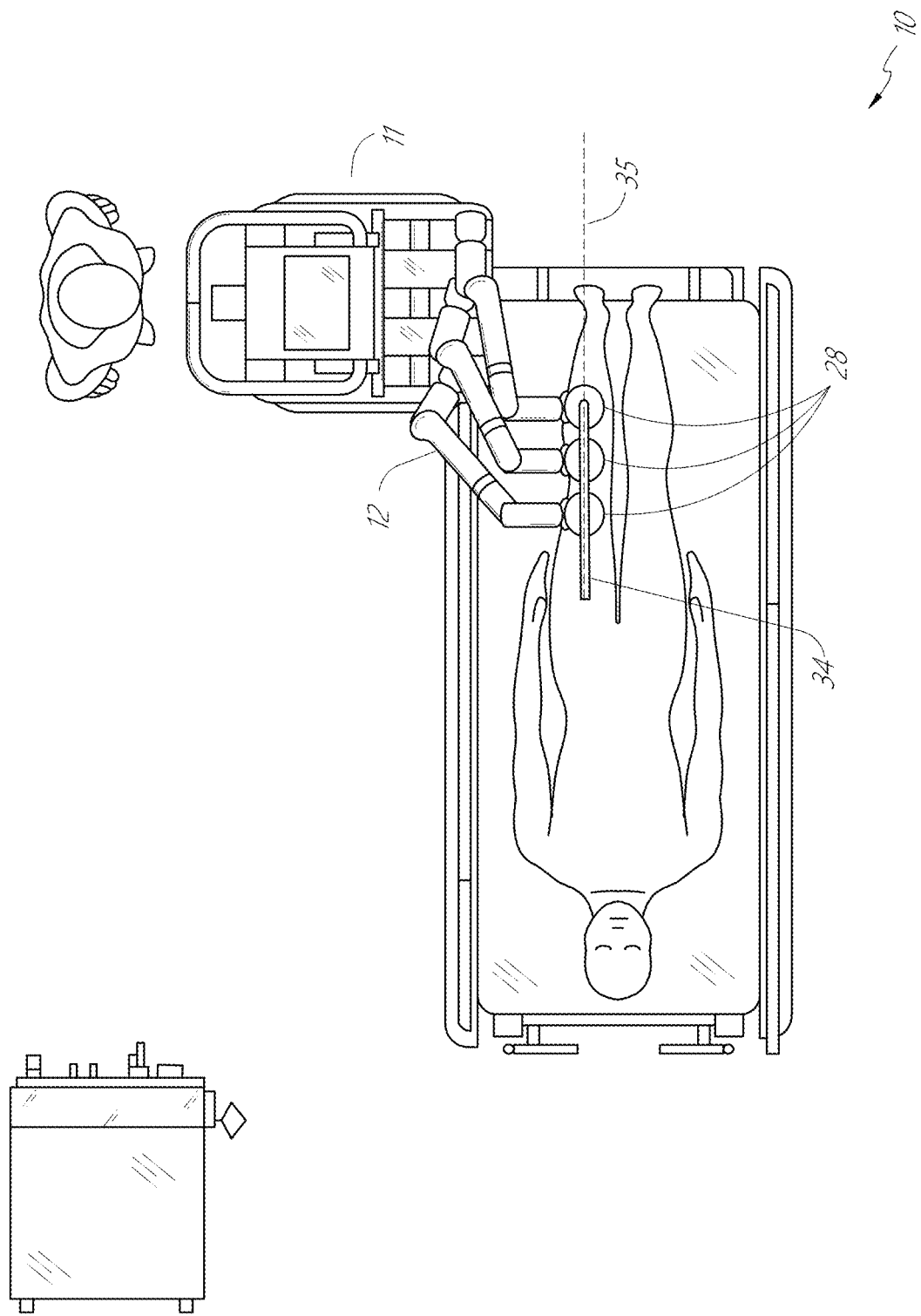
FIG. 4 illustrates an embodiment of the robotic system of FIG. 1 arranged for a vascular procedure.

FIG. 4 illustrates an embodiment of a robotically-enabled system 10 similarly arranged for a vascular procedure. In a vascular procedure, the system 10 may be configured such that the cart 11 may deliver a medical instrument 34, such as a steerable catheter, to an access point in the femoral artery in the patient's leg. The femoral artery presents both a larger diameter for navigation as well as a relatively less circuitous and tortuous path to the patient's heart, which simplifies navigation. As in a ureteroscopic procedure, the cart 11 may be positioned towards the patient's legs and lower abdomen to allow the robotic arms 12 to provide a virtual rail 35 with direct linear access to the femoral artery access point in the patient's thigh/hip region. After insertion into the artery, the medical instrument 34 may be directed and inserted by translating the instrument drivers 28. Alternatively, the cart may be positioned around the patient's upper abdomen in order to reach alternative vascular access points, such as, for example, the carotid and brachial arteries near the shoulder and wrist.

B. Robotic System—Table.

Figure 5:
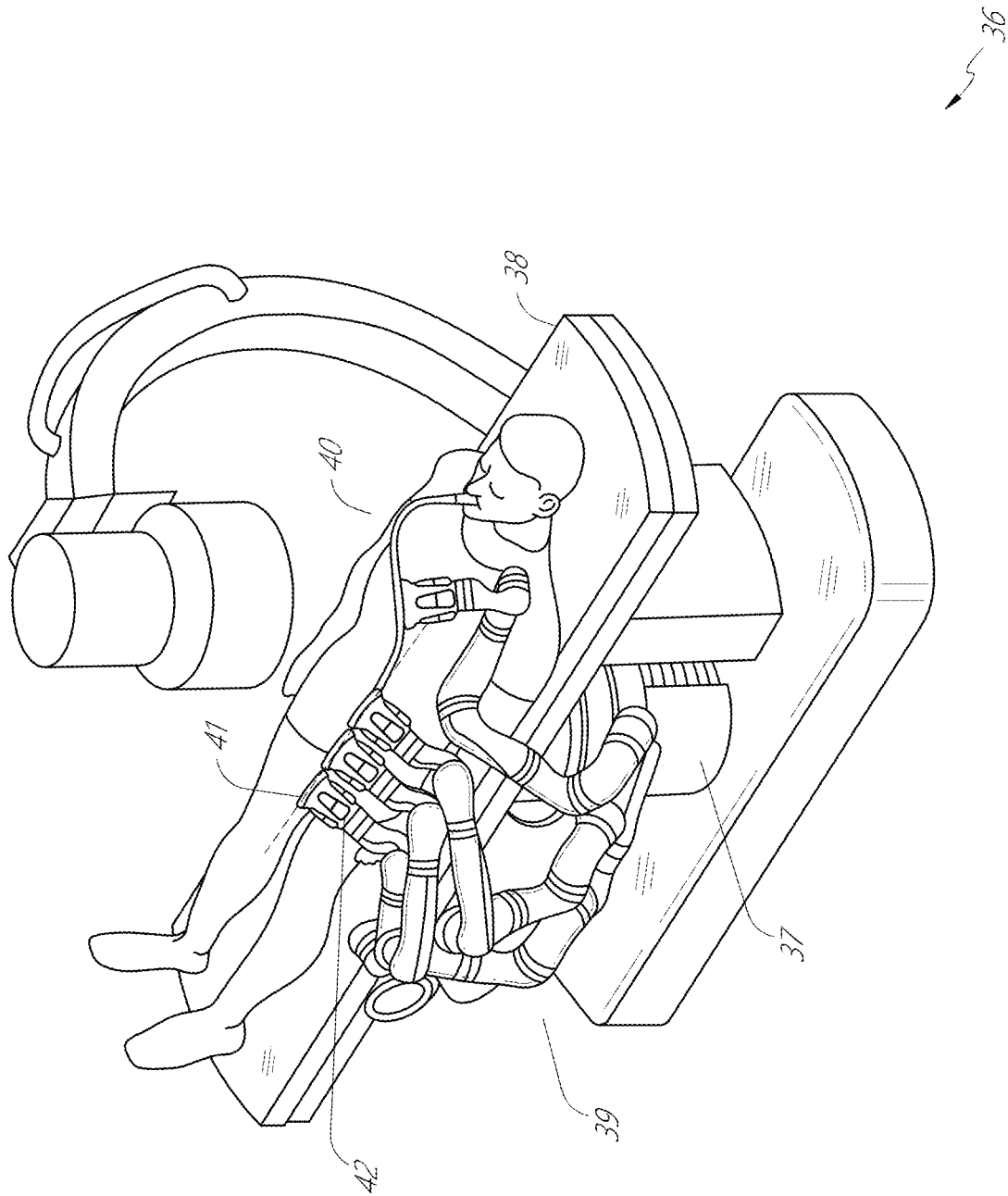
FIG. 5 illustrates an embodiment of a table-based robotic system arranged for a bronchoscopic procedure.

Embodiments of the robotically-enabled medical system may also incorporate the patient's table. Incorporation of the table reduces the amount of capital equipment within the operating room by removing the cart, which allows greater access to the patient. FIG. 5 illustrates an embodiment of such a robotically-enabled system arranged for a bronchoscopic procedure. System 36 includes a support structure or column 37 for supporting platform 38 (shown as a "table" or "bed") over the floor. Much like in the cart-based systems, the end effectors of the robotic arms 39 of the system 36 comprise instrument drivers 42 that are designed to manipulate an elongated medical instrument, such as a bronchoscope 40 in FIG. 5, through or along a virtual rail 41 formed from the linear alignment of the instrument drivers 42. In practice, a C-arm for providing fluoroscopic imaging may be positioned over the patient's upper abdominal area by placing the emitter and detector around the table 38.

Figure 6:
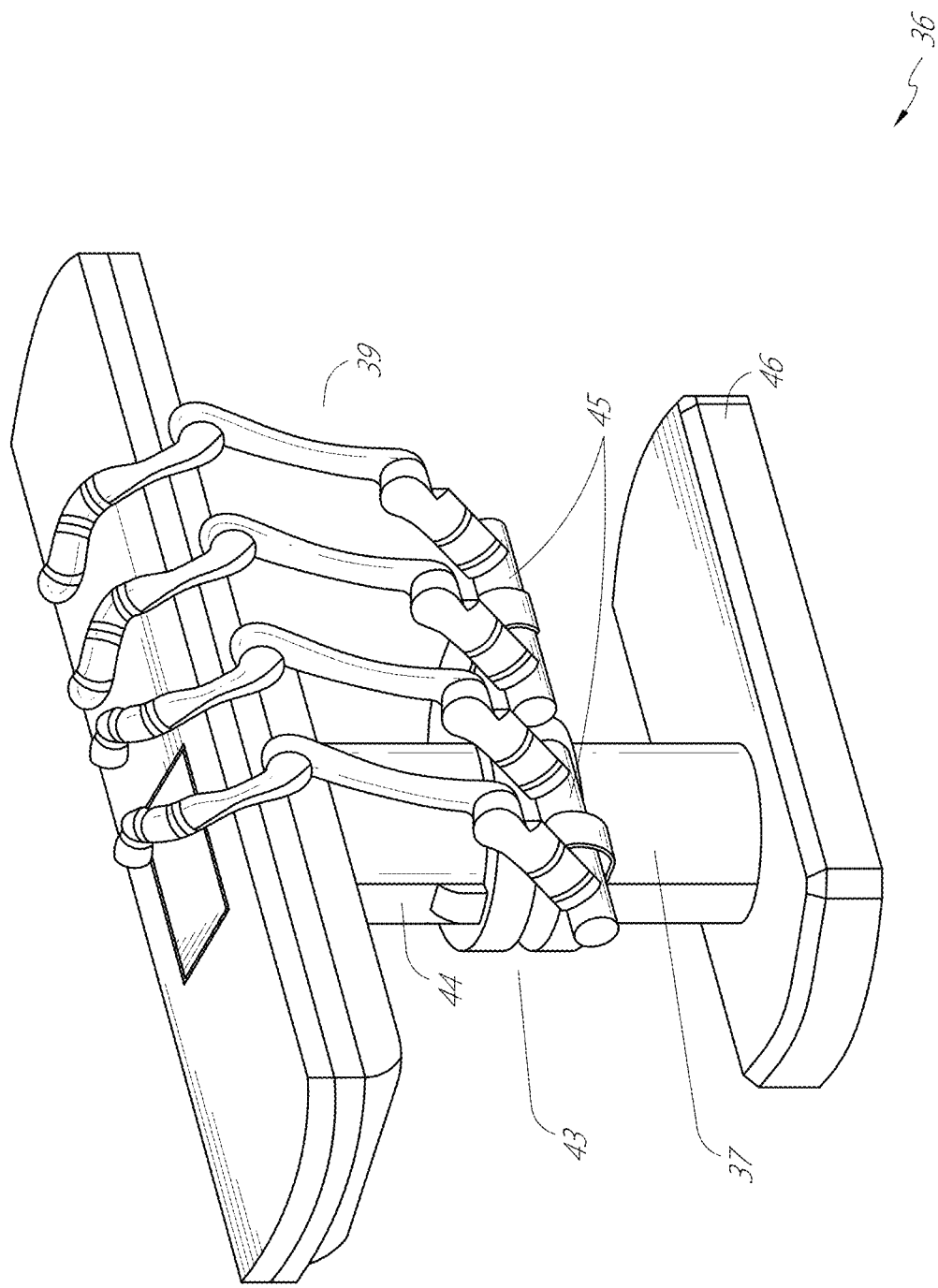
FIG. 6 provides an alternative view of the robotic system of FIG. 5.

FIG. 6 provides an alternative view of the system 36 without the patient and medical instrument for discussion purposes. As shown, the column 37 may include one or more carriages 43 shown as ring-shaped in the system 36, from which the one or more robotic arms 39 may be based. The carriages 43 may translate along a vertical column interface 44 that runs the length of the column 37 to provide different vantage points from which the robotic arms 39 may be positioned to reach the patient. The carriage(s) 43 may rotate around the column 37 using a mechanical motor positioned within the column 37 to allow the robotic arms 39 to have access to multiples sides of the table 38, such as, for example, both sides of the patient. In embodiments with multiple carriages, the carriages may be individually positioned on the column and may translate and/or rotate independently of the other carriages. While the carriages 43 need not surround the column 37 or even be circular, the ring-shape as shown facilitates rotation of the carriages 43 around the column 37 while maintaining structural balance. Rotation and translation of the carriages 43 allows the system 36 to align the medical instruments, such as endoscopes and laparoscopes, into different access points on the patient. In other embodiments (not shown), the system 36 can include a patient table or bed with adjustable arm supports in the form of bars or rails extending alongside it. One or more robotic arms 39 (e.g., via a shoulder with an elbow joint) can be attached to the adjustable arm supports, which can be vertically adjusted. By providing vertical adjustment, the robotic arms 39 are advantageously capable of being stowed compactly beneath the patient table or bed, and subsequently raised during a procedure.

Figure 9:
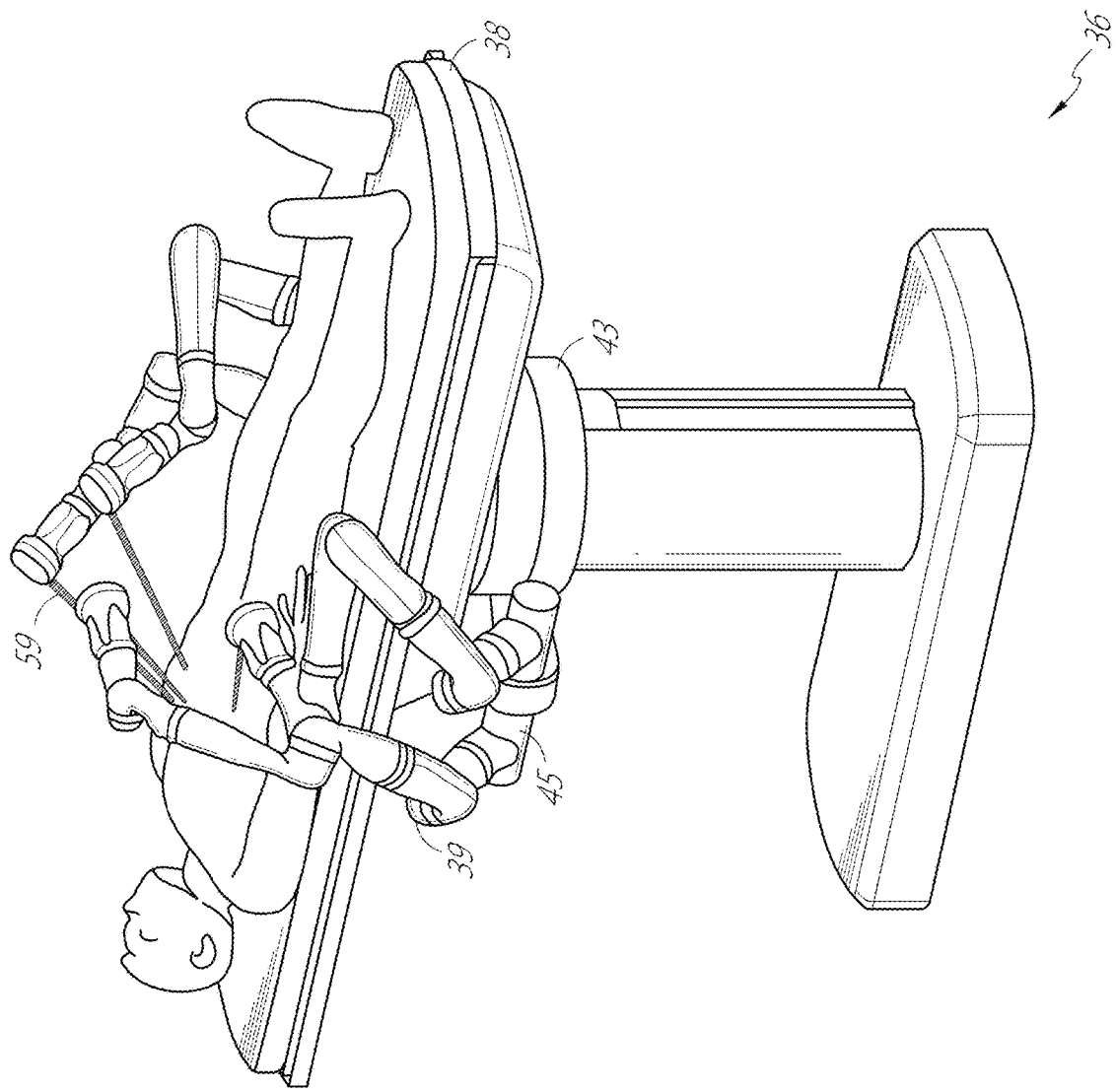
FIG. 9 illustrates an embodiment of a table-based robotic system configured for a laparoscopic procedure.

The robotic arms 39 may be mounted on the carriages 43 through a set of arm mounts 45 comprising a series of joints that may individually rotate and/or telescopically extend to provide additional configurability to the robotic arms 39. Additionally, the arm mounts 45 may be positioned on the carriages 43 such that, when the carriages 43 are appropriately rotated, the arm mounts 45 may be positioned on either the same side of the table 38 (as shown in FIG. 6), on opposite sides of the table 38 (as shown in FIG. 9), or on adjacent sides of the table 38 (not shown).

The column 37 structurally provides support for the table 38, and a path for vertical translation of the carriages 43. Internally, the column 37 may be equipped with lead screws for guiding vertical translation of the carriages, and motors to mechanize the translation of the carriages 43 based the lead screws. The column 37 may also convey power and control signals to the carriages 43 and the robotic arms 39 mounted thereon.

The table base 46 serves a similar function as the cart base 15 in the cart 11 shown in FIG. 2, housing heavier components to balance the table/bed 38, the column 37, the carriages 43, and the robotic arms 39. The table base 46 may also incorporate rigid casters to provide stability during procedures. Deployed from the bottom of the table base 46, the casters may extend in opposite directions on both sides of the base 46 and retract when the system 36 needs to be moved.

With continued reference to FIG. 6, the system 36 may also include a tower (not shown) that divides the functionality of the system 36 between the table and the tower to reduce the form factor and bulk of the table. As in earlier disclosed embodiments, the tower may provide a variety of support functionalities to the table, such as processing, computing, and control capabilities, power, fluidics, and/or optical and sensor processing. The tower may also be movable to be positioned away from the patient to improve physician access and de-clutter the operating room. Additionally, placing components in the tower allows for more storage space in the table base 46 for potential stowage of the robotic arms 39. The tower may also include a master controller or console that provides both a user interface for user input, such as keyboard and/or pendant, as well as a display screen (or touchscreen) for preoperative and intraoperative information, such as real-time imaging, navigation, and tracking information. In some embodiments, the tower may also contain holders for gas tanks to be used for insufflation.

Figure 7:
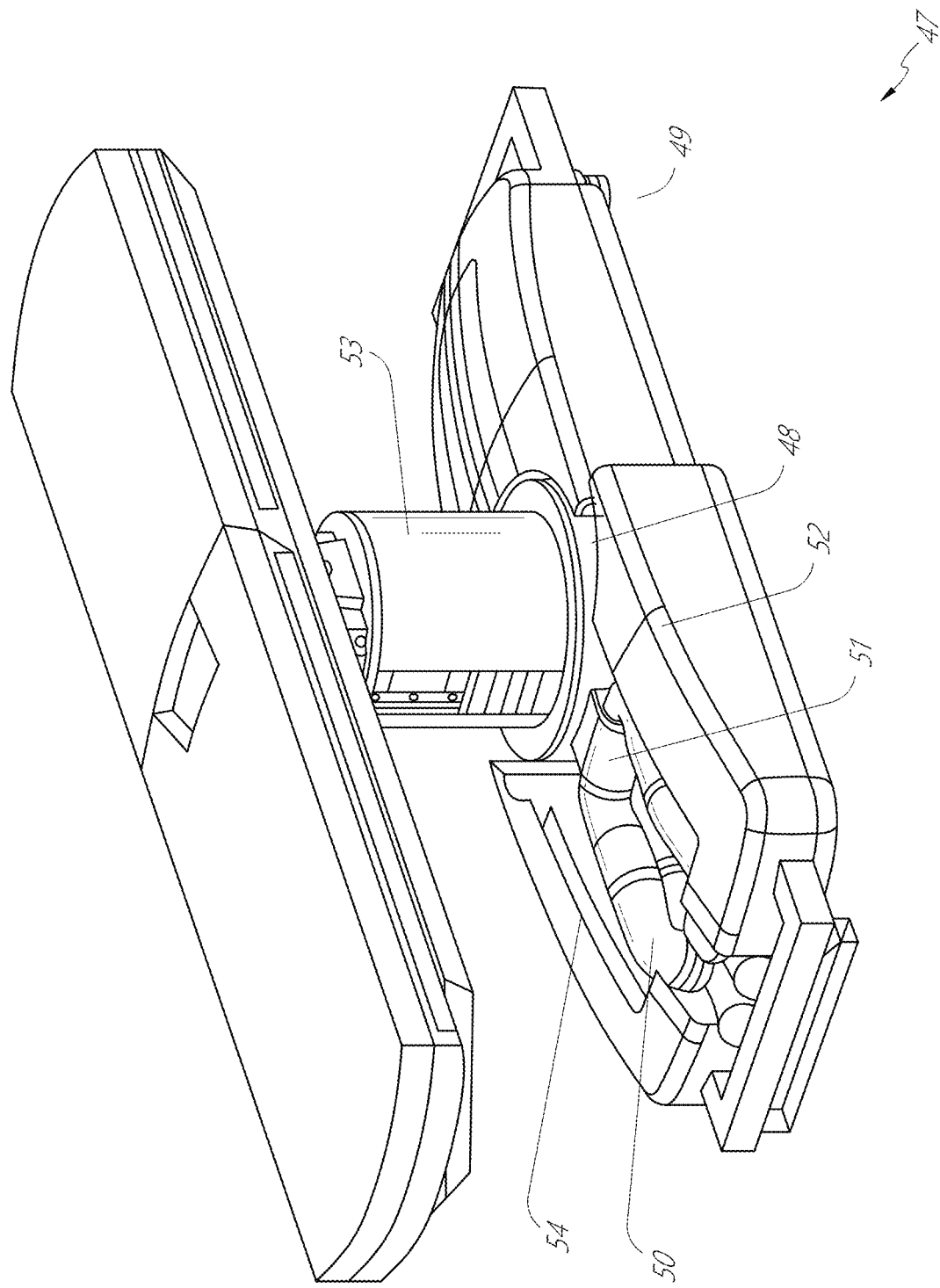
FIG. 7 illustrates an example system configured to stow robotic arm(s).

In some embodiments, a table base may stow and store the robotic arms when not in use. FIG. 7 illustrates a system 47 that stows robotic arms in an embodiment of the table-based system. In the system 47, carriages 48 may be vertically translated into base 49 to stow robotic arms 50, arm mounts 51, and the carriages 48 within the base 49. Base covers 52 may be translated and retracted open to deploy the carriages 48, arm mounts 51, and robotic arms 50 around column 53, and closed to stow to protect them when not in use. The base covers 52 may be sealed with a membrane 54 along the edges of its opening to prevent dirt and fluid ingress when closed.

Figure 8:
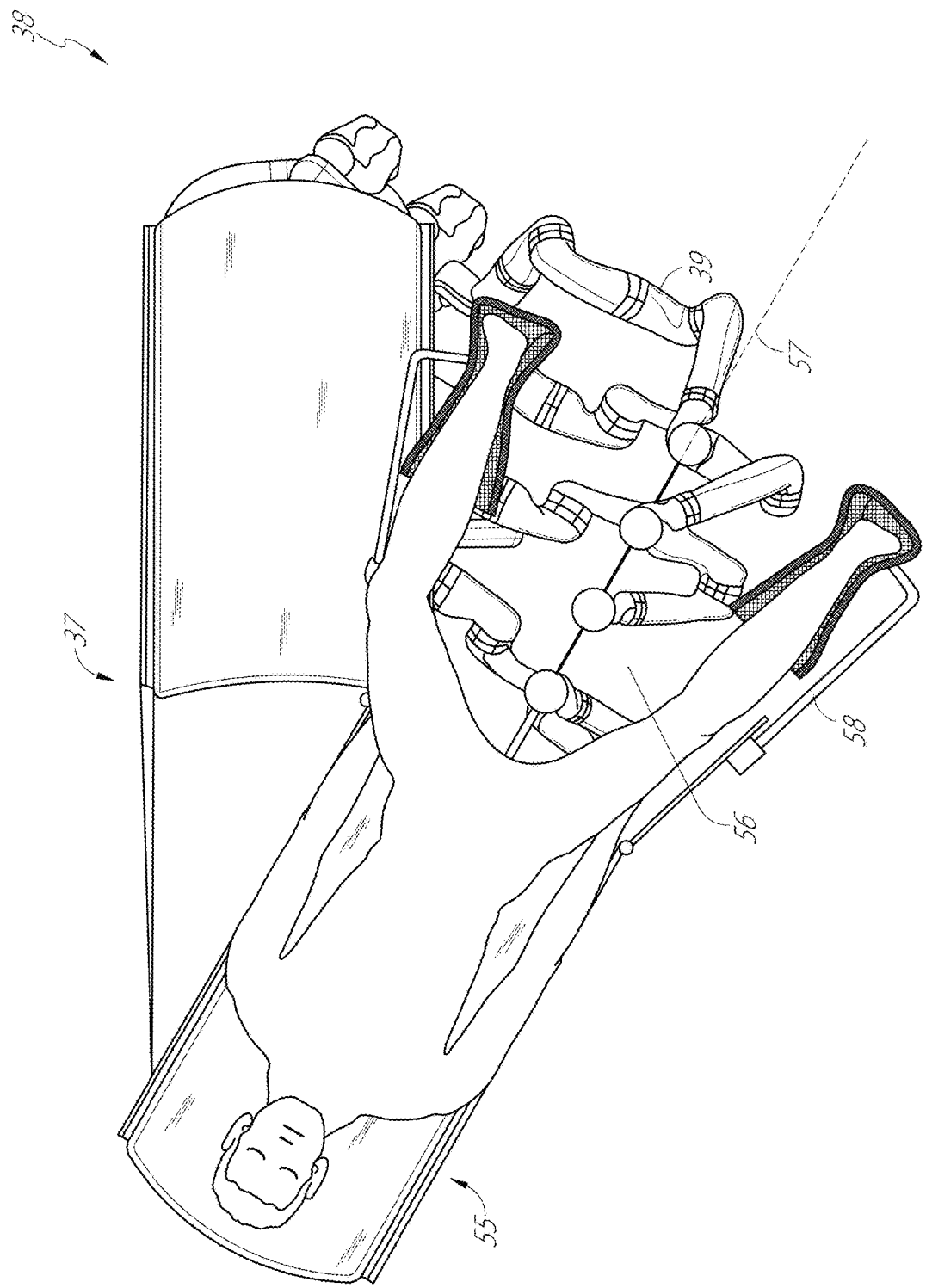
FIG. 8 illustrates an embodiment of a table-based robotic system configured for a ureteroscopic procedure.

FIG. 8 illustrates an embodiment of a robotically-enabled table-based system configured for a ureteroscopic procedure. In a ureteroscopy, the table 38 may include a swivel portion 55 for positioning a patient off-angle from the column 37 and table base 46. The swivel portion 55 may rotate or pivot around a pivot point (e.g., located below the patient's head) in order to position the bottom portion of the swivel portion 55 away from the column 37. For example, the pivoting of the swivel portion 55 allows a C-arm (not shown) to be positioned over the patient's lower abdomen without competing for space with the column (not shown) below table 38. By rotating the carriage 35 (not shown) around the column 37, the robotic arms 39 may directly insert a ureteroscope 56 along a virtual rail 57 into the patient's groin area to reach the urethra. In a ureteroscopy, stirrups 58 may also be fixed to the swivel portion 55 of the table 38 to support the position of the patient's legs during the procedure and allow clear access to the patient's groin area.

In a laparoscopic procedure, through small incision(s) in the patient's abdominal wall, minimally invasive instruments may be inserted into the patient's anatomy. In some embodiments, the minimally invasive instruments comprise an elongated rigid member, such as a shaft, which is used to access anatomy within the patient. After inflation of the patient's abdominal cavity, the instruments may be directed to perform surgical or medical tasks, such as grasping, cutting, ablating, suturing, etc. In some embodiments, the instruments can comprise a scope, such as a laparoscope. FIG. 9 illustrates an embodiment of a robotically-enabled table-based system configured for a laparoscopic procedure. As shown in FIG. 9, the carriages 43 of the system 36 may be rotated and vertically adjusted to position pairs of the robotic arms 39 on opposite sides of the table 38, such that instrument 59 may be positioned using the arm mounts 45 to be passed through minimal incisions on both sides of the patient to reach his/her abdominal cavity.

Figure 10:
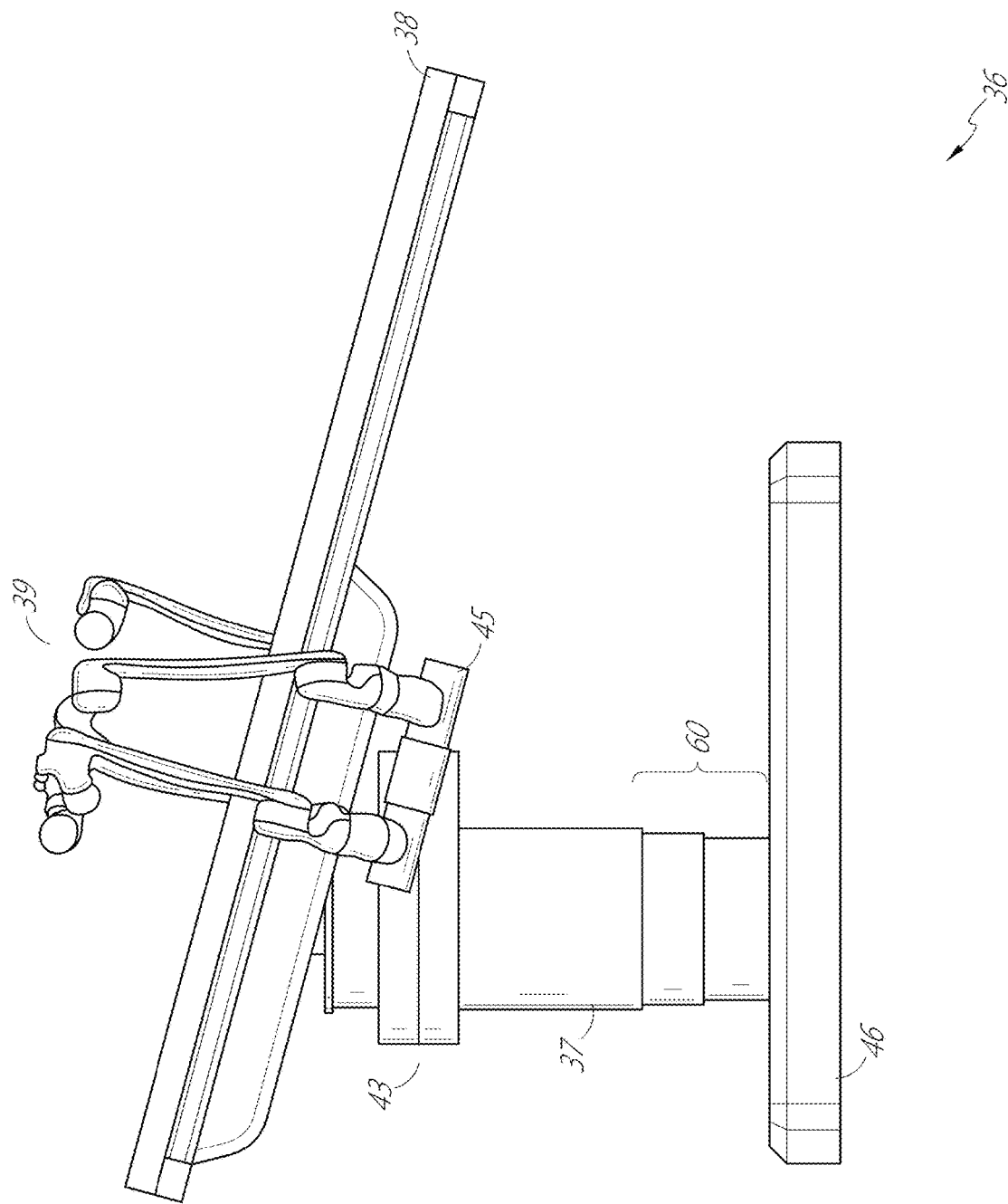
FIG. 10 illustrates an embodiment of the table-based robotic system of FIGS. 5-9 with pitch or tilt adjustment.

To accommodate laparoscopic procedures, the robotically-enabled table system may also tilt the platform to a desired angle. FIG. 10 illustrates an embodiment of the robotically-enabled medical system with pitch or tilt adjustment. As shown in FIG. 10, the system 36 may accommodate tilt of the table 38 to position one portion of the table at a greater distance from the floor than the other. Additionally, the arm mounts 45 may rotate to match the tilt such that the robotic arms 39 maintain the same planar relationship with the table 38. To accommodate steeper angles, the column 37 may also include telescoping portions 60 that allow vertical extension of the column 37 to keep the table 38 from touching the floor or colliding with the table base 46.

Figure 11:
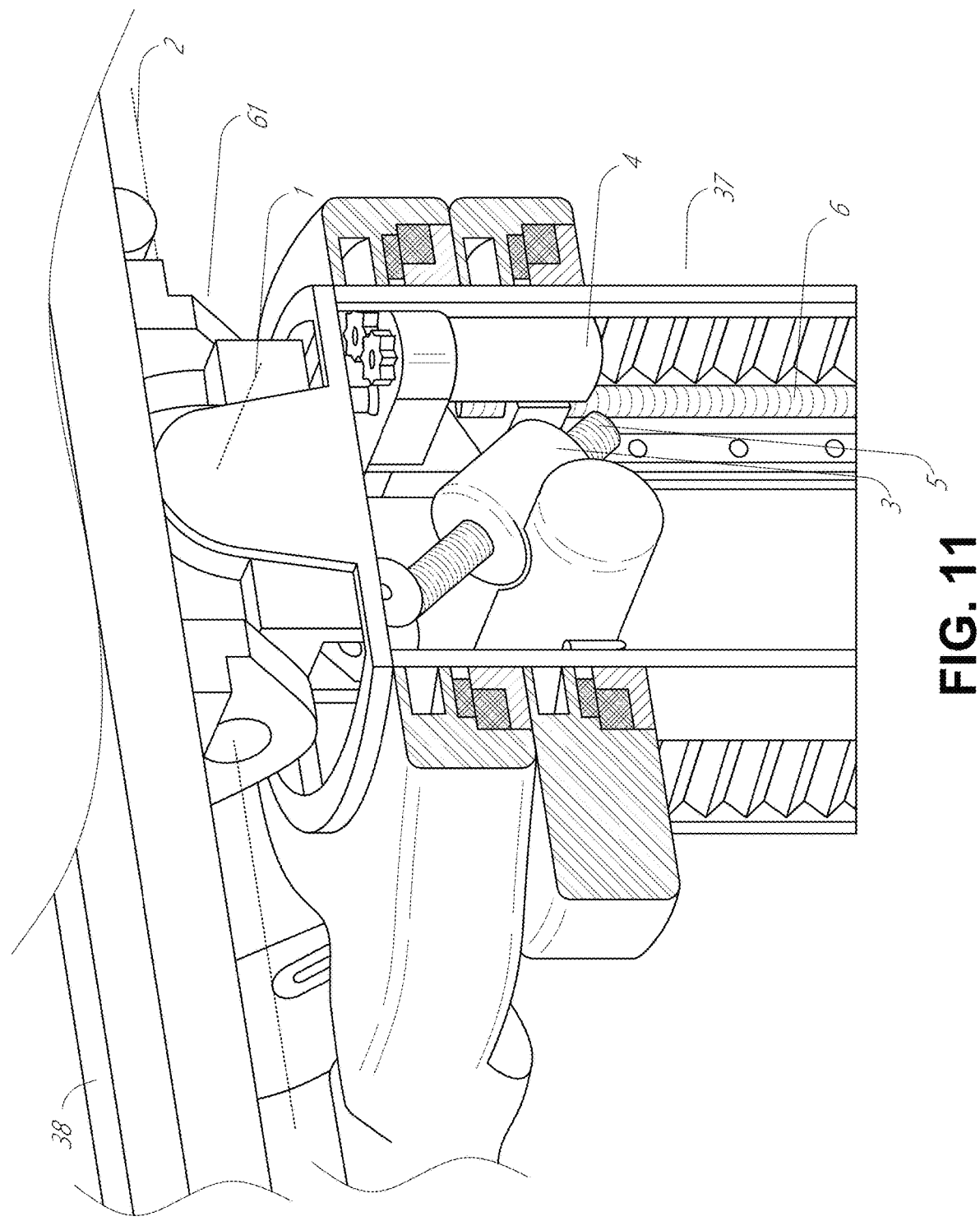
FIG. 11 provides a detailed illustration of the interface between the table and the column of the table-based robotic system of FIGS. 5-10.

FIG. 11 provides a detailed illustration of the interface between the table 38 and the column 37. Pitch rotation mechanism 61 may be configured to alter the pitch angle of the table 38 relative to the column 37 in multiple degrees of freedom. The pitch rotation mechanism 61 may be enabled by the positioning of orthogonal axes 1, 2 at the column-table interface, each axis actuated by a separate motor 3, 4 responsive to an electrical pitch angle command. Rotation along one screw 5 would enable tilt adjustments in one axis 1, while rotation along the other screw 6 would enable tilt adjustments along the other axis 2. In some embodiments, a ball joint can be used to alter the pitch angle of the table 38 relative to the column 37 in multiple degrees of freedom.

For example, pitch adjustments are particularly useful when trying to position the table in a Trendelenburg position, i.e., position the patient's lower abdomen at a higher position from the floor than the patient's upper abdomen, for lower abdominal surgery. The Trendelenburg position causes the patient's internal organs to slide towards his/her upper abdomen through the force of gravity, clearing out the abdominal cavity for minimally invasive tools to enter and perform lower abdominal surgical or medical procedures, such as laparoscopic prostatectomy.

Figure 12:
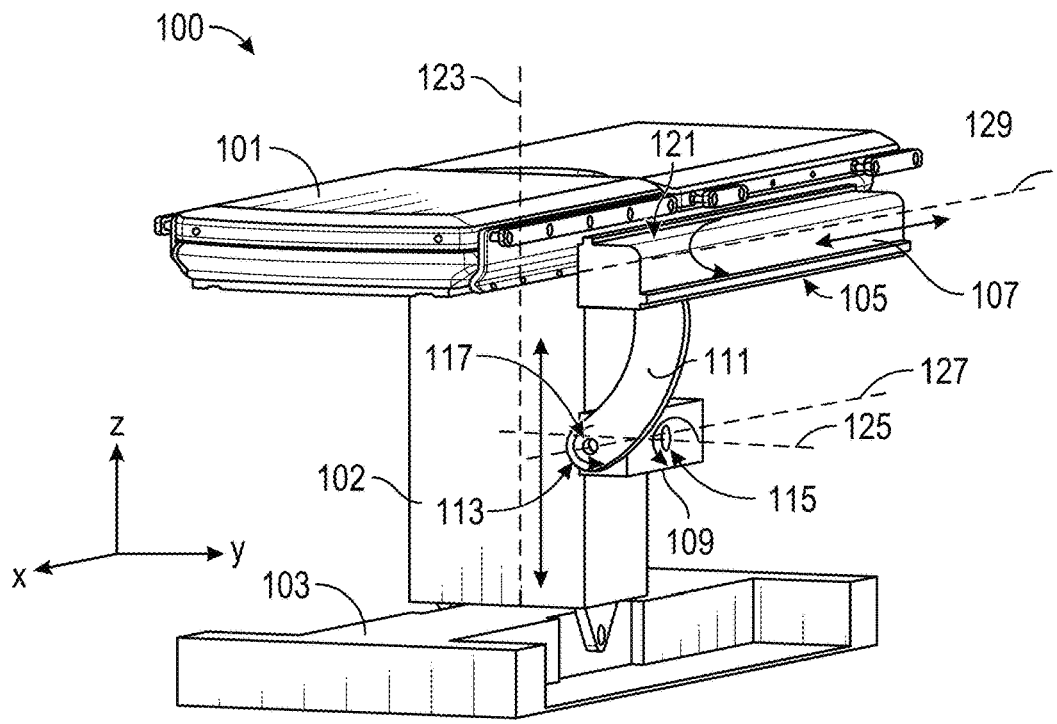
FIG. 12 illustrates an alternative embodiment of a table-based robotic system.
Figure 13:
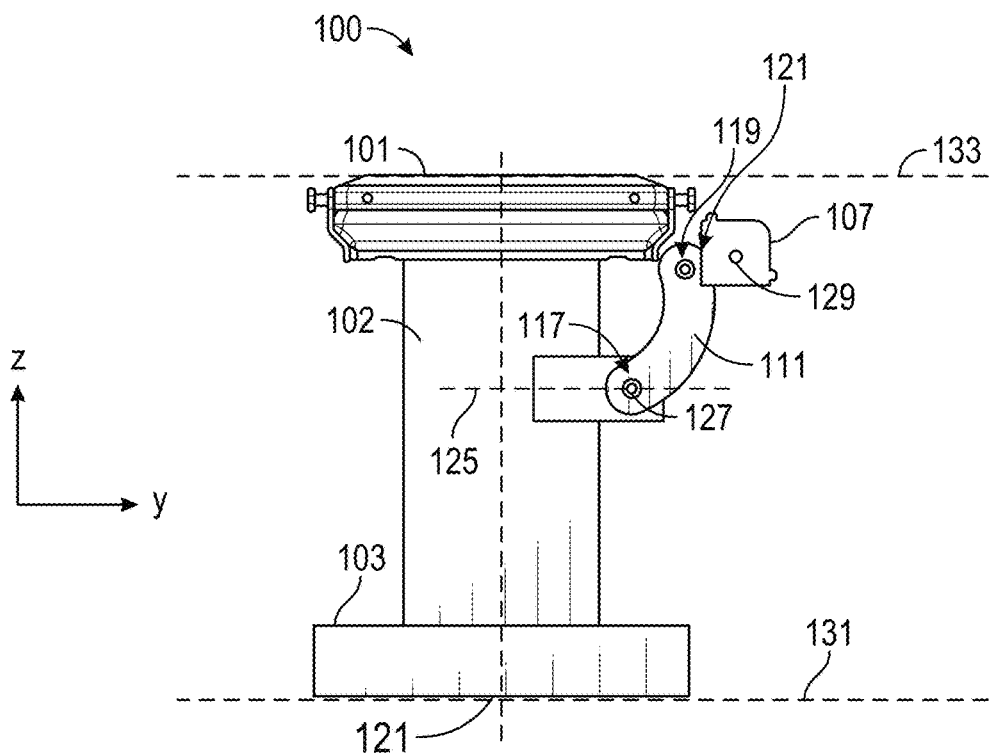
FIG. 13 illustrates an end view of the table-based robotic system of FIG. 12.

FIGS. 12 and 13 illustrate isometric and end views of an alternative embodiment of a table-based surgical robotics system 100. The surgical robotics system 100 includes one or more adjustable arm supports 105 that can be configured to support one or more robotic arms (see, for example, FIG. 14) relative to a table 101. In the illustrated embodiment, a single adjustable arm support 105 is shown, though an additional arm support can be provided on an opposite side of the table 101. The adjustable arm support 105 can be configured so that it can move relative to the table 101 to adjust and/or vary the position of the adjustable arm support 105 and/or any robotic arms mounted thereto relative to the table 101. For example, the adjustable arm support 105 may be adjusted one or more degrees of freedom relative to the table 101. The adjustable arm support 105 provides high versatility to the system 100, including the ability to easily stow the one or more adjustable arm supports 105 and any robotics arms attached thereto beneath the table 101. The adjustable arm support 105 can be elevated from the stowed position to a position below an upper surface of the table 101. In other embodiments, the adjustable arm support 105 can be elevated from the stowed position to a position above an upper surface of the table 101.

The adjustable arm support 105 can provide several degrees of freedom, including lift, lateral translation, tilt, etc. In the illustrated embodiment of FIGS. 12 and 13, the arm support 105 is configured with four degrees of freedom, which are illustrated with arrows in FIG. 12. A first degree of freedom allows for adjustment of the adjustable arm support 105 in the z-direction ("Z-lift"). For example, the adjustable arm support 105 can include a carriage 109 configured to move up or down along or relative to a column 102 supporting the table 101. A second degree of freedom can allow the adjustable arm support 105 to tilt. For example, the adjustable arm support 105 can include a rotary joint, which can allow the adjustable arm support 105 to be aligned with the bed in a Trendelenburg position. A third degree of freedom can allow the adjustable arm support 105 to "pivot up," which can be used to adjust a distance between a side of the table 101 and the adjustable arm support 105. A fourth degree of freedom can permit translation of the adjustable arm support 105 along a longitudinal length of the table.

The surgical robotics system 100 in FIGS. 12 and 13 can comprise a table supported by a column 102 that is mounted to a base 103. The base 103 and the column 102 support the table 101 relative to a support surface. A floor axis 131 and a support axis 133 are shown in FIG. 13.

The adjustable arm support 105 can be mounted to the column 102. In other embodiments, the arm support 105 can be mounted to the table 101 or base 103. The adjustable arm support 105 can include a carriage 109, a bar or rail connector 111 and a bar or rail 107. In some embodiments, one or more robotic arms mounted to the rail 107 can translate and move relative to one another.

The carriage 109 can be attached to the column 102 by a first joint 113, which allows the carriage 109 to move relative to the column 102 (e.g., such as up and down a first or vertical axis 123). The first joint 113 can provide the first degree of freedom ("Z-lift") to the adjustable arm support 105. The adjustable arm support 105 can include a second joint 115, which provides the second degree of freedom (tilt) for the adjustable arm support 105. The adjustable arm support 105 can include a third joint 117, which can provide the third degree of freedom ("pivot up") for the adjustable arm support 105. An additional joint 119 (shown in FIG. 13) can be provided that mechanically constrains the third joint 117 to maintain an orientation of the rail 107 as the rail connector 111 is rotated about a third axis 127. The adjustable arm support 105 can include a fourth joint 121, which can provide a fourth degree of freedom (translation) for the adjustable arm support 105 along a fourth axis 129.

Figure 14:
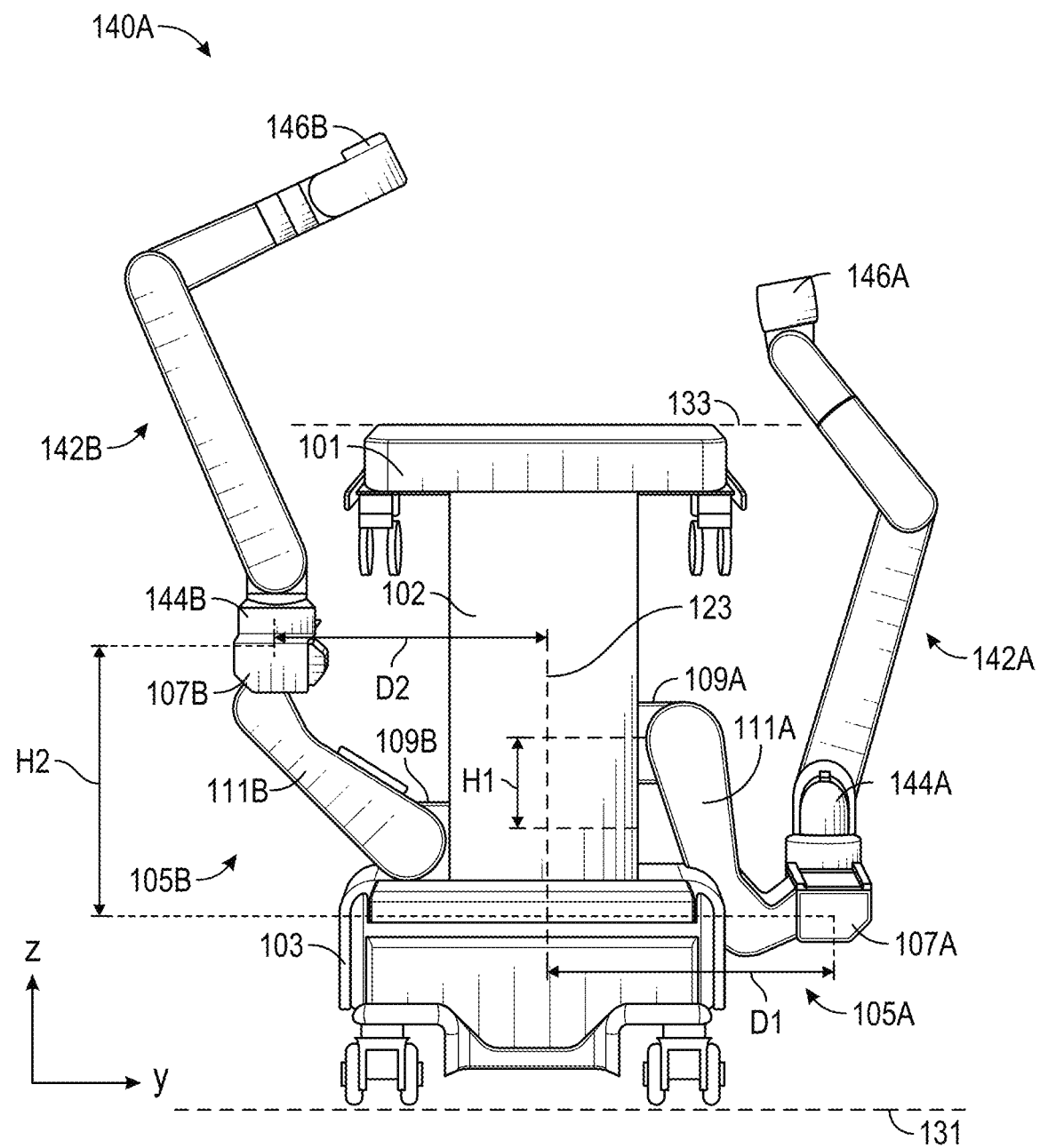
FIG. 14 illustrates an end view of a table-based robotic system with robotic arms attached thereto.

FIG. 14 illustrates an end view of the surgical robotics system 140A with two adjustable arm supports 105A, 105B mounted on opposite sides of a table 101. A first robotic arm 142A is attached to the bar or rail 107A of the first adjustable arm support 105B. The first robotic arm 142A includes a base 144A attached to the rail 107A. The distal end of the first robotic arm 142A includes an instrument drive mechanism 146A that can attach to one or more robotic medical instruments or tools. Similarly, the second robotic arm 142B includes a base 144B attached to the rail 107B. The distal end of the second robotic arm 142B includes an instrument drive mechanism 146B. The instrument drive mechanism 146B can be configured to attach to one or more robotic medical instruments or tools.

In some embodiments, one or more of the robotic arms 142A, 142B comprises an arm with seven or more degrees of freedom. In some embodiments, one or more of the robotic arms 142A, 142B can include eight degrees of freedom, including an insertion axis (1-degree of freedom including insertion), a wrist (3-degrees of freedom including wrist pitch, yaw and roll), an elbow (1-degree of freedom including elbow pitch), a shoulder (2-degrees of freedom including shoulder pitch and yaw), and base 144A, 144B (1-degree of freedom including translation). In some embodiments, the insertion degree of freedom can be provided by the robotic arm 142A, 142B, while in other embodiments, the instrument itself provides insertion via an instrument-based insertion architecture.

C. Instrument Driver & Interface.

The end effectors of the system's robotic arms may comprise (i) an instrument driver (alternatively referred to as "instrument drive mechanism" or "instrument device manipulator") that incorporates electro-mechanical means for actuating the medical instrument and (ii) a removable or detachable medical instrument, which may be devoid of any electro-mechanical components, such as motors. This dichotomy may be driven by the need to sterilize medical instruments used in medical procedures, and the inability to adequately sterilize expensive capital equipment due to their intricate mechanical assemblies and sensitive electronics. Accordingly, the medical instruments may be designed to be detached, removed, and interchanged from the instrument driver (and thus the system) for individual sterilization or disposal by the physician or the physician's staff. In contrast, the instrument drivers need not be changed or sterilized, and may be draped for protection.

Figure 15:
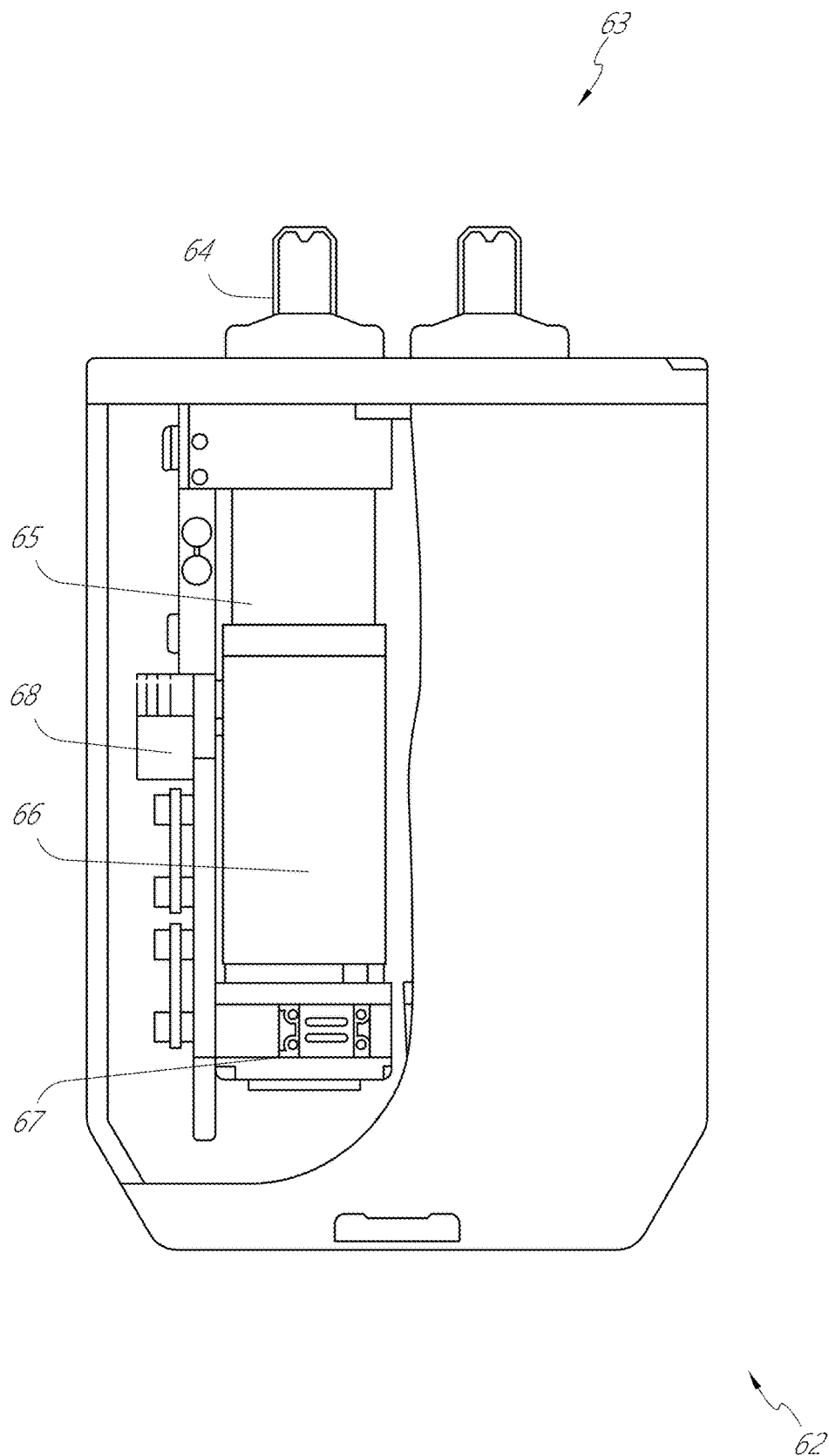
FIG. 15 illustrates an exemplary instrument driver.

FIG. 15 illustrates an example instrument driver. Positioned at the distal end of a robotic arm, instrument driver 62 comprises one or more drive units 63 arranged with parallel axes to provide controlled torque to a medical instrument via drive shafts 64. Each drive unit 63 comprises an individual drive shaft 64 for interacting with the instrument, a gear head 65 for converting the motor shaft rotation to a desired torque, a motor 66 for generating the drive torque, an encoder 67 to measure the speed of the motor shaft and provide feedback to the control circuitry, and control circuitry 68 for receiving control signals and actuating the drive unit. Each drive unit 63 being independently controlled and motorized, the instrument driver 62 may provide multiple (e.g., four as shown in FIG. 15) independent drive outputs to the medical instrument. In operation, the control circuitry 68 would receive a control signal, transmit a motor signal to the motor 66, compare the resulting motor speed as measured by the encoder 67 with the desired speed, and modulate the motor signal to generate the desired torque.

For procedures that require a sterile environment, the robotic system may incorporate a drive interface, such as a sterile adapter connected to a sterile drape, that sits between the instrument driver and the medical instrument. The chief purpose of the sterile adapter is to transfer angular motion from the drive shafts of the instrument driver to the drive inputs of the instrument while maintaining physical separation, and thus sterility, between the drive shafts and drive inputs. Accordingly, an example sterile adapter may comprise a series of rotational inputs and outputs intended to be mated with the drive shafts of the instrument driver and drive inputs on the instrument. Connected to the sterile adapter, the sterile drape, comprised of a thin, flexible material such as transparent or translucent plastic, is designed to cover the capital equipment, such as the instrument driver, robotic arm, and cart (in a cart-based system) or table (in a table-based system). Use of the drape would allow the capital equipment to be positioned proximate to the patient while still being located in an area not requiring sterilization (i.e., non-sterile field). On the other side of the sterile drape, the medical instrument may interface with the patient in an area requiring sterilization (i.e., sterile field).

D. Medical Instrument.

Figure 16:
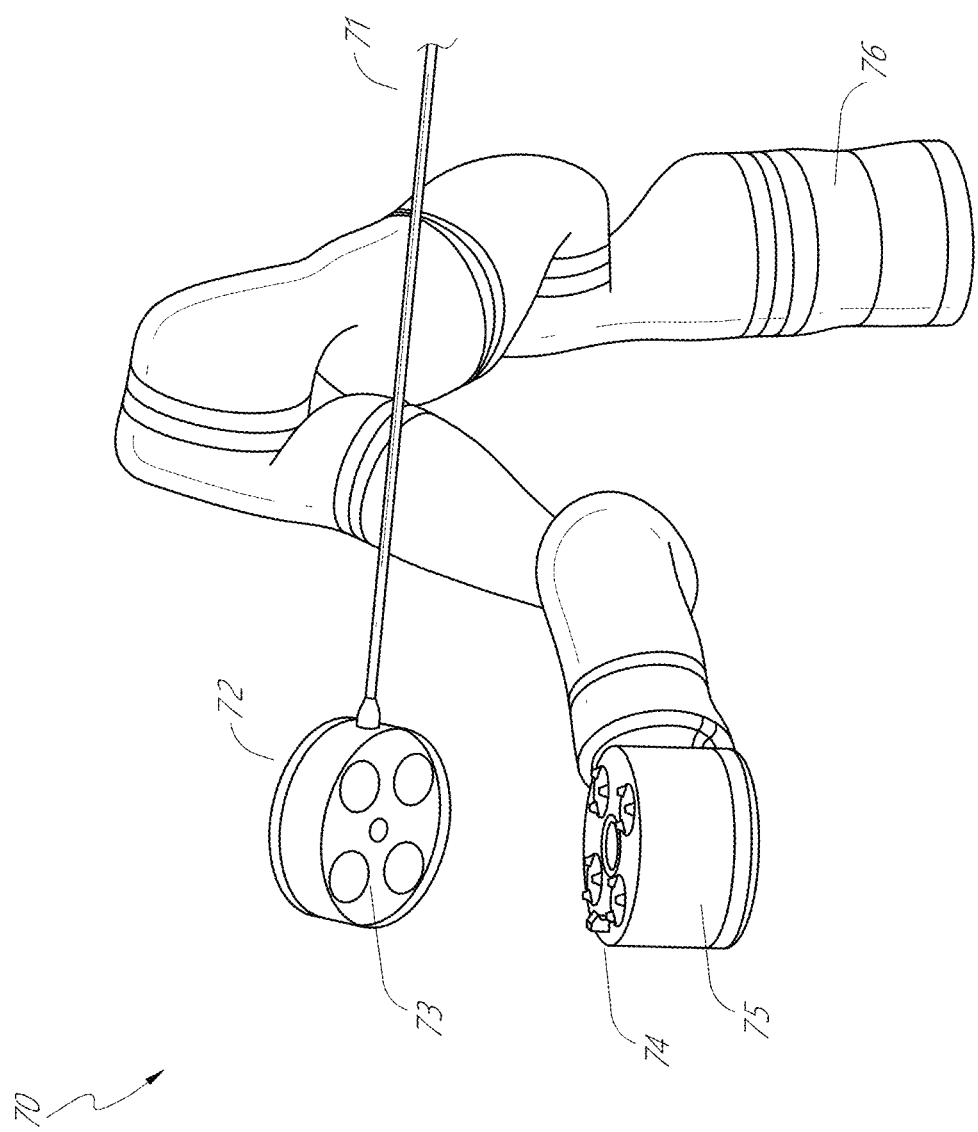
FIG. 16 illustrates an exemplary medical instrument with a paired instrument driver.

FIG. 16 illustrates an example medical instrument with a paired instrument driver. Like other instruments designed for use with a robotic system, medical instrument 70 comprises an elongated shaft 71 (or elongate body) and an instrument base 72. The instrument base 72, also referred to as an "instrument handle" due to its intended design for manual interaction by the physician, may generally comprise rotatable drive inputs 73, e.g., receptacles, pulleys or spools, that are designed to be mated with drive outputs 74 that extend through a drive interface on instrument driver 75 at the distal end of robotic arm 76. When physically connected, latched, and/or coupled, the mated drive inputs 73 of the instrument base 72 may share axes of rotation with the drive outputs 74 in the instrument driver 75 to allow the transfer of torque from the drive outputs 74 to the drive inputs 73. In some embodiments, the drive outputs 74 may comprise splines that are designed to mate with receptacles on the drive inputs 73.

The elongated shaft 71 is designed to be delivered through either an anatomical opening or lumen, e.g., as in endoscopy, or a minimally invasive incision, e.g., as in laparoscopy. The elongated shaft 71 may be either flexible (e.g., having properties similar to an endoscope) or rigid (e.g., having properties similar to a laparoscope) or contain a customized combination of both flexible and rigid portions. When designed for laparoscopy, the distal end of a rigid elongated shaft may be connected to an end effector extending from a jointed wrist formed from a clevis with at least one degree of freedom and a surgical tool or medical instrument, such as, for example, a grasper or scissors, that may be actuated based on force from the tendons as the drive inputs rotate in response to torque received from the drive outputs 74 of the instrument driver 75. When designed for endoscopy, the distal end of a flexible elongated shaft may include a steerable or controllable bending section that may be articulated and bent based on torque received from the drive outputs 74 of the instrument driver 75.

Torque from the instrument driver 75 is transmitted down the elongated shaft 71 using tendons along the elongated shaft 71. These individual tendons, such as pull wires, may be individually anchored to individual drive inputs 73 within the instrument handle 72. From the handle 72, the tendons are directed down one or more pull lumens along the elongated shaft 71 and anchored at the distal portion of the elongated shaft 71, or in the wrist at the distal portion of the elongated shaft. During a surgical procedure, such as a laparoscopic, endoscopic or hybrid procedure, these tendons may be coupled to a distally mounted end effector, such as a wrist, grasper, or scissor. Under such an arrangement, torque exerted on drive inputs 73 would transfer tension to the tendon, thereby causing the end effector to actuate in some way. In some embodiments, during a surgical procedure, the tendon may cause a joint to rotate about an axis, thereby causing the end effector to move in one direction or another. Alternatively, the tendon may be connected to one or more jaws of a grasper at the distal end of the elongated shaft 71, where tension from the tendon causes the grasper to close.

In endoscopy, the tendons may be coupled to a bending or articulating section positioned along the elongated shaft 71 (e.g., at the distal end) via adhesive, control ring, or other mechanical fixation. When fixedly attached to the distal end of a bending section, torque exerted on the drive inputs 73 would be transmitted down the tendons, causing the softer, bending section (sometimes referred to as the articulable section or region) to bend or articulate. Along the non-bending sections, it may be advantageous to spiral or helix the individual pull lumens that direct the individual tendons along (or inside) the walls of the endoscope shaft to balance the radial forces that result from tension in the pull wires. The angle of the spiraling and/or spacing therebetween may be altered or engineered for specific purposes, wherein tighter spiraling exhibits lesser shaft compression under load forces, while lower amounts of spiraling results in greater shaft compression under load forces, but limits bending. On the other end of the spectrum, the pull lumens may be directed parallel to the longitudinal axis of the elongated shaft 71 to allow for controlled articulation in the desired bending or articulable sections.

In endoscopy, the elongated shaft 71 houses a number of components to assist with the robotic procedure. The shaft 71 may comprise a working channel for deploying surgical tools (or medical instruments), irrigation, and/or aspiration to the operative region at the distal end of the shaft 71. The shaft 71 may also accommodate wires and/or optical fibers to transfer signals to/from an optical assembly at the distal tip, which may include an optical camera. The shaft 71 may also accommodate optical fibers to carry light from proximally-located light sources, such as light emitting diodes, to the distal end of the shaft 71.

At the distal end of the instrument 70, the distal tip may also comprise the opening of a working channel for delivering tools for diagnostic and/or therapy, irrigation, and aspiration to an operative site. The distal tip may also include a port for a camera, such as a fiberscope or a digital camera, to capture images of an internal anatomical space. Relatedly, the distal tip may also include ports for light sources for illuminating the anatomical space when using the camera.

In the example of FIG. 16, the drive shaft axes, and thus the drive input axes, are orthogonal to the axis of the elongated shaft 71. This arrangement, however, complicates roll capabilities for the elongated shaft 71. Rolling the elongated shaft 71 along its axis while keeping the drive inputs 73 static results in undesirable tangling of the tendons as they extend off the drive inputs 73 and enter pull lumens within the elongated shaft 71. The resulting entanglement of such tendons may disrupt any control algorithms intended to predict movement of the flexible elongated shaft 71 during an endoscopic procedure.

Figure 17:
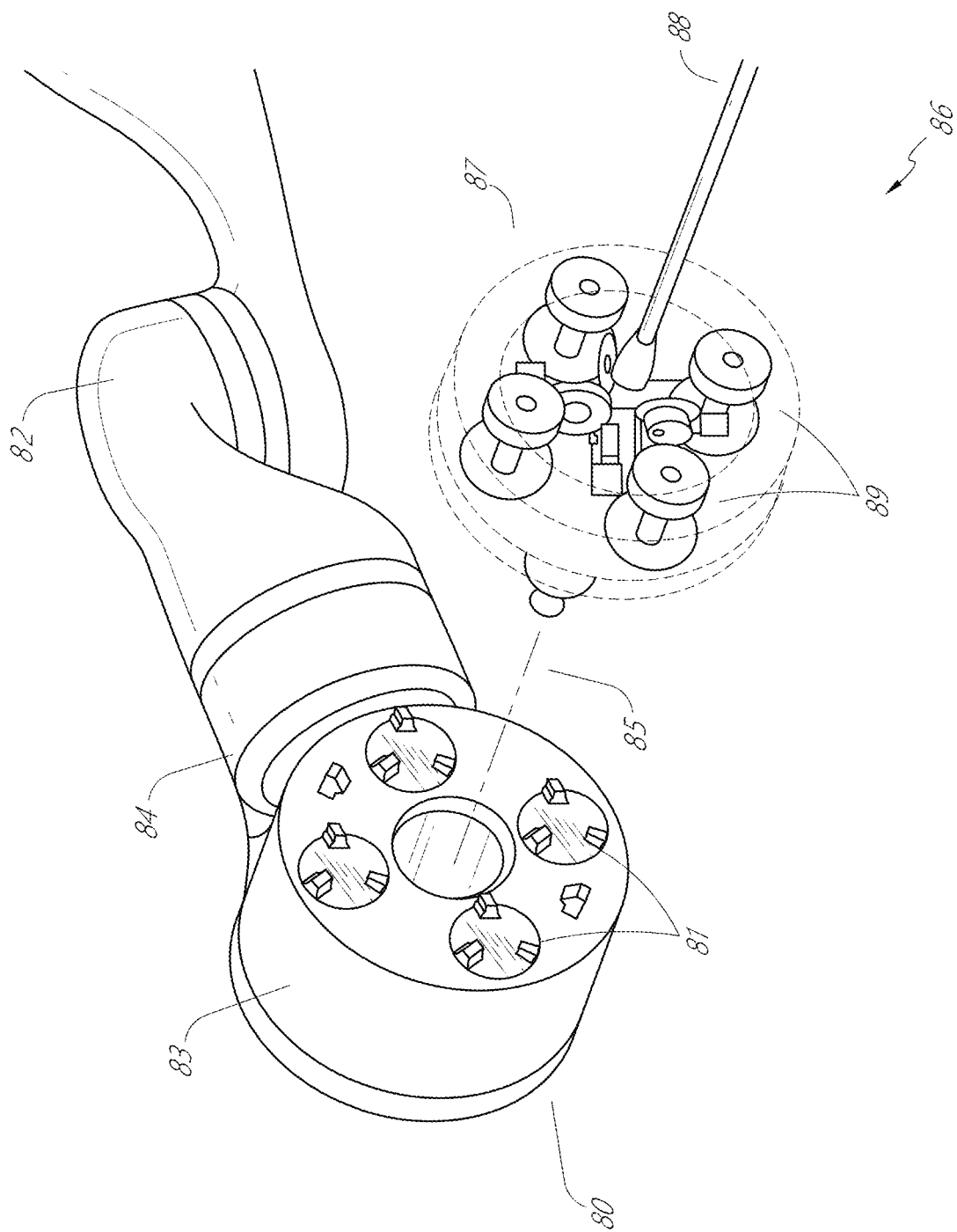
FIG. 17 illustrates an alternative design for an instrument driver and instrument where the axes of the drive units are parallel to the axis of the elongated shaft of the instrument.

FIG. 17 illustrates an alternative design for an instrument driver and instrument where the axes of the drive units are parallel to the axis of the elongated shaft of the instrument. As shown, a circular instrument driver 80 comprises four drive units with their drive outputs 81 aligned in parallel at the end of a robotic arm 82. The drive units, and their respective drive outputs 81, are housed in a rotational assembly 83 of the instrument driver 80 that is driven by one of the drive units within the assembly 83. In response to torque provided by the rotational drive unit, the rotational assembly 83 rotates along a circular bearing that connects the rotational assembly 83 to the non-rotational portion 84 of the instrument driver 80. Power and controls signals may be communicated from the non-rotational portion 84 of the instrument driver 80 to the rotational assembly 83 through electrical contacts that may be maintained through rotation by a brushed slip ring connection (not shown). In other embodiments, the rotational assembly 83 may be responsive to a separate drive unit that is integrated into the non-rotatable portion 84, and thus not in parallel to the other drive units. The rotational mechanism 83 allows the instrument driver 80 to rotate the drive units, and their respective drive outputs 81, as a single unit around an instrument driver axis 85.

Like earlier disclosed embodiments, an instrument 86 may comprise an elongated shaft portion 88 and an instrument base 87 (shown with a transparent external skin for discussion purposes) comprising a plurality of drive inputs 89 (such as receptacles, pulleys, and spools) that are configured to receive the drive outputs 81 in the instrument driver 80. Unlike prior disclosed embodiments, the instrument shaft 88 extends from the center of the instrument base 87 with an axis substantially parallel to the axes of the drive inputs 89, rather than orthogonal as in the design of FIG. 16.

When coupled to the rotational assembly 83 of the instrument driver 80, the medical instrument 86, comprising instrument base 87 and instrument shaft 88, rotates in combination with the rotational assembly 83 about the instrument driver axis 85. Since the instrument shaft 88 is positioned at the center of instrument base 87, the instrument shaft 88 is coaxial with instrument driver axis 85 when attached. Thus, rotation of the rotational assembly 83 causes the instrument shaft 88 to rotate about its own longitudinal axis. Moreover, as the instrument base 87 rotates with the instrument shaft 88, any tendons connected to the drive inputs 89 in the instrument base 87 are not tangled during rotation. Accordingly, the parallelism of the axes of the drive outputs 81, drive inputs 89, and instrument shaft 88 allows for the shaft rotation without tangling any control tendons.

Figure 18:
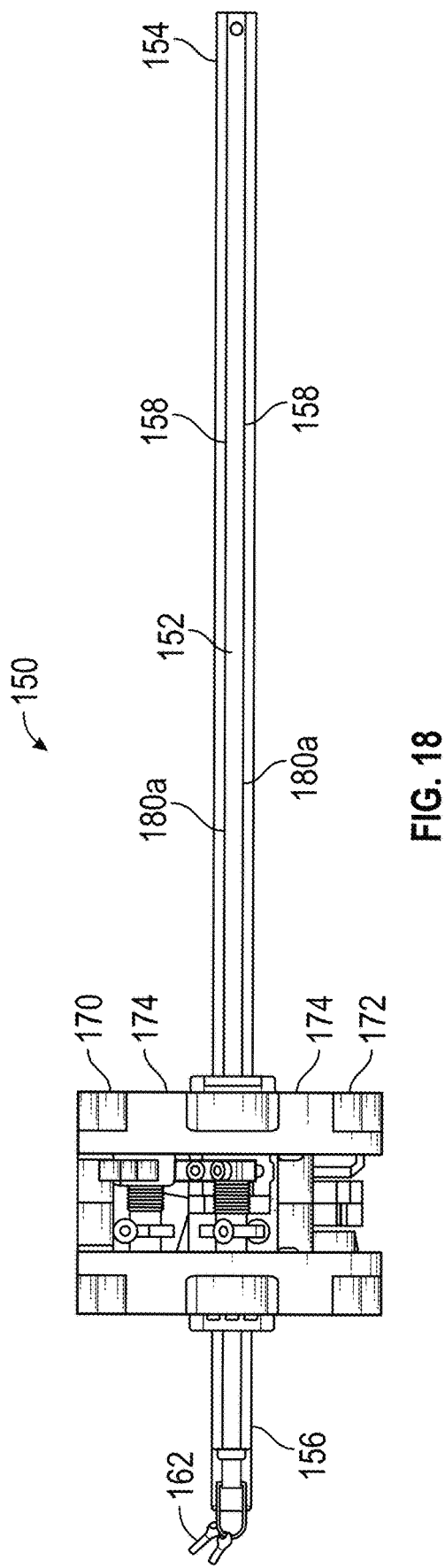
FIG. 18 illustrates an instrument having an instrument-based insertion architecture.

FIG. 18 illustrates an instrument having an instrument based insertion architecture in accordance with some embodiments. The instrument 150 can be coupled to any of the instrument drivers discussed above. The instrument 150 comprises an elongated shaft 152, an end effector 162 connected to the shaft 152, and a handle 170 coupled to the shaft 152. The elongated shaft 152 comprises a tubular member having a proximal portion 154 and a distal portion 156. The elongated shaft 152 comprises one or more channels or grooves 158 along its outer surface. The grooves 158 are configured to receive one or more wires or cables 180 therethrough. One or more cables 180 thus run along an outer surface of the elongated shaft 152. In other embodiments, cables 180 can also run through the elongated shaft 152. Manipulation of the one or more cables 180 (e.g., via an instrument driver) results in actuation of the end effector 162.

The instrument handle 170, which may also be referred to as an instrument base, may generally comprise an attachment interface 172 having one or more mechanical inputs 174, e.g., receptacles, pulleys or spools, that are designed to be reciprocally mated with one or more torque couplers on an attachment surface of an instrument driver.

In some embodiments, the instrument 150 comprises a series of pulleys or cables that enable the elongated shaft 152 to translate relative to the handle 170. In other words, the instrument 150 itself comprises an instrument-based insertion architecture that accommodates insertion of the instrument, thereby minimizing the reliance on a robot arm to provide insertion of the instrument 150. In other embodiments, a robotic arm can be largely responsible for instrument insertion.

E. Controller.

Any of the robotic systems described herein can include an input device or controller for manipulating an instrument attached to a robotic arm. In some embodiments, the controller can be coupled (e.g., communicatively, electronically, electrically, wirelessly and/or mechanically) with an instrument such that manipulation of the controller causes a corresponding manipulation of the instrument e.g., via master slave control.

Figure 19:
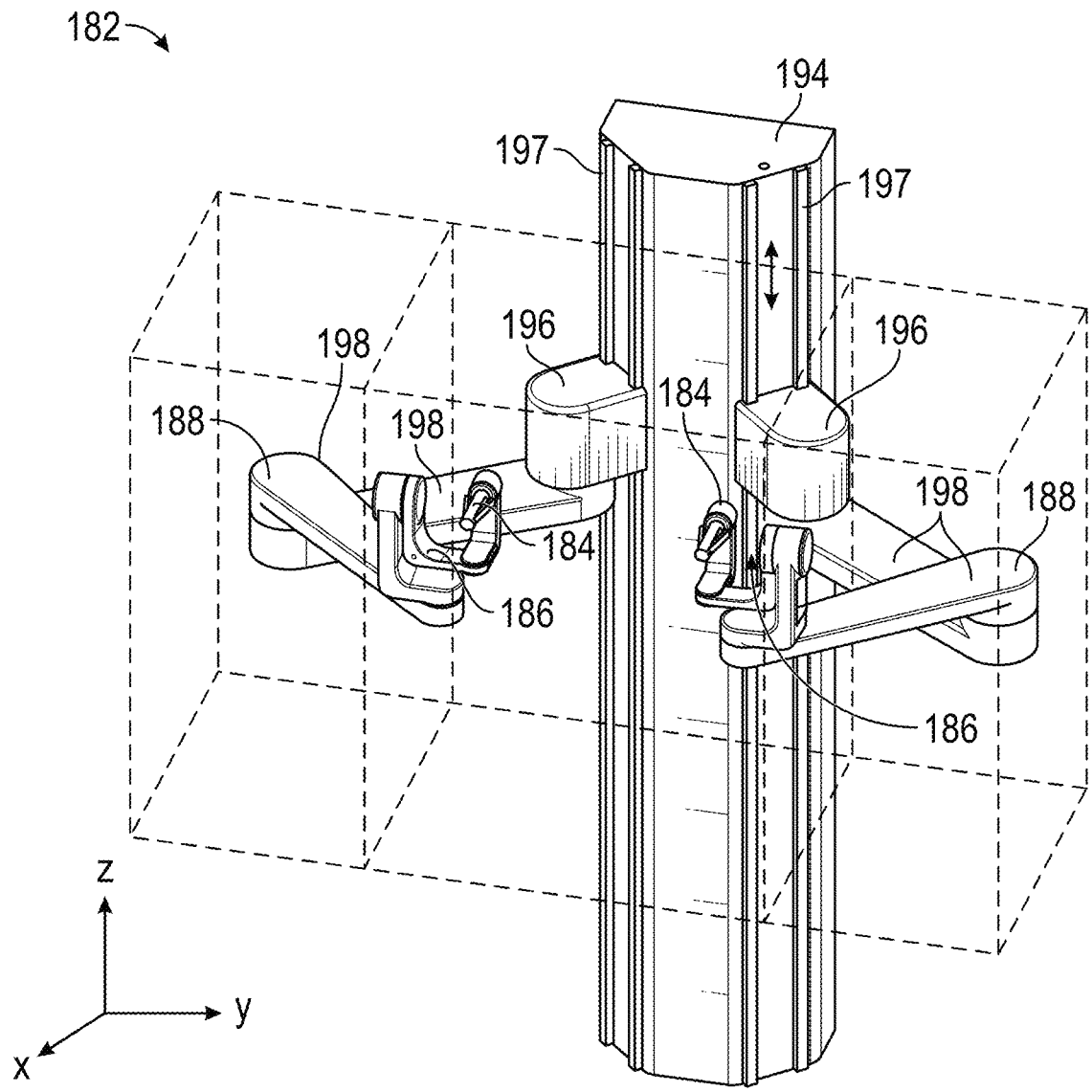
FIG. 19 illustrates an exemplary controller.

FIG. 19 is a perspective view of an embodiment of a controller 182. In the present embodiment, the controller 182 comprises a hybrid controller that can have both impedance and admittance control. In other embodiments, the controller 182 can utilize just impedance or passive control. In other embodiments, the controller 182 can utilize just admittance control. By being a hybrid controller, the controller 182 advantageously can have a lower perceived inertia while in use.

In the illustrated embodiment, the controller 182 is configured to allow manipulation of two medical instruments, and includes two handles 184. Each of the handles 184 is connected to a gimbal 186. Each gimbal 186 is connected to a positioning platform 188.

As shown in FIG. 19, each positioning platform 188 includes a SCARA arm (selective compliance assembly robot arm) 198 coupled to a column 194 by a prismatic joint 196. The prismatic joints 196 are configured to translate along the column 194 (e.g., along rails 197) to allow each of the handles 184 to be translated in the z-direction, providing a first degree of freedom. The SCARA arm 198 is configured to allow motion of the handle 184 in an x-y plane, providing two additional degrees of freedom.

In some embodiments, one or more load cells are positioned in the controller. For example, in some embodiments, a load cell (not shown) is positioned in the body of each of the gimbals 186. By providing a load cell, portions of the controller 182 are capable of operating under admittance control, thereby advantageously reducing the perceived inertia of the controller while in use. In some embodiments, the positioning platform 188 is configured for admittance control, while the gimbal 186 is configured for impedance control. In other embodiments, the gimbal 186 is configured for admittance control, while the positioning platform 188 is configured for impedance control. Accordingly, for some embodiments, the translational or positional degrees of freedom of the positioning platform 188 can rely on admittance control, while the rotational degrees of freedom of the gimbal 186 rely on impedance control.

F. Navigation and Control.

Traditional endoscopy may involve the use of fluoroscopy (e.g., as may be delivered through a C-arm) and other forms of radiation-based imaging modalities to provide endoluminal guidance to an operator physician. In contrast, the robotic systems contemplated by this disclosure can provide for non-radiation-based navigational and localization means to reduce physician exposure to radiation and reduce the amount of equipment within the operating room. As used herein, the term "localization" may refer to determining and/or monitoring the position of objects in a reference coordinate system. Technologies such as preoperative mapping, computer vision, real-time EM tracking, and robot command data may be used individually or in combination to achieve a radiation-free operating environment. In other cases, where radiation-based imaging modalities are still used, the preoperative mapping, computer vision, real-time EM tracking, and robot command data may be used individually or in combination to improve upon the information obtained solely through radiation-based imaging modalities.

Figure 20:
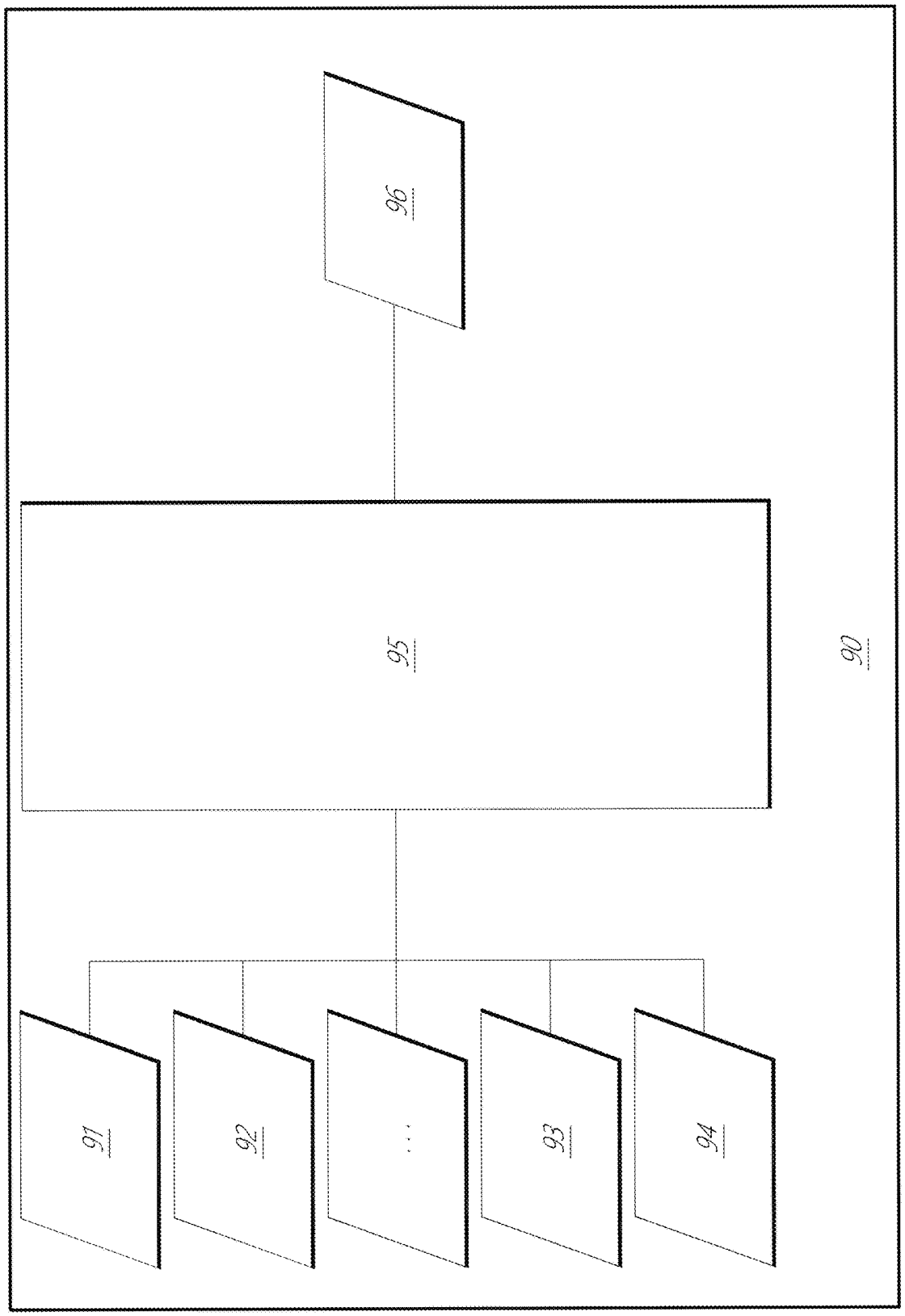
FIG. 20 depicts a block diagram illustrating a localization system that estimates a location of one or more elements of the robotic systems of FIGS. 1-10, such as the location of the instrument of FIGS. 16-18, in accordance to an example embodiment.

FIG. 20 is a block diagram illustrating a localization system 90 that estimates a location of one or more elements of the robotic system, such as the location of the instrument, in accordance to an example embodiment. The localization system 90 may be a set of one or more computer devices configured to execute one or more instructions. The computer devices may be embodied by a processor (or processors) and computer-readable memory in one or more components discussed above. By way of example and not limitation, the computer devices may be in the tower 30 shown in FIG. 1, the cart 11 shown in FIGS. 1-4, the beds shown in FIGS. 5-14, etc.

As shown in FIG. 20, the localization system 90 may include a localization module 95 that processes input data 91-94 to generate location data 96 for the distal tip of a medical instrument. The location data 96 may be data or logic that represents a location and/or orientation of the distal end of the instrument relative to a frame of reference. The frame of reference can be a frame of reference relative to the anatomy of the patient or to a known object, such as an EM field generator (see discussion below for the EM field generator).

The various input data 91-94 are now described in greater detail. Preoperative mapping may be accomplished through the use of the collection of low dose CT scans. Preoperative CT scans are reconstructed into three-dimensional images, which are visualized, e.g. as "slices" of a cutaway view of the patient's internal anatomy. When analyzed in the aggregate, image-based models for anatomical cavities, spaces and structures of the patient's anatomy, such as a patient lung network, may be generated. Techniques such as center-line geometry may be determined and approximated from the CT images to develop a three-dimensional volume of the patient's anatomy, referred to as model data 91 (also referred to as "preoperative model data" when generated using only preoperative CT scans). The use of center-line geometry is discussed in U.S. patent application Ser. No. 14/523,760, the contents of which are herein incorporated in its entirety. Network topological models may also be derived from the CT-images, and are particularly appropriate for bronchoscopy.

In some embodiments, the instrument may be equipped with a camera to provide vision data (or image data) 92. The localization module 95 may process the vision data 92 to enable one or more vision-based (or image-based) location tracking modules or features. For example, the preoperative model data 91 may be used in conjunction with the vision data 92 to enable computer vision-based tracking of the medical instrument (e.g., an endoscope or an instrument advance through a working channel of the endoscope). For example, using the preoperative model data 91, the robotic system may generate a library of expected endoscopic images from the model based on the expected path of travel of the endoscope, each image linked to a location within the model. Intraoperatively, this library may be referenced by the robotic system in order to compare real-time images captured at the camera (e.g., a camera at a distal end of the endoscope) to those in the image library to assist localization.

Other computer vision-based tracking techniques use feature tracking to determine motion of the camera, and thus the endoscope. Some features of the localization module 95 may identify circular geometries in the preoperative model data 91 that correspond to anatomical lumens and track the change of those geometries to determine which anatomical lumen was selected, as well as the relative rotational and/or translational motion of the camera. Use of a topological map may further enhance vision-based algorithms or techniques.

Optical flow, another computer vision-based technique, may analyze the displacement and translation of image pixels in a video sequence in the vision data 92 to infer camera movement. Examples of optical flow techniques may include motion detection, object segmentation calculations, luminance, motion compensated encoding, stereo disparity measurement, etc. Through the comparison of multiple frames over multiple iterations, movement and location of the camera (and thus the endoscope) may be determined.

The localization module 95 may use real-time EM tracking to generate a real-time location of the endoscope in a global coordinate system that may be registered to the patient's anatomy, represented by the preoperative model. In EM tracking, an EM sensor (or tracker) comprising one or more sensor coils embedded in one or more locations and orientations in a medical instrument (e.g., an endoscopic tool) measures the variation in the EM field created by one or more static EM field generators positioned at a known location. The location information detected by the EM sensors is stored as EM data 93. The EM field generator (or transmitter), may be placed close to the patient to create a low intensity magnetic field that the embedded sensor may detect. The magnetic field induces small currents in the sensor coils of the EM sensor, which may be analyzed to determine the distance and angle between the EM sensor and the EM field generator. These distances and orientations may be intraoperatively "registered" to the patient anatomy (e.g., the preoperative model) in order to determine the geometric transformation that aligns a single location in the coordinate system with a position in the preoperative model of the patient's anatomy. Once registered, an embedded EM tracker in one or more positions of the medical instrument (e.g., the distal tip of an endoscope) may provide real-time indications of the progression of the medical instrument through the patient's anatomy.

Robotic command and kinematics data 94 may also be used by the localization module 95 to provide localization data 96 for the robotic system. Device pitch and yaw resulting from articulation commands may be determined during preoperative calibration. Intraoperatively, these calibration measurements may be used in combination with known insertion depth information to estimate the position of the instrument. Alternatively, these calculations may be analyzed in combination with EM, vision, and/or topological modeling to estimate the position of the medical instrument within the network.

As FIG. 20 shows, a number of other input data can be used by the localization module 95. For example, although not shown in FIG. 20, an instrument utilizing shape-sensing fiber can provide shape data that the localization module 95 can use to determine the location and shape of the instrument.

The localization module 95 may use the input data 91-94 in combination(s). In some cases, such a combination may use a probabilistic approach where the localization module 95 assigns a confidence weight to the location determined from each of the input data 91-94. Thus, where the EM data may not be reliable (as may be the case where there is EM interference) the confidence of the location determined by the EM data 93 can be decrease and the localization module 95 may rely more heavily on the vision data 92 and/or the robotic command and kinematics data 94.

As discussed above, the robotic systems discussed herein may be designed to incorporate a combination of one or more of the technologies above. The robotic system's computer-based control system, based in the tower, bed and/or cart, may store computer program instructions, for example, within a non-transitory computer-readable storage medium such as a persistent magnetic storage drive, solid state drive, or the like, that, upon execution, cause the system to receive and analyze sensor data and user commands, generate control signals throughout the system, and display the navigational and localization data, such as the position of the instrument within the global coordinate system, anatomical map, etc.

2. Medical Instruments Including Wrists with Hybrid Redirect Surfaces

The robotic medical systems described above, as well as other robotic medical systems and/or non-robotic medical systems, can use medical instruments that include wrists with hybrid redirect surfaces as described in this section. As described above, a medical instrument can include an end effector positioned at the distal end of an elongated shaft. The end effector can be connected to the distal end of the elongated shaft by a wrist. The wrist can be articulable so as to allow for control of the end effector. As noted above, the medical instrument can include one or more pull wires extending through the wrist to the end effector. The one or more pull wires can be actuated (e.g., pulled or tensioned) to articulate the wrist and the end effector. As the one or more pull wires extend through the wrist, they can be engaged with one or more pulleys within the wrist.

Figure 21:
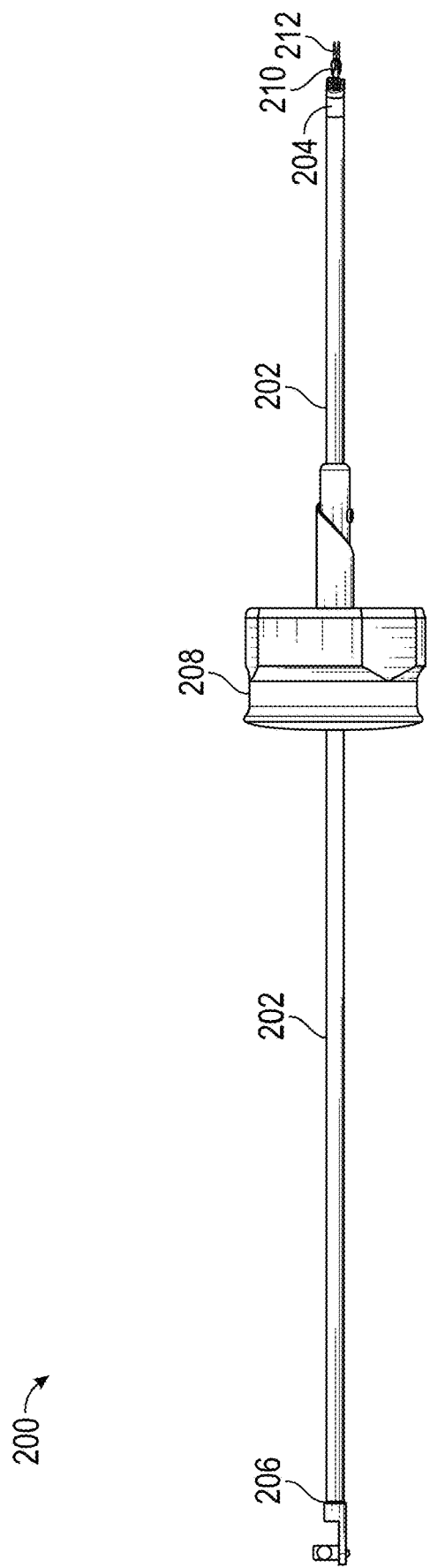
FIG. 21 is a side view of an embodiment of a medical instrument including an end effector connected to a shaft of the medical instrument by a wrist.

FIG. 21 is a side view of an embodiment of a medical instrument 200. The medical instrument 200 can be similar to the medical instruments described above, for example, with reference to FIGS. 16-18. As illustrated, the medical instrument 200 includes an elongated shaft 202 and a handle 208. The elongated shaft 202 extends between a distal end 204 and a proximal end 206. An end effector 212, which in the illustrated embodiment is configured as a grasper, can be positioned at the distal end 204 of the elongated shaft 202. As illustrated, the end effector 212 can be connected to the distal end 204 of the elongated shaft 202 by a wrist 210. The wrist 210 can be configured to allow one or more degrees of freedom for the instrument 200. For example, the wrist 210 can be a two degree-of-freedom wrist. As an example, a two degree-of-freedom wrist can allow the end effector 212 to pivot or rotate around a pitch axis and a yaw axis.

In the illustrated embodiment of FIG. 21, the instrument 200 includes the handle 208. The handle 208 can be configured to connect to an instrument drive mechanism, for example, as shown in FIGS. 16 and 17, described above. As previously mentioned, the instrument 200 may include one or more tendons, cables, or pull wires that extend along (e.g., through or on) the elongated shaft 202 between the end effector 212 and the handle 208. The handle 208 may include one or more drive inputs configured to engage one or more drive outputs on the instrument drive mechanism (see FIGS. 16 and 17) to allow the instrument drive mechanism to actuate (e.g., tension or pull) the pull wires. Actuating the pull wires can cause motion of wrist 210 and/or the end effector 212 to allow for remote manipulation and control of the end effector 212. For example, in some embodiments, actuation of the pull wires can be configured to cause jaws of the end effector 212 to open and close and/or to allow the end effector 212 to rotate about pitch and/or yaw axes. As mentioned above, the instrument drive mechanism can be positioned on a robotic arm. In some embodiments, the robotic arm can be controlled to position, roll, advance, and/or retract the instrument 200.

As shown in FIG. 21, in some embodiments, the elongated shaft 202 extends through the handle 208. In such an embodiment, the elongated shaft 202 can be configured to advance or retract relative to the handle 208. In some embodiments, the instrument drive mechanism is configured to cause the elongated shaft 202 to advance or retract relative to the handle 208. This can allow, for example, the handle 208 to remain stationary while the elongated shaft 202 and end effector 212 are advanced into a patient during a procedure. In some embodiments, the proximal end 206 of the elongated shaft 202 is attached to the handle 208 such that the elongated shaft 202 extends only between the end effector 212 and the handle 208.

In accordance with an aspect of the present disclosure, redirect surfaces within the wrist 210 can be configured to change a direction of a pull wire so as to direct the pull wire between the pulleys. As will be described more fully below with reference to FIG. 22, some wrists may include only "static" redirect surfaces. As used herein, a "static" redirect surface refers to a non-moving, or stationary surface formed on or within the wrist that contacts a pull wire to redirect it. For example, a static redirect surface can be a static, stationary, or non-moving wall or channel formed on or in a clevis of the wrist along which a pull wire slides as it is redirected.

In some embodiments, the medical instruments including wrists with hybrid redirect surfaces described in this section (e.g., as shown in FIGS. 23A-23E) include at least one static redirect surface and at least one "dynamic" redirect surface. As used herein, a "dynamic" redirect surface refers to a moving surface of the wrist that contacts a pull wire to redirect it. For example, a dynamic redirect surface can be a surface of a rotating pulley of the wrist that redirects a pull wire. Examples of static and redirect surfaces will be provided below to more fully illustrate these concepts.

In some instances, there can be both advantages and disadvantages associated with both static redirect surfaces and dynamic redirect surfaces. For example, static redirect surfaces may be considered more mechanically simple as they may comprise a stationary or static surface. However, static redirect surfaces may cause more wear on pull wires. Because a static redirect surface remains stationary as it redirects a pull wire, the pull wire may slide across the static redirect surface. Friction between the pull wire and the static redirect surface can cause wear that can shorten the life span of the pull wire. Dynamic redirect surfaces may reduce or eliminate the wear problems that can be associated with static redirect surfaces. This can be because the dynamic redirect surface rotates or otherwise moves along with the movement of the pull wire, reducing the friction therebetween. This can increase the lifespan of the pull wire. In some instances, however, dynamic redirect surfaces may be considered more mechanically complex. For example, dynamic redirect surfaces may require additional components (compared with static redirect surfaces). Further, it may be difficult to provide the additional components of a dynamic redirect surface in a small or compact form factor as is often desirable for medical instruments associated with laparoscopic surgery, for example.

The medical instruments including wrists with hybrid redirect surfaces described in this section can include one or more static redirect surfaces and one or more dynamic redirect surfaces in a manner that can increase the advantages associated with each while minimizing the disadvantages. For example, in some embodiments, dynamic redirect surfaces are implemented to redirect pull wire segments associated with a close motion of the end effector (e.g., a clamping motion), while static redirect surfaces are implemented to redirect pull wire segments associated with an open motion of the end effector (e.g., an unclamping motion). Because it often takes more force, tension, or load to close the end effector (or more force is generally applied in the closing direction), the pull wire segments associated with the close motion of the end effector can experience more force and be exposed to more wear. By using dynamic redirect surfaces to redirect these pull wire segments, wear on the pull wires can be reduced, improving the lifespan of the pull wire. Opening the end effector can take less force, and thus the pull wire segments associated with the open motion of the end effector can experience less force and less wear. Thus, it can be advantageous to use static redirect for these pull wire segments because use of these static redirect surfaces can be less mechanically complex.

Further, the medical instruments including wrists with hybrid redirect surfaces described in this section can include novel structural architecture that can allow for packaging of both static and dynamic redirect surfaces in a minimal form factor that is suitable for a laparoscopic or endoscopic medical instrument and that may provide one or more additional advantages as described further below. The features and advantages of the medical instruments including wrists with hybrid redirect surfaces of the present application will now be described in greater detail with reference to FIGS. 21-26B.

Figure 22:
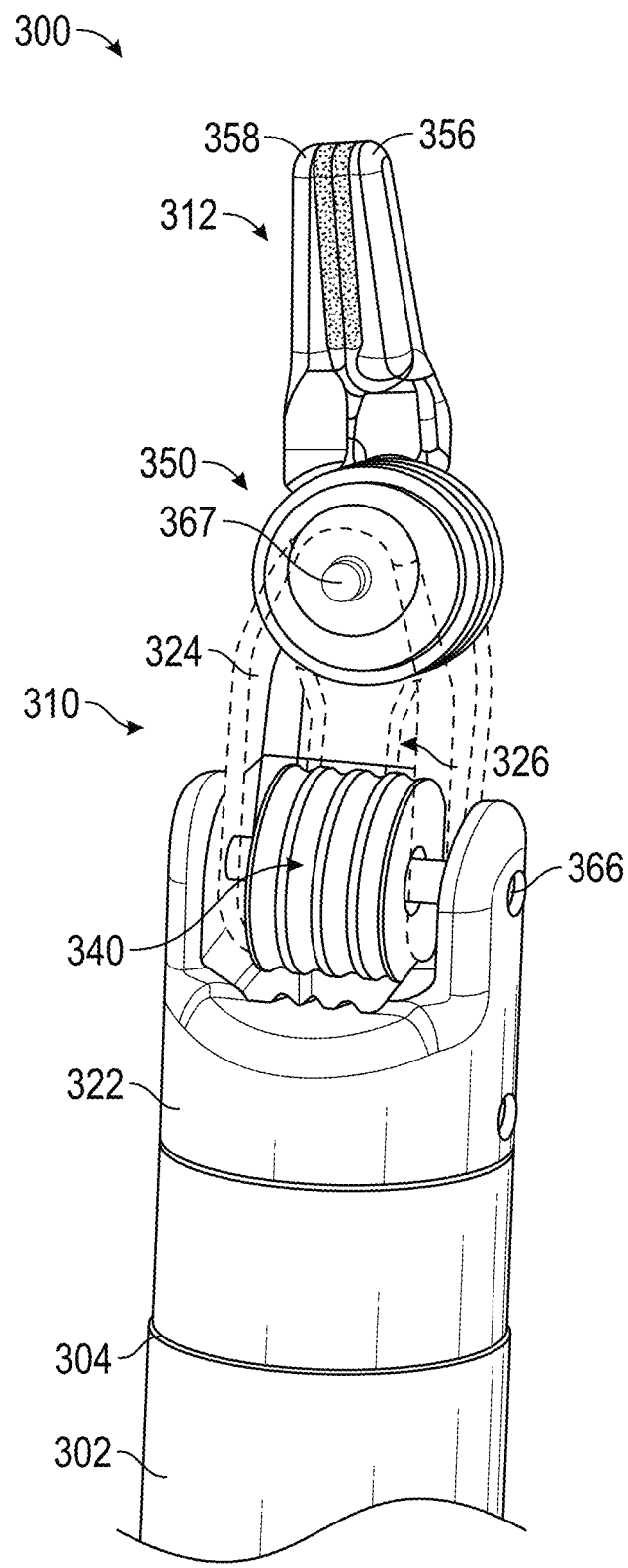
FIG. 22 is a perspective view of an embodiment of an end effector and wrist of a medical instrument that includes static redirect surfaces in the wrist.

As an aid to understanding medical instruments with wrists including hybrid redirect surfaces (as shown, for example, in FIGS. 23A-23E), a medical instrument with a wrist including only static redirect surfaces will first be described with reference to FIG. 22. FIG. 22 shows a perspective view of a distal end of a medical instrument 300 that includes a wrist with only static redirect surfaces.

As illustrated, a wrist 310 is positioned at the distal end 304 of the elongated shaft 302 of the medical instrument 300. The wrist 310 includes a proximal clevis 322 and a distal clevis 324. In the illustrated embodiment, the distal clevis 324 is illustrated as transparent so as to visualize features formed within the distal clevis 324. The proximal clevis 322 is connected to the distal end 304 of the elongated shaft 302. The distal clevis 324 is pivotally connected to the proximal clevis 322. For example, a proximal axle 366 can extend through and connect the distal clevis 324 to the proximal clevis 322 such that the distal clevis 324 can rotate relative to the proximal clevis 322 about a longitudinal axis of the proximal axle 366. This may allow the wrist 310 to move or articulate in a first degree of freedom. The first degree of freedom may be pitch.

As shown in FIG. 22, a plurality of pulleys 340 can also be mounted on the proximal axle 366 at the joint between the proximal clevis 322 and the distal clevis 324. In the illustrated embodiment, four proximal pulleys 340 are included. As will be described in more detail below, a plurality of pull wires (not shown) can be engaged with the proximal pulleys 340 and actuated to control the pitch of the medical instrument 300.

An end effector 312 is connected to the distal clevis 324. In the illustrated embodiment, the end effector 312 comprises a gripper having a first jaw member 356 and a second jaw member 358. Other types of end effectors can also be used, such as graspers, cutters, scissors, etc. In the illustrated embodiment, each of the jaw members 356, 358 is connected to one of two distal pulleys 350 connected to the distal clevis 324. An example jaw member is shown alone in FIG. 24, which is described below. As illustrated, a distal axle 367 can extend through the distal clevis 324, and the distal pulleys 350 can be rotatably mounted on the distal axle 367. The distal pulleys 350 can thus rotate relative to the distal clevis 324 to allow the end effector 312 to rotated in a second degree of freedom. The second degree of freedom can be yaw. Additionally, if the distal pulleys 350 are rotated in opposite directions, a third degree of freedom can be provided. The third degree of freedom can be opening and closing the end effector 312. The plurality of pull wires (not shown) can be engaged with the distal pulleys 350 and actuated to control the pitch of the medical instrument 300 and to open and close the end effector 312.

As illustrated in FIG. 22, the proximal axle 366 and the distal axle 367 can be oriented along axes that extend in different directions. In the illustrated embodiment, the proximal axle 366 extends along the pitch axis and the distal axle 367 extends along the yaw axis. The pitch and yaw axes can be orthogonal to each other. Thus, the proximal pulleys 340 and the distal pulleys 350 rotate in different planes, which, in the illustrated embodiment, are orthogonal to each other. As the plurality of pull wires are engaged with both the proximal pulleys 340 and the distal pulleys 350, the plurality of pull wires need to be redirected between the proximal pulleys 340 and the distal pulleys 350. For example, the plurality of pull wires need to be redirected from the plane of proximal pulleys 340 to the plane of the distal pulleys 350. To facilitate redirection of the pull wires, the distal clevis 324 includes a plurality of static redirect surfaces 326 that are configured to redirect the plurality of pull wires. As shown, the static redirect surfaces 326 comprise angled or curved faces formed in the distal clevis 324 for redirecting the plurality of pull wires. As the various pull wire segments of the plurality of pull wires are actuated, the pull wire segments slide across the static redirect surfaces 326 as they are redirected.

The static redirect surfaces 326 can be provided to change a course of direction for one or more pull wire segments of the plurality of pull wires. In the medical instrument 300 of FIG. 22, the wrist 310 comprises a distal clevis 324 having only static redirect surfaces 326, in the form of one or more angled, curved or sloped surfaces. While such static redirect surfaces 326 can successfully redirect the pull wires, the sliding of the pull wire segments against the static redirect surfaces 326 can cause abrasion to the outside of the pull wires due to increased friction, thereby reducing pull wire life. In addition, the space available for static redirect surfaces 326 between the proximal pulleys 340 and the distal pulleys 350 can be limited.

The medical instrument 300 shown in FIG. 22 can be considered an N+1 medical instrument because it achieves three degrees of freedom (pitch, yaw, and instrument actuation) using four pull wire segments.

In contrast with the medical instrument 300 of FIG. 22, FIGS. 23A-23E illustrate a medical instrument 400 with a wrist that includes hybrid redirect surfaces. That is, the wrist of FIGS. 23A-23E includes both static redirect surfaces and dynamic redirect surfaces. Use of hybrid redirect surfaces within the wrist can alleviate wear on the pull wires. While FIGS. 23A-23E illustrate an example configured as a grasper instrument, one skilled in the art will appreciate that the use of hybrid redirect surfaces is not limited to instruments simply for grasping, but can be applicable to many other instruments as well (e.g., cauterization instruments, cutting instruments, suction and irrigation instruments, etc.).

As will be described below, the medical instrument 400 includes both static and dynamic redirect surfaces to realize both the packaging benefits of static redirect surfaces and the performance and life improvements of dynamic redirect surfaces. As mentioned above, during operation, the pull wire segments associated with closing the end effector may have significantly more load on them the pull wire segments associated with opening the end effector. Thus, most of the benefits of dynamic redirect surfaces can be realized by having the dynamic redirect surfaces engaged with the pull segments associated with closing the end effector. At the same time, pull wire segments that experience less load and tension can be redirected using static redirect surfaces.

Figure 23A:
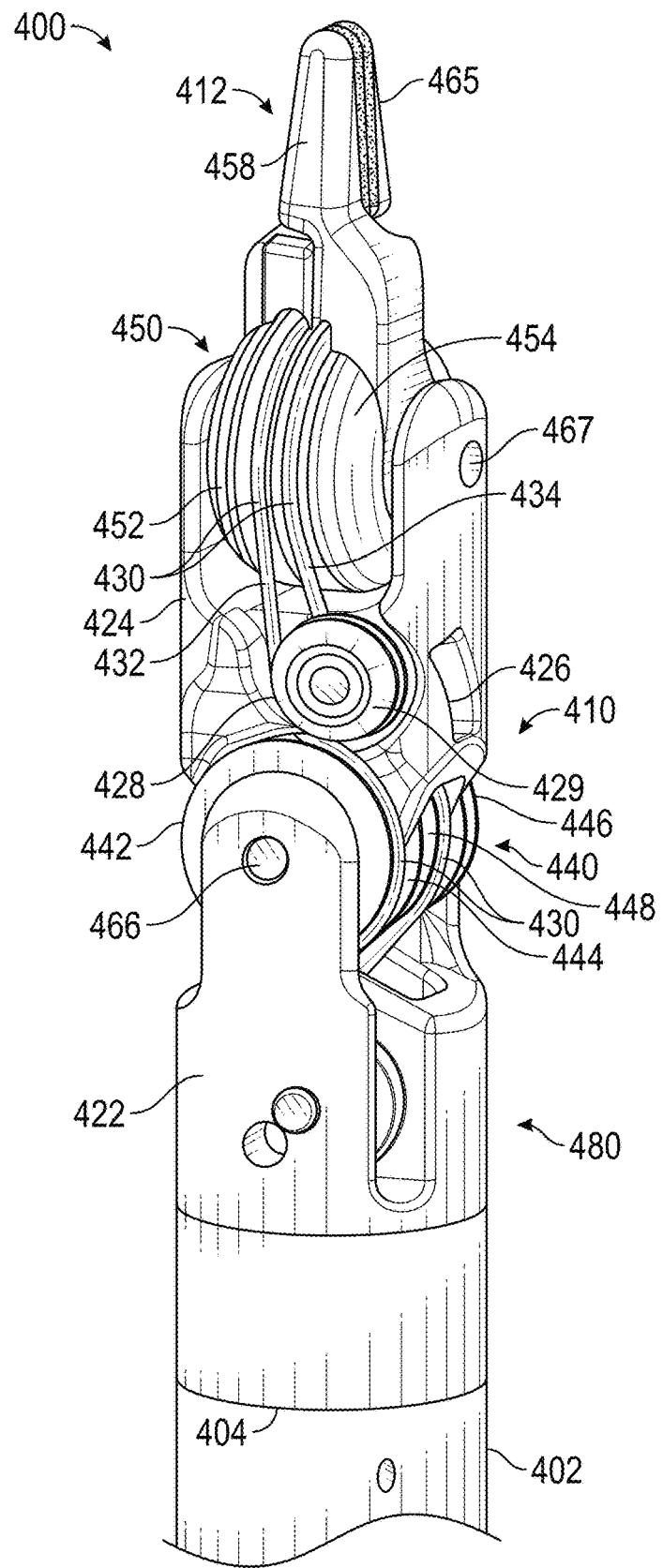
FIGS. 23A-23E illustrate an embodiment of a medical instrument including a wrist with hybrid redirect surfaces.
Figure 23B:
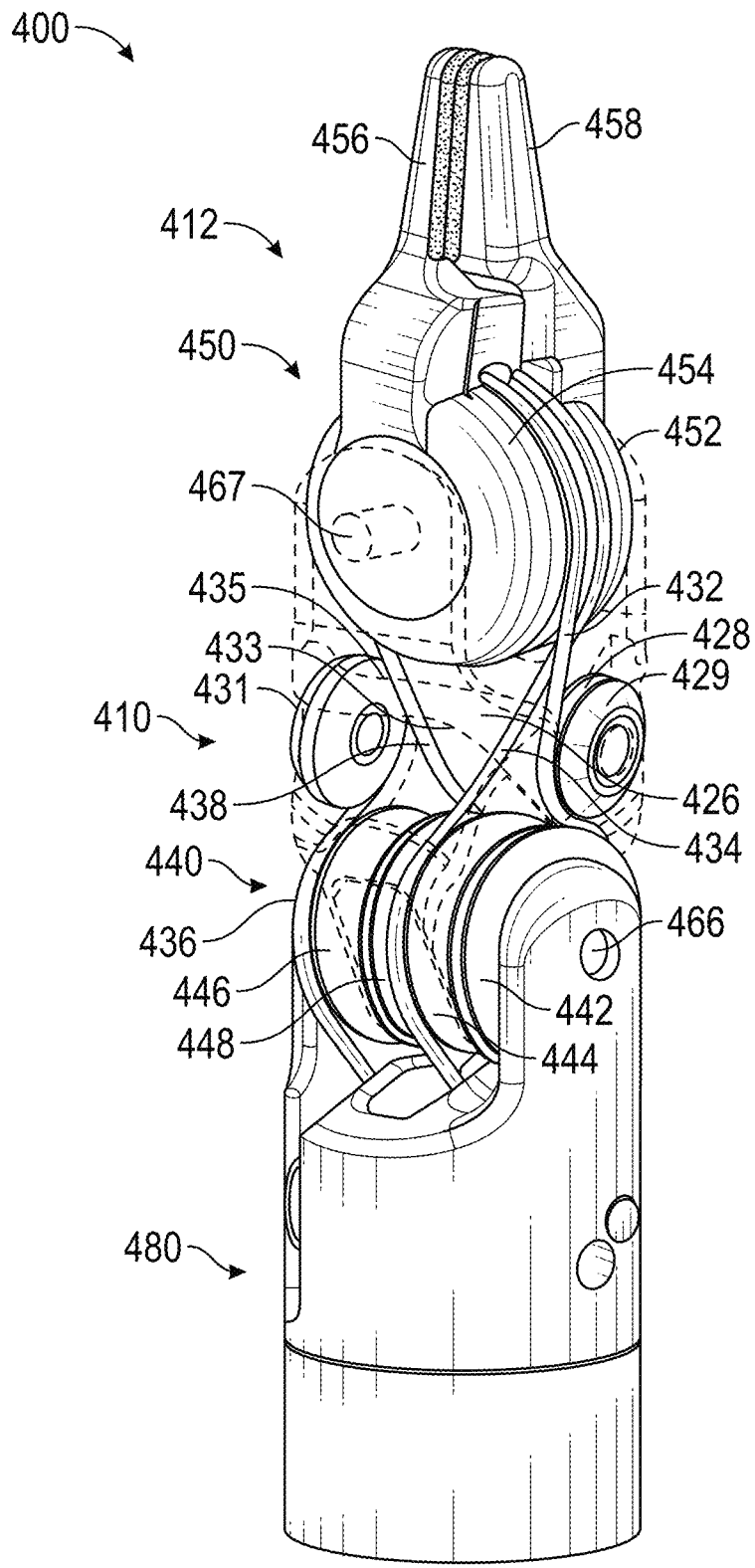
Figure 23C:
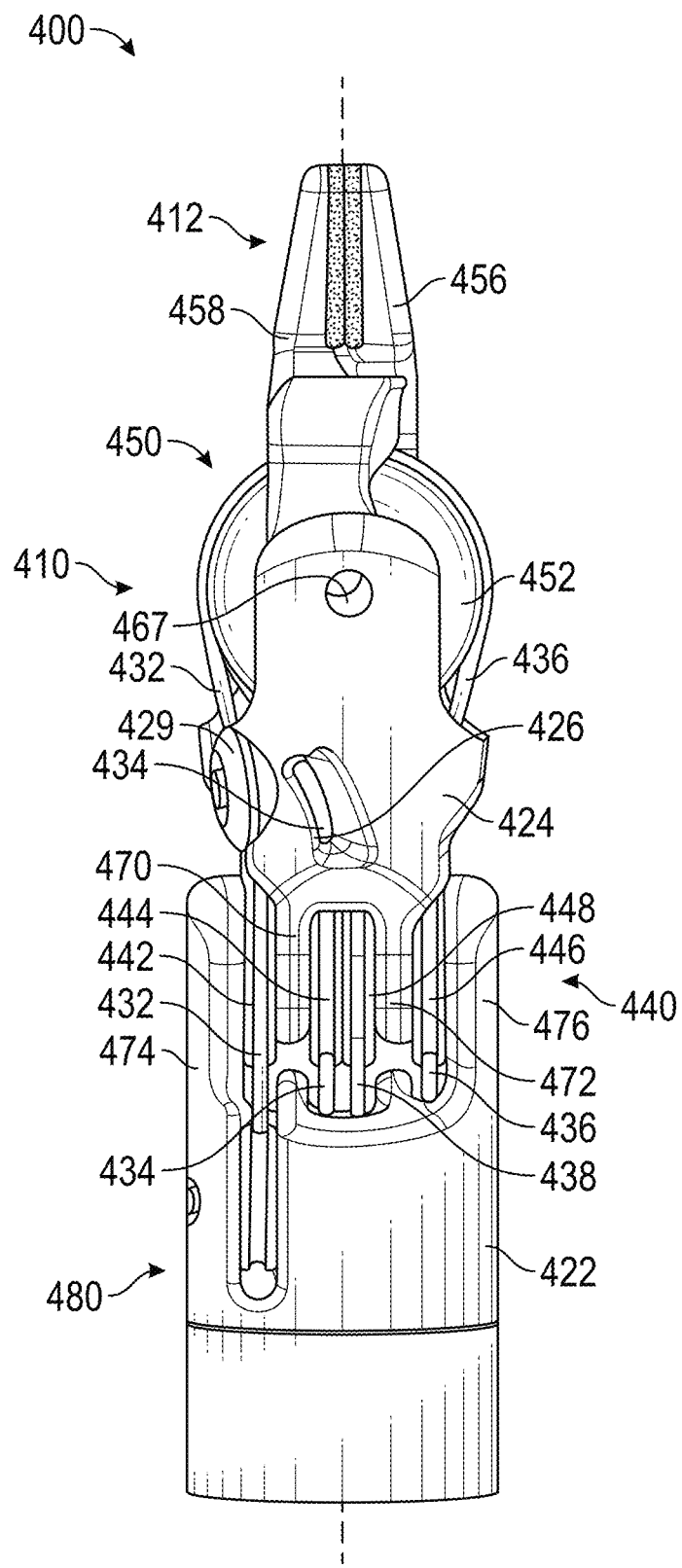
Figure 23D:
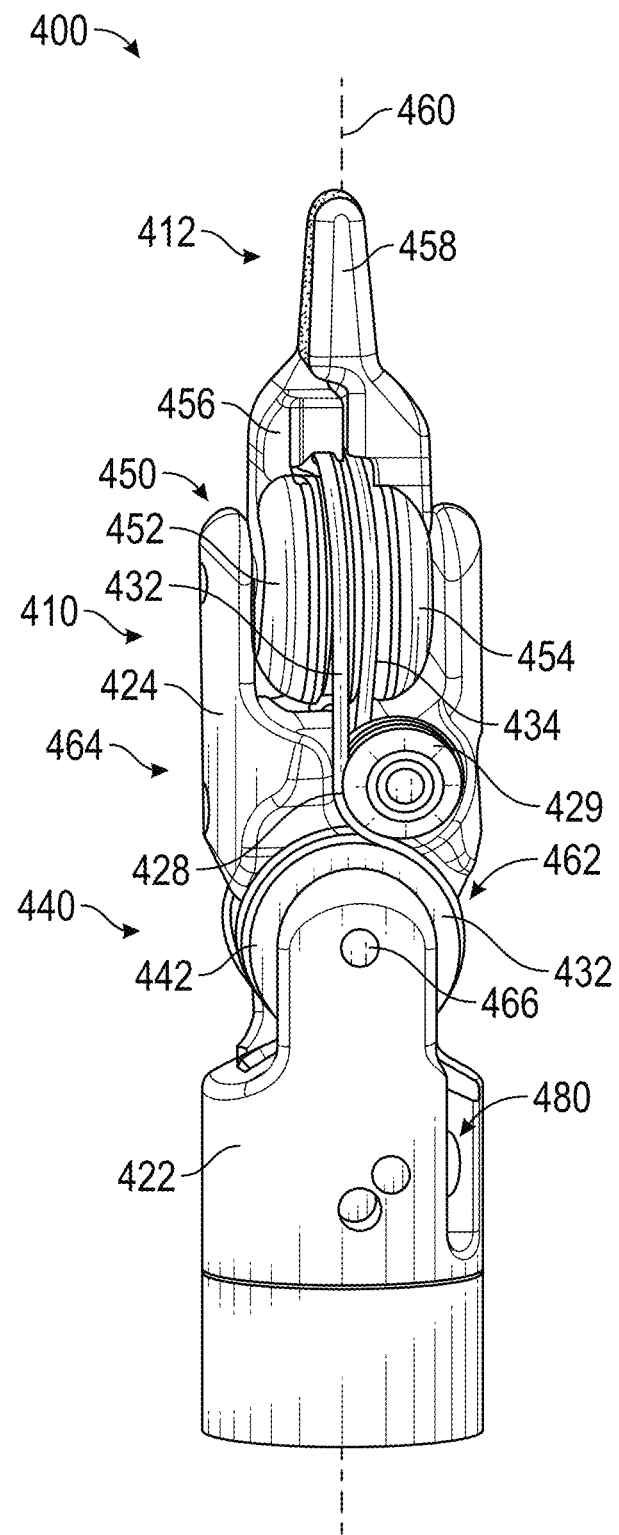
Figure 23E:
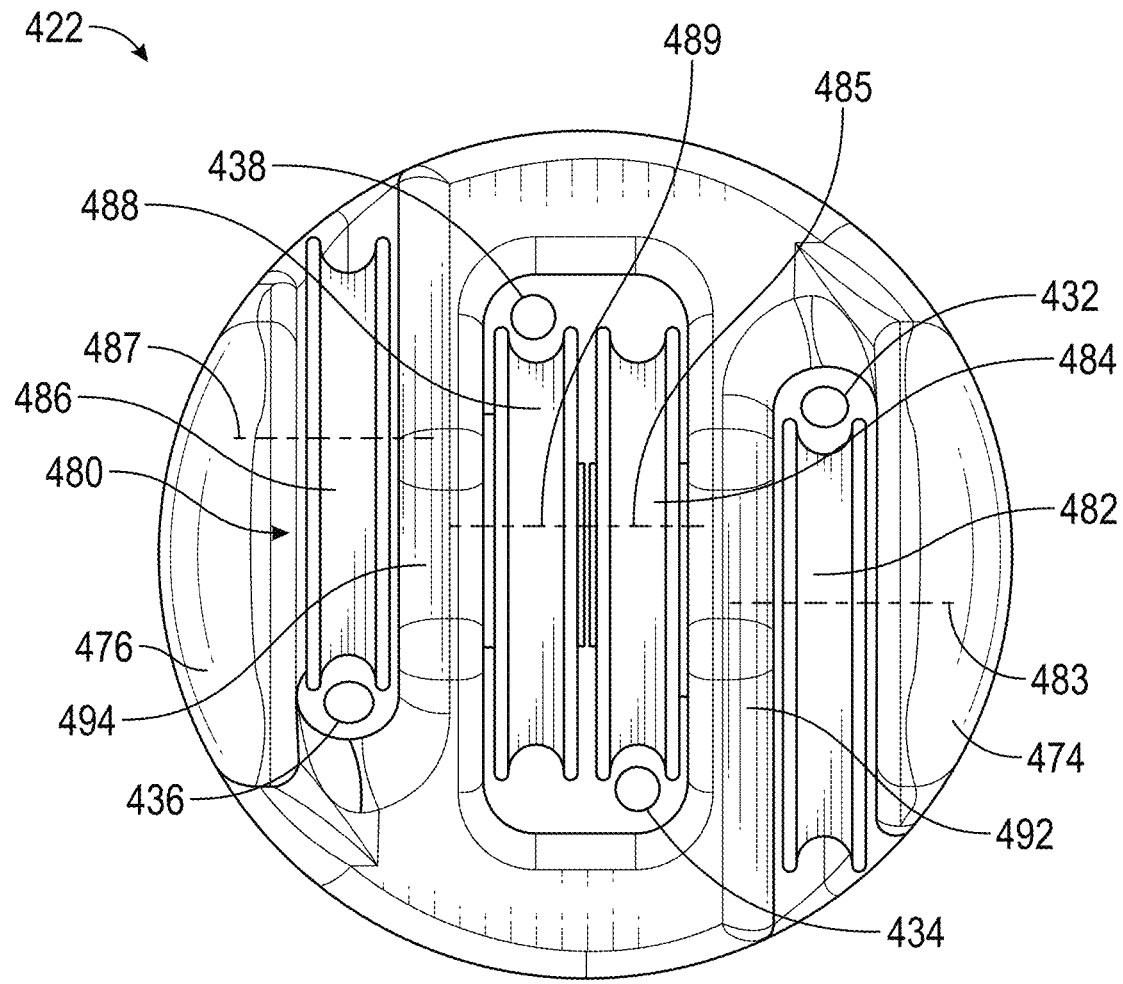

The structure of the medical instrument 400 will be described with reference to FIGS. 23A-23E. FIG. 23A is a perspective view of the medical instrument 400. FIG. 23B is another perspective view of the medical instrument 400, shown with a distal clevis 424 illustrated as transparent so as to visualize certain internal features thereof. FIG. 23C is a is a first side view of the medical instrument 400. FIG. 23D is a second side view of the medical instrument 400. FIG. 23E is a top view of a proximal clevis 422 of the medical instrument 400.

As shown in FIG. 23A, in the illustrated embodiment, the medical instrument 400 includes an elongated shaft 402 extending to a distal end 404. Only the distal end 404 of the elongated shaft 402 is visible in FIG. 23A, but the elongated shaft 402 may be similar to the elongated shaft 202 of the medical instrument 200 described above. A wrist 410 is positioned at the distal end 404 of the elongated shaft 402. The wrist 410 is also connected to an end effector 412, which as noted above is a grasper in the illustrated embodiment. As will be described in more detail below, the wrist 410 can be configured to allow articulation in two degrees of freedom. In the example described below, the two degrees of freedom are pitch and yaw. Additionally, the end effector 412 can open and close providing an additional degree of freedom for the medical instrument 400. The medical instrument 400 can be considered an N+1 medical instrument because it achieves three degrees of freedom (pitch, yaw, and instrument actuation) using four pull wire segments.

In the illustrated embodiment, the wrist 410 comprises a proximal clevis 422 and a distal clevis 424. The proximal clevis 422 can be attached to the distal end 404 of the elongated shaft 402. The distal clevis 424 can be pivotally attached to the proximal clevis 422. In the illustrated embodiment, the distal clevis 424 is pivotally attached to the proximal clevis 422 by an axle 466 which extends through the distal clevis 424 and the proximal clevis 422. The distal clevis 424 can rotate about an axis of the axle 466 relative to the proximal clevis 422. Rotation of the distal clevis 424 about an axis of the axle 466 relative to the proximal clevis 422 can provide one of the degrees of freedom of the wrist 410. For example, this degree of freedom can be pitch. Thus, the axle 466 can be considered a pitch axle and the axis of the axle 466 can be considered the pitch axis of the wrist 410.

As best seen in FIG. 23C, the proximal clevis 422 can include a first proximal clevis support leg 474 and a second proximal clevis support leg 476. The axle 466 can extend through the first proximal clevis support leg 474 and the second proximal clevis support leg 476 of the proximal clevis 422. Similarly, the distal clevis 424 can include a first distal clevis support leg 470 and a second distal clevis support leg 472. The axle 466 extends through the first distal clevis support leg 470 and the second distal clevis support leg 472 of the distal clevis 424. As will be described below, in some embodiments, the first proximal clevis support leg 474, the second proximal clevis support leg 476, the first distal clevis support leg 470, and the second distal clevis support leg 472 can be spaced in a manner that can provide an advantageous architecture for medical instruments with wrists having hybrid redirect surfaces.

As shown in FIGS. 23A-23D, the medical instrument 400 includes a plurality of proximal pulleys 440 and a plurality of distal pulleys 450 positioned in the wrist 410. As best seen in FIGS. 23A-23C, the proximal pulleys 440 can be positioned on the axle 466 that connects the proximal clevis 422 and the distal clevis 424. As noted above, the axle 466 can be a pitch axle, and thus, the proximal pulleys 440 may also be considered pitch pulleys 440. In the illustrated embodiment, the proximal pulleys 440 include a first outer proximal pulley 442, a first inner proximal pulley 444, a second outer proximal pulley 446, and a second inner proximal pulley 448. The first outer proximal pulley 442, the first inner proximal pulley 444, the second outer proximal pulley 446, and the second inner proximal pulley 448 can each be positioned on the axle 466 such that they can rotate about the axle 466. The proximal pulleys 440 each rotate in a pitch plane that is perpendicular to the axis of the axle 466.

As seen in FIGS. 23A-23D, the distal pulleys 450 can be positioned on an axle 467. The axle 467 can extend through the distal clevis 424 as shown. The axis of the axle 467 can provide a second degree of freedom for the medical instrument 400. For example, this second degree of freedom can be yaw. Accordingly, the axle 467 can be considered a yaw axle and can provide a yaw axis for the wrist 410. In the illustrated embodiment, the distal pulleys 450 include a first distal pulley 452 and a second distal pulley 454 mounted on the axle 467. Each of the distal pulleys 450 can be configured rotate in a yaw plane that is perpendicular to the axis of axle 467.

The pitch axle 466 and the yaw axle 467 can be oriented at an angle with respect to each other. In the illustrated example, the pitch axle 466 and the yaw axle 467 are orthogonal. Accordingly, the pitch plane and the yaw plane can also be orthogonal to each other.

The end effector 412 of the medical instrument 400 can be formed by a first jaw member 456 and a second jaw member 458. The first jaw member 456 can be connected to the first distal pulley 452 and the second jaw member 458 can be connected to the second distal pulley 454. The orientation of the end effector 412 can be controlled by rotating the first distal pulley 452 and the second distal pulley 454 in the same direction about the axle 467. For example, by rotating both of the first distal pulley 452 and the second distal pulley 454 in the same direction about the axle 467 the yaw of the end effector 412 can be adjusted. The end effector 412 can be actuated (e.g., opened or closed in the case of the illustrated grasper) by rotating the first distal pulley 452 and the second distal pulley 454 in the opposite directions about the axle 467. Actuation of the end effector 412 can be considered a third degree of freedom of the medical instrument 400.

The medical instrument 400 can include a plurality of pull wires 430 that can be actuated (e.g., pulled or tensioned) to control the three degrees of freedom of the medical instrument 400 (pitch, yaw, and actuation). As shown in FIGS. 23A-23D, the plurality of pull wires 430 are engaged with the proximal pulleys 440 and the distal pulleys 450. In the illustrated embodiment, the plurality of pull wires 430 include a first pull wire segment 432, a second pull wire segment 434, a third pull wire segment 436, and a fourth pull wire segment 438 which are routed along various paths through the wrist 410.

For example, in the illustrated embodiment, the first pull wire segment 432 engages the first outer proximal pulley 442 and the first distal pulley 452. Actuation of the first pull wire segment 432 can be associated with closing the first jaw member 456. The second pull wire segment 434 can be engaged with the first inner proximal pulley 444 and the second distal pulley 454. The second pull wire segment 434 can be associated with opening the second jaw member 458. The third pull wire segment 436 can be engaged with the second outer proximal pulley 446 and second distal pulley 454. The third pull wire segment 436 can be associated with closing the second jaw member 458. The fourth pull wire segment 438 can be engaged with the second inner proximal pulley 448 and the first distal pulley 452. The fourth pull wire segment 438 can be associated with opening the first jaw member 456.

As shown in the figures, each of the first pull wire segment 432 and the fourth pull wire segment 438 can engage the first distal pulley 452, but on opposite sides. Similarly, each of the second pull wire segment 434 and the third pull wire segment 436 can engage the second distal pulley 454, but on opposite sides. In the illustrated embodiment, each of the proximal pulleys 440 is only engaged by one of the pull wire segments. The first pull wire segment 432 engages the first outer proximal pulley 442 on the same side of the wrist 410 that the fourth pull wire segment 438 engages the second inner proximal pulley 448. Similarly, the second pull wire segment 434 engages the first inner proximal pulley 444 on the same side of the wrist 410 that the third pull wire segment 436 engages the second outer, proximal pulley 446. At the proximal pulleys 440, the first and fourth pull wire segments 432, 438 are positioned on an opposite side of the wrist 410 than the second and third pull wire segments 434, 436.

As best seen in FIG. 23B, which illustrates the distal clevis 424 as transparent, the plurality of pull wires 430 are redirected between proximal pulleys 440 and distal pulleys 450. To accomplish the redirection, the wrist 410 of the instrument 400 includes hybrid redirect surfaces. Specifically, in the illustrated embodiment, the wrist 410 includes a pair of static redirect surfaces and a pair of dynamic redirect surfaces positioned between proximal pulleys 440 and distal pulleys 450. As shown in FIG. 23B, the pair of static redirect surfaces include a first static redirect surface 426 and a second static redirect surface 433. The first static redirect surface 426 and the second static redirect surface 433 can each be an angled or curved surface formed in or on the distal clevis 424. An example is visible in FIG. 23C, which shows the static redirect surface 426. The pair of dynamic redirect surfaces include a first dynamic redirect surface 428 and a second dynamic redirect surface 431. Each of the first dynamic redirect surface 428 and the second dynamic redirect surface 431 can comprise a surface of a redirect pulley, such as the first redirect pulley 429 and the second redirect pulley 435 that are illustrated in the figures.

The plurality of pull wires 430 are redirected by the static redirect surfaces 426, 433 and the dynamic redirect surfaces 428, 431. In the illustrated embodiment, the first pull wire segment 432 engages the first dynamic redirect surface 428. The second pull wire segment 434 engages the first static redirect surface 426. The third pull wire segment 436 engages the second dynamic redirect surface 431. The fourth pull wire segment 438 engages the second static redirect surface 433.

Thus, in this example, the first and third pull wire segments 432, 436, which are associated with closing the end effector 412 are redirected using the dynamic redirect surfaces 428, 431 of the redirect pulleys 429, 435, respectively. The second and fourth pull wire segments 434, 438, which are associated with opening the end effector 412 are redirected using the static redirect surfaces 426, 433, respectively.

The medical instrument 400 also includes shaft redirect pulleys 480 positioned in the proximal clevis 422 and/or within the elongated shaft 402. The shaft redirect pulleys 480 are best seen in FIG. 23E which is a top down view of the proximal clevis 422. As shown, the shaft redirect pulleys 480 include a first outer shaft redirect pulley 482, a first inner shaft redirect pulley 484, a second outer shaft redirect pulley 486, and second inner shaft redirect pulley 488. In the illustrated embodiment, the shaft redirect pulleys 480 are in a staggered position. That is, as shown in FIG. 23E, the first outer shaft redirect pulley 482 is positioned on first axis 483 and the first inner shaft redirect pulley 484 is positioned on second axis 485. The first and second axes 483, 485 are not coaxial (in the illustrated embodiment). The second inner shaft redirect pulley 488 is positioned on a third axis 489. In the illustrated embodiment the third axis 489 is coaxial with second axis 485. The second outer shaft redirect pulley 486 is positioned on fourth axis 487. In the illustrated embodiment, the fourth axis 487 is not coaxial with the first, second, or third axes 483, 485, 489. The proximal clevis 422 also comprises a first proximal clevis support wall 492 and a second proximal clevis support wall 494. The a first proximal clevis support wall 492 is positioned between the first inner and outer shaft redirect pulleys 482, 484. The second proximal clevis support wall 494 is positioned between the second inner and outer shaft redirect pulleys 486, 484. The first proximal clevis support leg 474 and the second proximal clevis support leg 476 are also shown in FIG. 23E.

The structure of the medical instrument 400 (which includes hybrid redirect surfaces) can provide several notable features and advantages over other types of medical instruments, such as medical instruments that only include static redirect surfaces (e.g., FIG. 22). For example, with respect to the illustrated embodiment of the medical instrument 400 (shown as a grasper instrument), during operation, the pull wire segments that are associated with closing the end effector 412 (the first and third pull wire segments 432, 436) can have greater load than pull wire segments that are used for opening the end effector 412 (the second and fourth pull wire segments 434, 438). As such, it can be particularly beneficial to have pull wire segments for closing the end effector 412 run along the dynamic redirect surfaces 428, 431 so as to reduce the risk of pull wire wear, while having pull wires segments for opening the end effector 412 run along the static redirect surfaces 426, 433, as illustrated in FIG. 23B. Because the dynamic redirect surfaces 428, 431 move with the first and third pull wire segments 432, 436 (as the redirect pulleys 429, 435 rotate) friction between the dynamic redirect surfaces 428, 431 and the pull wire segments 432, 436 can be reduced when compared to the friction experienced between pull wire segments and static redirect surface. As noted previously, this can extend the lifespan of the pull wires.

The structure of the medical instrument 400 can include several features that enable or facilitate the use of hybrid redirect surfaces within the distal clevis 424. First, the distal clevis support legs 470, 472 of the distal clevis 424 can be positioned between the inner and outer proximal pulleys. For example, as shown in FIG. 23D, the first distal clevis support leg 470 is positioned between the first outer proximal pulley 442 and the first inner proximal pulley 444. Similarly, the second distal clevis support leg 472 is positioned between the second outer proximal pulley 446 and the second inner, proximal pulley 448. This arrangement or architecture provides for a distance of separation between the stationary redirect surfaces 426, 433 and the dynamic redirect surface 428, 431 (e.g., the redirect pulleys 429, 435). This distance can provide clearance and enough room to mount the redirect pulleys 429, 435 and for adjacent pull wire segments to pass without interference. This is best seen in FIG. 23D. Because the first distal clevis support leg 470 is positioned between the first outer, proximal pulley 442 and the first inner, proximal pulley 444 the third pull wire segment 446 has additional room to cross behind the first redirect pulley 429. Additionally, this configuration can allow the axle of the redirect pulley 429 to be on the outside of the distal clevis support leg 470, so that the distal clevis support leg 470 does not need to be cut through to accommodate the axle.

Second, the dynamic redirect pulleys 429, 432 can be sized such that they can reach across to the far distal pulley 450. This can enable a larger redirect pulley 429, 432 to be fit within the distal clevis 424, which can improve the lifetime of the pull wire segment that travels there over. Larger dynamic redirect surfaces (e.g., redirect pulleys) can often lead to larger life performance. As such, it is of benefit to include as large of a redirect pulley as possible within the limited space between the distal and proximal pulleys. This is shown in FIG. 23D. The redirect cable 439 is sufficiently large such that pull wire segment 432 crosses from a first lateral side 462 of the to a second lateral side 464 (across plane 460) to the first distal pulley 452, which is located on the opposite side from where the pull wire segment 432 engages the first outer proximal pulley 431. In some embodiments, to accommodate the larger dynamic redirect pulley 429, the stationary redirect surface 426 is designed to cross behind the pulley 429 without intersection (see FIG. 23C), which is enabled by the extra room provided by the distal clevis support leg (discussed above).

Third, in the illustrated embodiment, the outer shaft redirect pulleys 482, 486 in the proximal clevis 422 do not share a common axis with the inner shaft redirect pulleys 484, 488 in the proximal clevis 422. Note that the shaft redirect pulleys 480 (see FIG. 23E) all provide dynamic redirect surfaces. This can be possible because there may be greater room within the proximal clevis 422 to accommodate the shaft redirect pulleys 480. As noted above, larger dynamic redirect surfaces (e.g., redirect pulleys) can often lead to longer life performance. In some instances, staggering the shaft redirect pulleys 480 can allow for larger pulleys to be used. Further, the addition of the distal clevis support legs 470, 472 between the inner and outer proximal pulleys 440 can push out the location of the corresponding shaft redirect pulleys 480 that are located in the shaft 402 of the medical instrument 400. As the outer shaft redirect pulleys 482, 486 are pushed out, there is less space to fit the multiple (e.g., four) shaft redirect pulleys 480 along a common axis. While it is possible to reduce the size of one or more proximal redirect pulleys 480, this may reduce the life and performance benefits. Accordingly, in the illustrated embodiment, the proximal redirect pulleys 480 are sized such that cables are maintained within the inner diameter of the instrument shaft 402, while the edge of the outer shaft redirect pulleys 482, 486 are just inside the outer diameter of the instrument shaft 402.

These three features noted in the preceding paragraphs can provide an advantageous wrist structure using hybrid redirect surfaces. In some embodiments, not all three features need be included.

Figure 24:
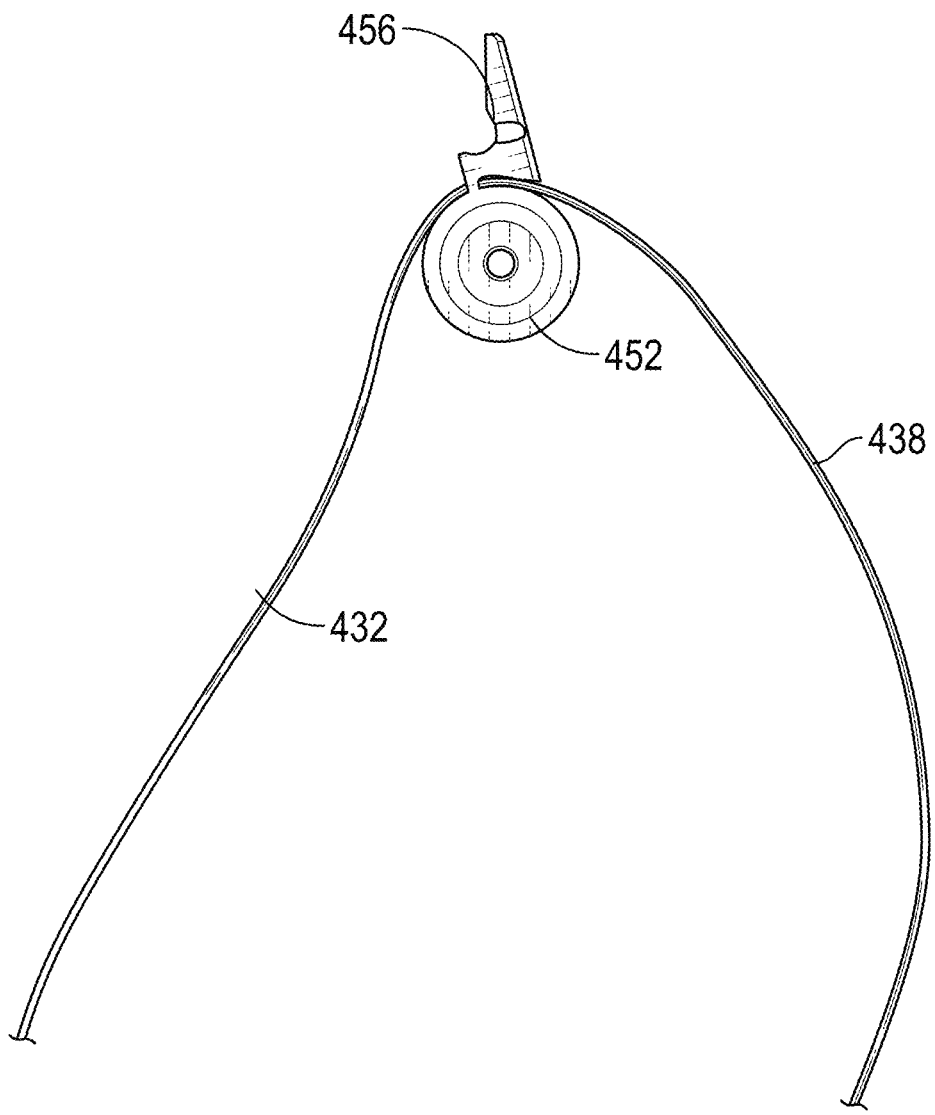
FIG. 24 illustrates an embodiment of a distal pulley, jaw member, and pull wire of a medical instrument.

FIG. 24 illustrates an embodiment of the first distal pulley 452 and attached jaw member 456 as well as the first pull wire segment 432 and the fourth pull wire segment 438. FIG. 24 is also representative of the second distal pulley 454 with associated second pull wire segment 434 and third pull wire segment 436. As noted above, the first pull wire segment 432 is associated with opening the jaw member 456 and the fourth pull wire segment 438 is associated with closing the jaw member 456. In some embodiments, the two pull wire segments 432, 438 can be part of the same pull wire, or each part of different pull wires that share a crimp at the jaw member 456.

Figure 25A:
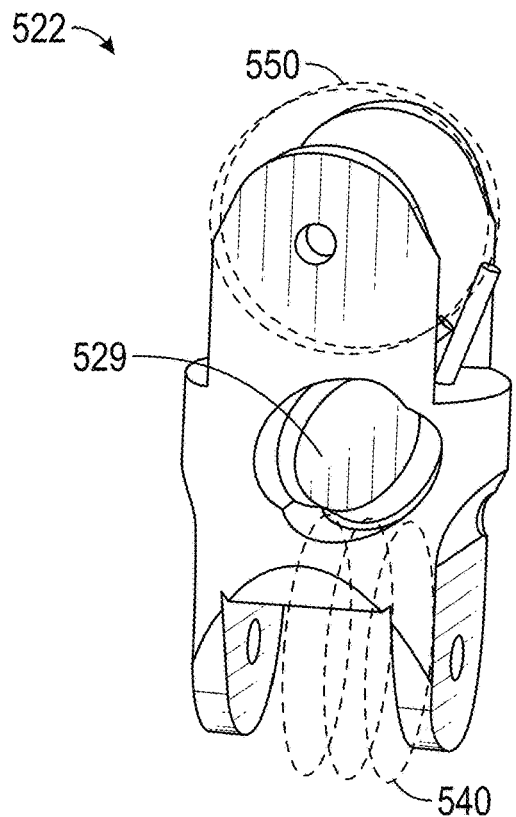
FIG. 25A illustrate an alternative embodiment of a distal clevis that includes hybrid redirect surfaces.
Figure 25B:
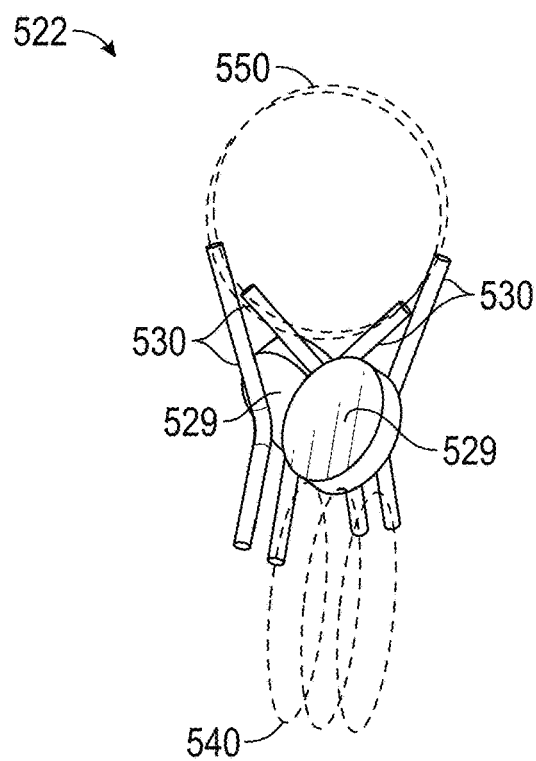
FIG. 25B illustrates an example cable path along static and dynamic redirect surfaces for the distal clevis of FIG. 25A.

FIGS. 25A and 25B illustrate an alternative embodiment of a distal clevis 522 that includes hybrid redirect surfaces. In this embodiment, dynamic redirect surfaces 529 (configured as pulleys) are configured to redirect pull wires 530 along a path that crosses from a far pitch pulley 540 to the opposite side of the yaw pulley 550. In this embodiment, the proximal pitch pulleys 540 can be all centered and aligned, which can allow them to be larger in size as they are all centered.

Figure 26A:
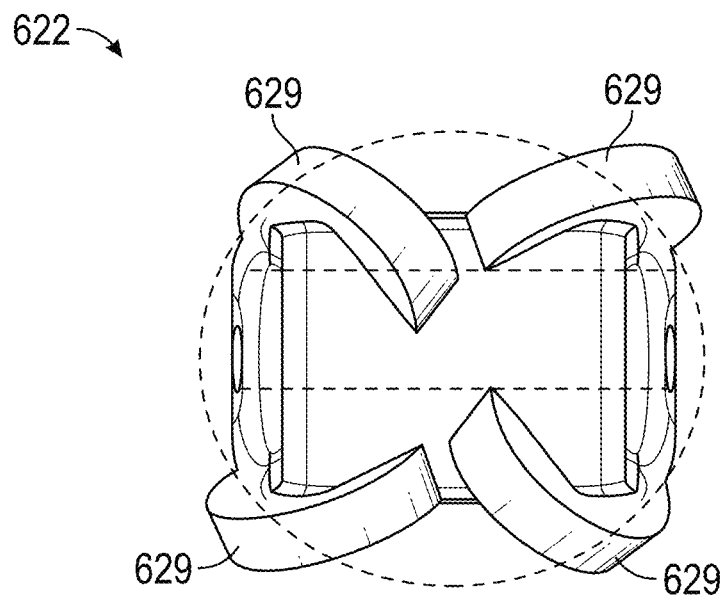
FIG. 26A illustrates an example of distal clevis that includes four dynamic redirect surfaces
Figure 26B:
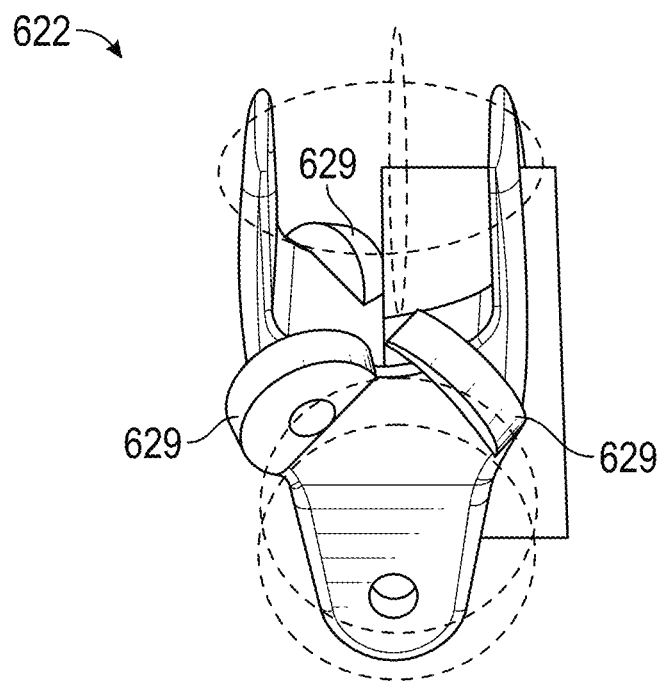
FIG. 26B illustrates another view of the distal clevis of FIG. 26A.

FIGS. 26A and 26B provide views of another embodiment of a distal clevis 622. In this embodiment, the stationary redirect surfaces have been replaced with dynamic redirect surfaces. Accordingly, the distal clevis 622 includes four redirect pulleys 629. In such a case, the instrument would not be considered to have a hybrid redirect surface because it only includes one type of redirect surface (dynamic).

3. Implementing Systems and Terminology

Implementations disclosed herein provide systems, methods and apparatus for medical instruments including wrists with hybrid redirect surfaces.

It should be noted that the terms "couple," "coupling," "coupled" or other variations of the word couple as used herein may indicate either an indirect connection or a direct connection. For example, if a first component is "coupled" to a second component, the first component may be either indirectly connected to the second component via another component or directly connected to the second component.

The phrases referencing specific computer-implemented processes/functions described herein may be stored as one or more instructions on a processor-readable or computer-readable medium. The term "computer-readable medium"

refers to any available medium that can be accessed by a computer or processor. By way of example, and not limitation, such a medium may comprise random access memory (RAM), read-only memory (ROM), electrically erasable programmable read-only memory (EEPROM), flash memory, compact disc read-only memory (CD-ROM) or other optical disk storage, magnetic disk storage or other magnetic storage devices, or any other medium that can be used to store desired program code in the form of instructions or data structures and that can be accessed by a computer. It should be noted that a computer-readable medium may be tangible and non-transitory. As used herein, the term "code" may refer to software, instructions, code or data that is/are executable by a computing device or processor.

The methods disclosed herein comprise one or more steps or actions for achieving the described method. The method steps and/or actions may be interchanged with one another without departing from the scope of the claims. In other words, unless a specific order of steps or actions is required for proper operation of the method that is being described, the order and/or use of specific steps and/or actions may be modified without departing from the scope of the claims.

As used herein, the term "plurality" denotes two or more. For example, a plurality of components indicates two or more components. The term "determining" encompasses a wide variety of actions and, therefore, "determining" can include calculating, computing, processing, deriving, investigating, looking up (e.g., looking up in a table, a database or another data structure), ascertaining and the like. Also, "determining" can include receiving (e.g., receiving information), accessing (e.g., accessing data in a memory) and the like. Also, "determining" can include resolving, selecting, choosing, establishing and the like.

The phrase "based on" does not mean "based only on," unless expressly specified otherwise. In other words, the phrase "based on" describes both "based only on" and "based at least on."

The previous description of the disclosed implementations is provided to enable any person skilled in the art to make or use the present invention. Various modifications to these implementations will be readily apparent to those skilled in the art, and the generic principles defined herein may be applied to other implementations without departing from the scope of the invention. For example, it will be appreciated that one of ordinary skill in the art will be able to employ a number corresponding alternative and equivalent structural details, such as equivalent ways of fastening, mounting, coupling, or engaging tool components, equivalent mechanisms for producing particular actuation motions, and equivalent mechanisms for delivering electrical energy. Thus, the present invention is not intended to be limited to the implementations shown herein but is to be accorded the widest scope consistent with the principles and novel features disclosed herein.

What is claimed is:

1. A medical instrument, comprising:
   (a) a shaft extending between a proximal end and a distal end;
   (b) a wrist positioned at the distal end of the shaft, the wrist comprising:
      (i) a proximal clevis connected to the distal end of the shaft and including a first proximal pulley configured to rotate in a first plane,
      (ii) a distal clevis pivotally connected to the proximal clevis and including a first distal pulley configured to rotate in a second plane, wherein the second plane is orthogonal to the first plane,
      (iii) a static redirect surface, wherein the static redirect surface is positioned between the first proximal pulley and the first distal pulley,
      (iv) a first redirect pulley including a dynamic redirect surface,
      (v) an axle pivotally connecting the proximal clevis to the distal clevis, wherein the first proximal pulley is mounted on the axle, and
      (vi) a second proximal pulley mounted on the axle,
      wherein the axle extends through a first support leg of the distal clevis, and
      wherein the first support leg of the distal clevis is positioned between the first proximal pulley and the second proximal pulley;
   (c) an end effector connected to the distal clevis of the wrist; and
   (d) a plurality of pull wires extending through the shaft and the wrist and engaged with the end effector, wherein:
      (i) the plurality of pull wires is configured to actuate the wrist and the end effector,
      (ii) a first pull wire segment of the plurality of pull wires engages the static redirect surface, and
      (iii) a second pull wire segment of the plurality of pull wires engages the dynamic redirect surface,
      wherein the static redirect surface receives the first pull wire segment thereagainst such that the first pull wire segment extends from the first proximal pulley, across the static redirect surface, and to the first distal pulley for directing the first pull wire segment from the proximal clevis toward the distal clevis.

2. The medical instrument of claim 1, wherein the static redirect surface and the dynamic redirect surface are positioned on the distal clevis of the wrist, wherein the distal clevis includes a base, and wherein the static redirect surface is distally positioned relative to the base of the distal clevis.

3. The medical instrument of claim 1, wherein the first pull wire segment engages the first proximal pulley, the static redirect surface, and the first distal pulley.

4. The medical instrument of claim 3, wherein the first proximal pulley is positioned at a proximal end of the distal clevis and the first distal pulley is positioned at a distal end of the distal clevis.

5. The medical instrument of claim 1 wherein the second pull wire segment engages the second proximal pulley configured to rotate on a first lateral side of the medical instrument; wherein the second pull wire segment engages a second distal pulley on a second lateral side of the medical instrument, wherein the second distal pulley is oriented orthogonally relative to the second proximal pulley; and wherein the first redirect pulley is positioned between the second proximal pulley and the second distal pulley.

6. The medical instrument of claim 1 wherein the end effector comprises at least one jaw; wherein actuation of the first pull wire segment causes the at least one jaw to open; and wherein actuation of the second pull wire segment causes the at least one jaw to close.

7. The medical instrument of claim 1, wherein the wrist further comprises:
   (i) a third proximal pulley mounted on the axle; and
   (ii) a fourth proximal pulley mounted on the axle;
   wherein the axle extends through a second support leg of the distal clevis, wherein the second support leg of the distal clevis is positioned between the third proximal pulley and the fourth proximal pulley, and wherein the third and fourth proximal pulleys are positioned between the first and second support legs of the distal clevis.

8. The medical instrument of claim 7, wherein the proximal clevis comprises third and fourth support legs; wherein the axle extends through the third and fourth support legs of the proximal clevis; and wherein the second and fourth proximal pulleys, the first and second support legs of the distal clevis, and the first and third pulleys are positioned between the first and second support legs of the proximal clevis.

9. The medical instrument of claim 1, further comprising:
  (a) the first redirect pulley positioned in the distal clevis configured to rotate about a first axis; and
  (b) a second redirect pulley positioned in the distal clevis configured to rotate about a second axis, wherein the second axis is not coaxial with the first axis.

10. The medical instrument of claim 1, wherein the end effector comprises grips of a bipolar energy instrument.

11. The medical instrument of claim 1, wherein the plurality of pull wires comprise n pull wires, and wherein actuation of one or more of the n pull wires facilitates control of n+1 degrees of freedom of the medical instrument.

12. A medical instrument, comprising:
  (a) a shaft extending between a proximal end and a distal end;
  (b) a wrist positioned at the distal end of the shaft, the wrist comprising:
    (i) a proximal clevis connected to the distal end of the shaft,
    (ii) a distal clevis pivotally connected to the proximal clevis by a proximal axle, wherein the distal clevis extends from the proximal clevis along a central longitudinal axis, wherein the distal clevis has an outer lateral surface at least partially surrounding the central longitudinal axis,
    (iii) a first proximal pulley rotatably mounted on the proximal axle,
    (iv) a second proximal pulley rotatably mounted on the proximal axle, wherein the proximal axle extends through a first support leg of the distal clevis that is positioned between the first pulley and the second pulley,
    (v) a distal axle extending through the distal clevis along a lateral axis, wherein the lateral axis is perpendicular to the central longitudinal axis,
    (vi) a first distal pulley rotatably mounted on the distal axle, and
    (vii) a second distal pulley rotatably mounted on the distal axle,
    wherein each of the first and second distal pulleys are positioned proximate to the central longitudinal axis of the distal clevis such that each of the first and second distally pulleys is laterally closer to the central longitudinal axis than the outer lateral surface of the distal clevis along the lateral axis; and
  (c) an end effector connected to the distal clevis of the wrist, wherein the end effector includes a first jaw member and a second jaw member, wherein the first jaw member extends from the first distal pulley, and wherein the second jaw member extends from the second distal pulley.

13. The medical instrument of claim 12, wherein the wrist further comprises:
  (i) a third proximal pulley rotatably mounted on the proximal axle, and
  (ii) a fourth proximal pulley rotatably mounted on the proximal axle,
  wherein the proximal axle extends through a second support leg of the distal clevis that is positioned between the third proximal pulley and the fourth proximal pulley.

14. The medical instrument of claim 13, wherein the second and third proximal pulleys are positioned between the first and second support legs of the distal clevis.

15. The medical instrument of claim 14, wherein the proximal clevis comprises a third support leg and a fourth support leg; wherein the proximal axle extends through the third and fourth support legs of the proximal clevis; and wherein the first, second, third, and fourth pulleys and the first and second support legs of the distal clevis are positioned between the third and fourth support legs of the proximal clevis.

16. The medical instrument of claim 15, further comprising first, second, third, and fourth pull wire segments contacting the first, second, third, and fourth pulleys, respectively, and wherein the first and fourth pull wire segments are associated with a close motion of the end effector and the second and third pull wire segments are associated with an open motion of the end effector.

17. The medical instrument of claim 16, wherein the wrist further comprises:
  (i) a first static redirect surface;
  (ii) a second static redirect surface;
  (iii) a first dynamic redirect surface; and
  (iv) a second dynamic redirect surface.

18. The medical instrument of claim 12, wherein the central longitudinal axis extends between the first and second distal pulleys.

19. The medical instrument of claim 18, wherein each of the first and second distal pulleys are adjacent to the central longitudinal axis.

* * * * *